United States Patent
Orentas et al.

(10) Patent No.: US 10,844,128 B2
(45) Date of Patent: Nov. 24, 2020

(54) COMPOSITIONS AND METHODS FOR TREATING CANCER WITH ANTI-CD123 IMMUNOTHERAPY

(71) Applicants: Lentigen Technology, Inc., Gaithersburg, MD (US); The U.S.A., as represented by the Secretary, Department of Health and Human Services, Bethesda, MD (US)

(72) Inventors: Rimas J. Orentas, Seattle, WA (US); Dina Schneider, Potomac, MD (US); Boro Dropulic, Ellicott City, MD (US); Dimiter S. Dimitrov, Frederick, MD (US); Zhongyu Zhu, Frederick, MD (US)

(73) Assignees: Lentigen Technology, Inc., Gaithersburg, MD (US); The U.S.A., as represented by The Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/578,063

(22) Filed: Sep. 20, 2019

(65) Prior Publication Data
US 2020/0010555 A1    Jan. 9, 2020

Related U.S. Application Data

(60) Provisional application No. 62/734,106, filed on Sep. 20, 2018.

(51) Int. Cl.
| | |
|---|---|
| A61K 39/00 | (2006.01) |
| C07K 14/47 | (2006.01) |
| A61K 39/395 | (2006.01) |
| A61K 35/17 | (2015.01) |
| C07K 14/705 | (2006.01) |
| C07K 19/00 | (2006.01) |
| C07K 16/28 | (2006.01) |
| C07K 14/725 | (2006.01) |
| C12N 15/10 | (2006.01) |
| C12N 15/86 | (2006.01) |
| A61K 38/00 | (2006.01) |

(52) U.S. Cl.
CPC .......... *C07K 16/2866* (2013.01); *A61K 35/17* (2013.01); *C07K 14/7051* (2013.01); *C07K 14/70517* (2013.01); *C07K 14/70578* (2013.01); *C12N 15/1037* (2013.01); *C12N 15/86* (2013.01); *A61K 38/00* (2013.01); *C07K 2317/622* (2013.01); *C07K 2319/02* (2013.01); *C07K 2319/03* (2013.01); *C12N 2740/15041* (2013.01)

(58) Field of Classification Search
None
See application file for complete search history.

(56) References Cited

U.S. PATENT DOCUMENTS

| | | | |
|---|---|---|---|
| 2016/0046724 A1* | 2/2016 | Brogdon | A61K 35/12 424/134.1 |
| 2016/0208018 A1* | 7/2016 | Chen | C07K 14/70596 |

FOREIGN PATENT DOCUMENTS

| | | |
|---|---|---|
| WO | WO 2015140268 | 9/2015 |
| WO | WO 2017075147 | 5/2017 |

OTHER PUBLICATIONS

Sridhar and Petrocca, Regional Delivery of Chimeric Antigen Receptor (CAR) T-Cells for Cancer Therapy, Cancers, 2017, pp. 1-10.*
D'Aloia etal, CAR-T cells: the long and winding road to solid tumors, Cell Death and Disease (2018) 9:282, pp. 1-12.*
Fumoto etal, Targeted Gene Delivery: Importance of Administration Routes, Intech, 2013, pp. 1-31.*
Breener and Okur, Overview of gene therapy clinical progress including cancer treatment with gene-modified T cells, Hematology Am Soc Hematol Educ Program. 2009 ; : 675-681.*
Kuerberuwa et al, CD19 CAR T Cells Expressing IL-12 Eradicate Lymphoma in Fully Lymphoreplete Mice through Induction of Host Immunity, Molecular therapy, Oncolytics, 2018, pp. 41-51.*

* cited by examiner

*Primary Examiner* — Maria Marvich
(74) *Attorney, Agent, or Firm* — Serge Sira, Esq.; Gregory J. Hwa, Esq.; Fish & Richardson P.C.

(57) ABSTRACT

Chimeric antigen receptors containing CD123 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

11 Claims, 4 Drawing Sheets
Specification includes a Sequence Listing.

COMPOSITIONS AND METHODS FOR TREATING CANCER WITH ANTI-CD123 IMMUNOTHERAPY

CROSS-REFERENCE TO RELATED APPLICATIONS

This non-provisional U.S. patent application claims priority to U.S. Provisional Patent Application No. 62/734,106 filed on Sep. 20, 2018, the entire contents of each of which are incorporated herein by reference.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in ASCII format and is hereby incorporated by reference in its entirety. Said ASCII copy, created on Sep. 20, 2019, is named SequenceListing.txt and is 175 kilobytes in size.

FIELD OF THE DISCLOSURE

This application relates to the field of cancer, particularly to CD123 antigen binding domains and chimeric antigen receptors (CARs) containing such CD123 antigen binding domains and methods of use thereof.

BACKGROUND

Cancer is one of the most deadly threats to human health. In the U. S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult.

AML is a devastating disease with overall survival rate of only 26%. While young patients tend to have a better prognosis for treatment in AML, the five year survival in older patients may be as low as only 5%. First line treatment of AML involves multiple rounds of chemotherapy, (i.e. induction, consolidation) which bear high risk of toxicity. If hematopoietic stem cell transplant is performed after the 1st remission, the 5 year disease-free survival rate is only 30-50% (see the world wide web at cancer.ca/en/cancer-information/cancer-type/leukemia-acute-myelogenous-aml/prognosis-and-survival/survival-statistics/? region=on). In addition, AML patients with high disease burden may not be candidates for bone marrow transplant, and minimal residual disease pre-transplant correlates with AML relapse. The present 1st line induction/consolidation therapy often fails to achieve MDR-negative remission of to sufficiently reduce tumor burden, thus the risk of AML relapse after 1st line therapy with or without BMT remains high (1) Biol Blood Marrow Transplant. 2006 June; 12(6):691-2., Leukemia burden and outcome of allogeneic transplant in acute myelogenous leukemia, Kamble R T, Hjortsvang E, Selby G B; (2) Leuk Lymphoma. 2015 May; 56(5): 1353-61. Impact of pre-transplant disease burden on the outcome of allogeneic hematopoietic stem cell transplant in refractory and relapsed acute myeloid leukemia: a single-center study. Tian H et al.). PBDCN is a rare myeloid neoplasm that is classified as a subtype of AML and is sometimes treated as AML with induction and consolidation chemotherapy, and sometimes as ALL. BMT is often administered at 1st remission. However, there are currently no ongoing clinical trials for PBDCN, and no approved 1st line treatment. (Leukemia Lymphoma Society, see the world wide web at lls.org/leukemia/blastic-plasmacytoid-dendritic-cell-neoplasm). Therefore, better therapeutic modalities are urgently needed for CD123+ malignancies.

CAR approaches targeting CD123 are superior to chemotherapy because they may achieve better efficacy in eliminating CD123+ tumor cells and tumor stem cells, and because they avoid the toxicities associated with chemotherapy. Importantly, CAR T cells are expected to be more efficient than chemotherapy in eliminating minimal residual disease, resulting in better long-term treatment prognosis. Furthermore, CAR123 may be used for tumor debulking as a bridge to transplant, as may help patient with high tumor burden become eligible for BMT.

CAR123 represents an improvement over prior art because unique human ScFv (hereinafter "hScFv") sequences are used in the CAR design, as opposed to murine-derived ScFvs employed in CAR designs elsewhere. Mouse-derived sequences carry the risk of immunogenicity, and may induce allergic or anaphylactic responses in patients, leading to CAR T elimination, or life-threatening anaphylaxis.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18(8):2199-209; Lehner M et al. PLoS One. 2012; 7 (2):e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, La.; Dec. 7-10, 2013) and a CD137/CD3-signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates that degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR+ T cells, rapid disappearance of the cells after infusion, and disappointing clinical activity. Accordingly, there is an urgent and long felt need in the art for discovering novel compositions and methods for treatment of AML using an approach that can exhibit specific and efficacious anti-tumor effect without the aforementioned shortcomings (i.e. high toxicity, insufficient efficacy).

The present invention addresses these needs by providing CAR compositions and therapeutic methods that can be used to treat cancers and other diseases and/or conditions. In particular, the present invention as disclosed and described herein provides CARs that may be used the treatment of diseases, disorders or conditions associated with dysregulated expression of CD123 and which CARs contain CD123 antigen binding domains that exhibit a high surface expression on transduced T cells, exhibit a high degree of cytolysis and transduced T cell in vivo expansion and persistence.

SUMMARY

Novel anti-CD123 antibodies or antigen binding domains thereof and chimeric antigen receptors (CARs) that contain such CD123 antigen binding domains are provided herein, as well as host cells (e.g., T cells) expressing the receptors, and nucleic acid molecules encoding the receptors. CAR may consist either of a single molecule expressed on the effector cell surface, or a CAR comprised of an effector cell-expressed signaling module and a soluble targeting module, such as when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-CD123 antibody or a fragment thereof is provided comprising a nucleic acid sequence selected from the group consisting of SEQ ID NOs: 1, 3, 5, 7, 9, 11, 15, 17, 19, 21, 23, 25, 69, 71, and 73.

In one embodiment, an isolated polynucleotide encoding a fully human anti-CD123 antibody or a fragment thereof is provided, wherein the antibody or a fragment thereof comprises a fragment selected from the group consisting of an Fab fragment, an F(ab')$_2$ fragment, an Fv fragment, and a single chain Fv (ScFv).

In one embodiment, an isolated polynucleotide encoding a fully human anti-CD123 antibody or a fragment thereof is provided, wherein the antibody or a fragment thereof comprises an amino acid sequence selected from the group consisting of SEQ ID NOs: 2, 4, 6, 8, 10, 12, 16, 18, 20, 22, 24, 26, 70, 72, and 74.

In one aspect, an isolated nucleic acid molecule encoding a chimeric antigen receptor (CAR) is provided comprising, from N-terminus to C-terminus, at least one CD123 antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, and 73, at least one transmembrane domain, and at least one intracellular signaling domain.

In one embodiment, an isolated nucleic acid molecule encoding the CAR is provided wherein the encoded extracellular CD123 antigen binding domain comprises at least one single chain variable fragment of an antibody that binds to CD123.

In another embodiment, an isolated nucleic acid molecule encoding the CAR is provided wherein the encoded extracellular CD123 antigen binding domain comprises at least one heavy chain variable region of an antibody that binds to CD123.

In one embodiment, the targeting domain of the CAR is expressed separately in the form of monoclonal antibody, ScFv Fab, Fab'2 and is containing an antigen-targeting domain comprising a nucleic acid sequence selected from the group consisting of SEQ ID NOs: 1, 3, 5, 7, 9, 11, 15, 17, 19, 21, 23, 25, 69, 71, and 73, coupled to an additional binding tag or epitope, whereas the effector-cell expressed component of the CAR contains a binding domain specifically directed to bind the tag or epitope expressed on the soluble CAR module, such as specific binding on the soluble component of the CAR to the cell bound component of the CAR forms the full functional CAR structure.

In another embodiment, the targeting domain of the CAR is expressed separately in the form of a monoclonal antibody, ScFv Fab, Fab'2 and contains an antigen-targeting domain comprising a nucleic acid sequence selected from the group consisting of SEQ ID NOs: 1, 3, 5, 7, 9, 11, 15, 17, 19, 21, 23, 25, 69, 71, and 73, and an additional ScFv, whereas the effector-cell expressed component of the CAR contains a tag or epitope specifically reactive with the additional ScFv expressed on the soluble CAR module, such as specific binding on the soluble component of the CAR to the cell bound component of the CAR forms the full functional CAR structure.

In yet another embodiment, an isolated nucleic acid molecule encoding the CAR is provided wherein the encoded CAR extracellular CD123 antigen binding domain further comprises at least one lipocalin-based antigen binding antigen (anticalins) that binds to CD123.

In one embodiment, an isolated nucleic acid molecule is provided wherein the encoded extracellular CD123 antigen binding domain is connected to the transmembrane domain by a linker domain.

In another embodiment, an isolated nucleic acid molecule encoding the CAR is provided wherein the encoded CD123 extracellular antigen binding domain is preceded by a sequence encoding a leader or signal peptide.

In yet another embodiment, an isolated nucleic acid molecule encoding the CAR is provided comprising at least one CD123 antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, and 73, and wherein the CAR additionally encodes an extracellular antigen binding domain targets an antigen that includes, but is not limited to, CD19, CD20, CD22, ROR1, mesothelin, CD33, CD38, CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD123 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 13, SEQ ID NO: 39, SEQ ID NO: 41, or SEQ ID NO: 43.

In yet another embodiment, an isolated nucleic acid molecule encoding the CAR is provided wherein the encoded leader sequence comprises the amino acid sequence of SEQ ID NO: 14 SEQ ID NO: 40, SEQ ID NO: 42, or SEQ ID NO: 44.

In one aspect, a chimeric antigen receptor (CAR) is provided herein comprising, from N-terminus to C-terminus, at least one CD123 antigen binding domain, at least one transmembrane domain, and at least one intracellular signaling domain.

In one embodiment, a CAR is provided wherein the extracellular CD123 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, the CAR is provided wherein CAR additionally encodes an extracellular antigen binding domain comprising CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises an immunoglobulin variable heavy chain only (VH) anti-CD19 antigen binding domain, an anti-CD20 VH antigen binding domain, an anti-CD22 VH antigen binding domain, an anti-ROR1 VH antigen binding domain, an anti-mesothelin VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-BCMA (CD269) VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-ROR1 P antigen binding domain, an anti-mesothelin P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 75. In one embodiment, the nucleic acid sequence encodes a CAR comprising the amino acid sequence of SEQ ID NO: 76.

In another embodiment, the nucleic acid sequence encoding a CAR comprises the nucleic acid sequence of SEQ ID NO: 77. In one embodiment, the nucleic acid sequence encodes a CAR comprising the amino acid sequence of SEQ ID NO: 78.

In another embodiment, the nucleic acid sequence encoding a CAR comprises the nucleic acid sequence of SEQ ID NO: 87. In one embodiment, the nucleic acid sequence encodes a CAR comprising the amino acid sequence of SEQ ID NO: 88.

In another embodiment, the nucleic acid sequence encoding a CAR comprises the nucleic acid sequence of SEQ ID NO: 89. In one embodiment, the nucleic acid sequence encodes a CAR comprising the amino acid sequence of SEQ ID NO: 90.

In another embodiment, the nucleic acid sequence encoding a CAR comprises the nucleic acid sequence of SEQ ID NO: 91. In one embodiment, the nucleic acid sequence encodes a CAR comprising the amino acid sequence of SEQ ID NO: 92.

In another embodiment, the nucleic acid sequence encoding a CAR comprises the nucleic acid sequence of SEQ ID NO: 93. In one embodiment, the nucleic acid sequence encodes a CAR comprising the amino acid sequence of SEQ ID NO: 94.

In another embodiment, the nucleic acid sequence encoding a CAR comprises the nucleic acid sequence of SEQ ID NO: 95. In one embodiment, the nucleic acid sequence encodes a CAR comprising the amino acid sequence of SEQ ID NO: 96.

In another embodiment, the nucleic acid sequence encoding a CAR comprises the nucleic acid sequence of SEQ ID NO: 97. In one embodiment, the nucleic acid sequence encodes a CAR comprising the amino acid sequence of SEQ ID NO: 98.

In another embodiment, the nucleic acid sequence encoding a CAR comprises the nucleic acid sequence of SEQ ID NO: 99. In one embodiment, the nucleic acid sequence encodes a CAR comprising the amino acid sequence of SEQ ID NO: 100.

In another embodiment, the nucleic acid sequence encoding a CAR comprises the nucleic acid sequence of SEQ ID NO: 101. In one embodiment, the nucleic acid sequence encodes a CAR comprising the amino acid sequence of SEQ ID NO: 102.

In another embodiment, the nucleic acid sequence encoding a CAR comprises the nucleic acid sequence of SEQ ID NO: 103. In one embodiment, the nucleic acid sequence encodes a CAR comprising the amino acid sequence of SEQ ID NO: 104.

In another embodiment, the nucleic acid sequence encoding a CAR comprises the nucleic acid sequence of SEQ ID NO: 105. In one embodiment, the nucleic acid sequence encodes a CAR comprising the amino acid sequence of SEQ ID NO: 106.

In another embodiment, the nucleic acid sequence encoding a CAR comprises the nucleic acid sequence of SEQ ID NO: 107. In one embodiment, the nucleic acid sequence encodes a CAR comprising the amino acid sequence of SEQ ID NO: 108.

In another embodiment, the nucleic acid sequence encoding a CAR comprises the nucleic acid sequence of SEQ ID NO: 109. In one embodiment, the nucleic acid sequence encodes a CAR comprising the amino acid sequence of SEQ ID NO: 110.

In another embodiment, the nucleic acid sequence encoding a CAR comprises the nucleic acid sequence of SEQ ID NO: 111. In one embodiment, the nucleic acid sequence encodes a CAR comprising the amino acid sequence of SEQ ID NO: 112.

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a CD8+ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising a CD123 antigen binding domain comprising the amino acid sequence selected from the group consisting of SEQ ID NOs: 2, 4, 6, 8, 10, 12, 16, 18, 20, 22, 24, 26, 70, 72, and 74; at least one linker domain; at least one transmembrane domain; and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD123, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of CD123 on a cell, is provided comprising a) contacting the cell with a human anti-CD123 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, and 74; and b) detecting the presence of CD123 wherein the presence of CD123 diagnoses for the disease, disorder or condition associated with the expression of CD123.

In one embodiment, the disease, disorder or condition associated with the expression of CD123 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of a CD123-related disease in a mammal, is provided comprising detecting the expression of CD123 in a sample derived from the mammal comprising: a) contacting the sample with a human anti-CD123 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, and 74; and b) detecting the presence of CD123 wherein the presence of CD123 diagnoses for a CD123-related disease in the mammal.

In another embodiment, a method of inhibiting CD123-dependent T cell inhibition, is provided comprising contacting a cell with a human anti-CD123 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, and 74. In one embodiment, the cell is selected from the group consisting of a CD123-expressing tumor cell, a tumor-associated macrophage, and any combination thereof.

In another embodiment, a method of blocking T-cell inhibition mediated by a CD123-expressing cell and altering the tumor microenvironment to inhibit tumor growth in a mammal, is provided comprising administering to the mammal an effective amount of a composition comprising an isolated anti-CD123 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, and 74. In one embodiment, the cell is selected from the group consisting of a CD123-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-CD123 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, and 74. In one embodiment, the antibody or fragment thereof inhibits the interaction between a first cell with a T cell, wherein the first cell is selected from the group consisting of a CD123-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD123 and/or one or more of the aforementioned antigens, under conditions sufficient to form an immune complex of the antigen binding domain on the CAR and the extracellular domain of CD123 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular CD123 antigen binding domain comprising the amino acid sequence of SEQ ID NOs: 2, 4, 6, 8, 10, 12, 16, 18, 20, 22, 24, 26, 70, 72, or 74, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one CD123 antigen binding domain comprising the amino acid sequence of SEQ ID NOs: 2, 4, 6, 8, 10, 12, 16, 18, 20, 22, 24, 26, 70, 72, or 74, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one CD123 antigen binding domain comprising the amino acid sequence of SEQ ID NOs: 2, 4, 6, 8, 10, 12, 16, 18, 20, 22, 24, 26, 70, 72, or 74, or any combination thereof; at least one transmembrane domain; and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

DETAILED DESCRIPTION

Definitions

Figure 1:
FIG. 1 depicts the construction of CARs targeting CD123. The anti-CD123 ScFv targeting domain was linked in frame to CD8 hinge and transmembrane domain, the 4-1BB (CD137) signaling domain and the CD3 zeta signaling domain.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−.20% or in some instances .+−.10%, or in some instances .+−.5%, or in some instances .+−.1%, or in some instances .+−.0.1% from the specified value, as such variations are appropriate to perform the disclosed methods.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for CD123 antibodies or fragments thereof as well as chimeric antigen receptors (CARs) having such CD123 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f, the UPenn-sponsored clinical trial using mouse derived SS1 ScFv sequence, NCT02159716), may also determine the functional activity of a CAR-expressing T cell.

The CARs disclosed herein are expressed at a high level in a cell. A cell expressing the CAR has a high in vivo proliferation rate, produces large amounts of cytokines, and has a high cytotoxic activity against a cell having, on its surface, a CD123 antigen to which a CAR binds. The use of a human extracellular CD123 antigen binding domain results in generation of a CAR that functions better in vivo, while avoiding the induction of anti-CAR immunity in the host immune response and the killing of the CAR T cell population. The CARs expressing the entirely human extracellular CD123 ScFv antigen binding domain exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to CD123. This latter property allows investigators to better tune efficacy vs toxicity, and/or tissue specificity of the CAR T product, since lower-affinity binders may have higher specificity to tumors vs normal tissues due to higher expression of CD123 on tumors than normal tissue, which may prevent on-target off tumor toxicity and bystander cell killing.

What follows is a detailed description of the inventive CARs including a description of their extracellular CD123 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD123 antigen binding domain capable of binding to CD123, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and CD123. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is CD123 and the tumors associated with expression of CD123 comprise lung mesothelioma, ovarian, and pancreatic cancers that express high levels of the extracellular protein CD123, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD123, CD33, c-Met, PSMA, Glycolipid F77, EGFRvIII, GD-2, MY-ESO-1 TCR, MAGE A3 TCR, and the like.

In a preferred embodiment, the antigen binding domain portion of the CAR targets the extracellular CD123 antigen.

In one preferred embodiment, the isolated nucleic acid molecule encoding the extracellular CD123 hScFv M12301 antigen binding domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded extracellular CD123 hScFv M12301 antigen binding domain comprises an amino acid sequence of SEQ ID NO: 2, or an amino acid sequence with 85%, 90%, 95%, 96%, 97%, 98% or 99% identity to an amino acid sequence of SEQ ID NO: 2.

In one preferred embodiment, the isolated nucleic acid molecule encoding the extracellular CD123 hScFv M12303 antigen binding domain comprises a nucleotide sequence of SEQ ID NO: 3, or a sequence with 85%, 90%, 95%, 96%, 97%, 98% or 99% identity thereof. In one embodiment, an isolated nucleic acid molecule is provided wherein the encoded extracellular CD123 hScFv M12303 antigen binding domain comprises an amino acid sequence of SEQ ID NO: 4, or an amino acid sequence with 85%, 90%, 95%, 96%, 97%, 98% or 99% identity to an amino acid sequence of SEQ ID NO: 4.

In one preferred embodiment, the isolated nucleic acid molecule encoding the extracellular CD123 hScFv M12304 antigen binding domain comprises a nucleotide sequence of SEQ ID NO: 5, or a sequence with 85%, 90%, 95%, 96%, 97%, 98% or 99% identity thereof. In one embodiment, an isolated nucleic acid molecule is provided wherein the encoded extracellular CD123 hScFv M12304 antigen binding domain comprises an amino acid sequence of SEQ ID NO: 6, or an amino acid sequence with 85%, 90%, 95%, 96%, 97%, 98% or 99% identity to an amino acid sequence of SEQ ID NO: 6.

In one preferred embodiment, the isolated nucleic acid molecule encoding the extracellular CD123 hScFv M12305 antigen binding domain comprises a nucleotide sequence of SEQ ID NO: 7, or a sequence with 85%, 90%, 95%, 96%, 97%, 98% or 99% identity thereof. In one embodiment, an isolated nucleic acid molecule is provided wherein the encoded extracellular CD123 hScFv M12305 antigen binding domain comprises an amino acid sequence of SEQ ID NO: 8, or an amino acid sequence with 85%, 90%, 95%, 96%, 97%, 98% or 99% identity to an amino acid sequence of SEQ ID NO: 8.

In one preferred embodiment, the isolated nucleic acid molecule encoding the extracellular CD123 hScFv M12306 antigen binding domain comprises a nucleotide sequence of SEQ ID NO: 9, or a sequence with 85%, 90%, 95%, 96%, 97%, 98% or 99% identity thereof. In one embodiment, an isolated nucleic acid molecule is provided wherein the encoded extracellular CD123 hScFv M12306 antigen binding domain comprises an amino acid sequence of SEQ ID NO: 10, or an amino acid sequence with 85%, 90%, 95%, 96%, 97%, 98% or 99% identity to an amino acid sequence of SEQ ID NO: 10.

In one preferred embodiment, the isolated nucleic acid molecule encoding the extracellular CD123 hScFv M12308 antigen binding domain comprises a nucleotide sequence of SEQ ID NO: 11, or a sequence with 85%, 90%, 95%, 96%, 97%, 98% or 99% identity thereof. In one embodiment, an isolated nucleic acid molecule is provided wherein the encoded extracellular CD123 hScFv M12308 antigen binding domain comprises an amino acid sequence of SEQ ID NO: 12, or an amino acid sequence with 85%, 90%, 95%, 96%, 97%, 98% or 99% identity to an amino acid sequence of SEQ ID NO: 12.

In one preferred embodiment, the isolated nucleic acid molecule encoding the extracellular CD123 hScFv M12309 antigen binding domain comprises a nucleotide sequence of SEQ ID NO: 15, or a sequence with 85%, 90%, 95%, 96%, 97%, 98% or 99% identity thereof. In one embodiment, an isolated nucleic acid molecule is provided wherein the encoded extracellular CD123 hScFv M12309 antigen binding domain comprises an amino acid sequence of SEQ ID NO: 16, or an amino acid sequence with 85%, 90%, 95%, 96%, 97%, 98% or 99% identity to an amino acid sequence of SEQ ID NO: 16.

In one preferred embodiment, the isolated nucleic acid molecule encoding the extracellular CD123 hScFv M12310 antigen binding domain comprises a nucleotide sequence of SEQ ID NO: 17, or a sequence with 85%, 90%, 95%, 96%, 97%, 98% or 99% identity thereof. In one embodiment, an isolated nucleic acid molecule is provided wherein the encoded extracellular CD123 hScFv M12310 antigen binding domain comprises an amino acid sequence of SEQ ID NO: 18, or an amino acid sequence with 85%, 90%, 95%, 96%, 97%, 98% or 99% identity to an amino acid sequence of SEQ ID NO: 18.

In one preferred embodiment, the isolated nucleic acid molecule encoding the extracellular CD123 hScFv M12311 antigen binding domain comprises a nucleotide sequence of SEQ ID NO: 19, or a sequence with 85%, 90%, 95%, 96%, 97%, 98% or 99% identity thereof. In one embodiment, an isolated nucleic acid molecule is provided wherein the encoded extracellular CD123 hScFv M12311 antigen binding domain comprises an amino acid sequence of SEQ ID NO: 20, or an amino acid sequence with 85%, 90%, 95%, 96%, 97%, 98% or 99% identity to an amino acid sequence of SEQ ID NO: 20.

In one preferred embodiment, the isolated nucleic acid molecule encoding the extracellular CD123 hScFv M12313 antigen binding domain comprises a nucleotide sequence of SEQ ID NO: 21, or a sequence with 85%, 90%, 95%, 96%, 97%, 98% or 99% identity thereof. In one embodiment, an isolated nucleic acid molecule is provided wherein the encoded extracellular CD123 hScFv M12313 antigen binding domain comprises an amino acid sequence of SEQ ID NO: 22, or an amino acid sequence with 85%, 90%, 95%, 96%, 97%, 98% or 99% identity to an amino acid sequence of SEQ ID NO: 22.

In one preferred embodiment, the isolated nucleic acid molecule encoding the extracellular CD123 hScFv M12314 antigen binding domain comprises a nucleotide sequence of SEQ ID NO: 23, or a sequence with 85%, 90%, 95%, 96%, 97%, 98% or 99% identity thereof. In one embodiment, an isolated nucleic acid molecule is provided wherein the encoded extracellular CD123 hScFv M12314 antigen binding domain comprises an amino acid sequence of SEQ ID NO: 24, or an amino acid sequence with 85%, 90%, 95%, 96%, 97%, 98% or 99% identity to an amino acid sequence of SEQ ID NO: 24.

In one preferred embodiment, the isolated nucleic acid molecule encoding the extracellular CD123 hScFv M12315 antigen binding domain comprises a nucleotide sequence of SEQ ID NO: 25, or a sequence with 85%, 90%, 95%, 96%, 97%, 98% or 99% identity thereof. In one embodiment, an isolated nucleic acid molecule is provided wherein the encoded extracellular CD123 hScFv M12315 antigen binding domain comprises an amino acid sequence of SEQ ID NO: 26, or an amino acid sequence with 85%, 90%, 95%, 96%, 97%, 98% or 99% identity to an amino acid sequence of SEQ ID NO: 26.

In one preferred embodiment, the isolated nucleic acid molecule encoding the extracellular CD123 hScFv M12316 antigen binding domain comprises a nucleotide sequence of SEQ ID NO: 69, or a sequence with 85%, 90%, 95%, 96%, 97%, 98% or 99% identity thereof. In one embodiment, an isolated nucleic acid molecule is provided wherein the encoded extracellular CD123 hScFv M12316 antigen binding domain comprises an amino acid sequence of SEQ ID NO: 70, or an amino acid sequence with 85%, 90%, 95%, 96%, 97%, 98% or 99% identity to an amino acid sequence of SEQ ID NO: 70.

In one preferred embodiment, the isolated nucleic acid molecule encoding the extracellular CD123 hScFv M12317 antigen binding domain comprises a nucleotide sequence of SEQ ID NO: 71, or a sequence with 85%, 90%, 95%, 96%, 97%, 98% or 99% identity thereof. In one embodiment, an isolated nucleic acid molecule is provided wherein the encoded extracellular CD123 hScFv M12317 antigen binding domain comprises an amino acid sequence of SEQ ID NO: 72, or an amino acid sequence with 85%, 90%, 95%, 96%, 97%, 98% or 99% identity to an amino acid sequence of SEQ ID NO: 72.

In one preferred embodiment, the isolated nucleic acid molecule encoding the extracellular CD123 hScFv M12318 antigen binding domain comprises a nucleotide sequence of SEQ ID NO: 73, or a sequence with 85%, 90%, 95%, 96%, 97%, 98% or 99% identity thereof. In one embodiment, an isolated nucleic acid molecule is provided wherein the encoded extracellular CD123 hScFv M12318 antigen binding domain comprises an amino acid sequence of SEQ ID NO: 74, or an amino acid sequence with 85%, 90%, 95%, 96%, 97%, 98% or 99% identity to an amino acid sequence of SEQ ID NO: 74.

The generation and binding characteristics of the specific CD123 variable heavy chain only and ScFv antigen binding fragments or antigen binders described herein is shown in Example 1.

In the various embodiments of the CD123-specific CARs disclosed herein, the general scheme is set forth in FIG. 1 and includes, from the N-terminus to the C-terminus, a signal or leader peptide, anti-CD123 ScFv, extracellular linker, CD8 transmembrane, 4-1BB, CD3 zeta, wherein the bolded text represents the cloning sites for linking domains.

In one embodiment, the nucleic acid sequence encoding a CAR comprises the nucleic acid sequence of SEQ ID NO: 75, and encodes the CAR comprising the amino acid sequence as set forth in SEQ ID NO: 76.

In one embodiment, the nucleic acid sequence encoding a CAR comprises the nucleic acid sequence of SEQ ID NO: 75, or a sequence with 85%, 90%, 95%, 96%, 97%, 98% or 99% identity thereof, and encodes the CAR comprising the amino acid sequence as set forth in SEQ ID NO: 76 or a sequence with 85%, 90%, 95%, 96%, 97%, 98% or 99% identity thereof.

In another embodiment, the nucleic acid sequence encoding a CAR comprises the nucleic acid sequence of SEQ ID NO: 77, and encodes the CAR comprising the amino acid sequence as set forth in SEQ ID NO: 78.

In another embodiment, the nucleic acid sequence encoding a CAR comprises the nucleic acid sequence of SEQ ID NO: 77 or a sequence with 85%, 90%, 95%, 96%, 97%, 98% or 99% identity thereof, and encodes the CAR comprising the amino acid sequence as set forth in SEQ ID NO: 78 or a sequence with 85%, 90%, 95%, 96%, 97%, 98% or 99% identity thereof.

In another embodiment, the nucleic acid sequence encoding a CAR comprises the nucleic acid sequence of SEQ ID NO: 87, and encodes the CAR comprising the amino acid sequence as set forth in SEQ ID NO: 88.

In another embodiment, the nucleic acid sequence encoding a CAR comprises the nucleic acid sequence of SEQ ID NO: 87 or a sequence with 85%, 90%, 95%, 96%, 97%, 98% or 99% identity thereof, and encodes the CAR comprising the amino acid sequence as set forth in SEQ ID NO: 88 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 89, and encodes the CAR comprising the amino acid sequence as set forth in SEQ ID NO: 90.

In yet another embodiment, the nucleic acid sequence encoding a CAR comprises the nucleic acid sequence of SEQ ID NO: 89 or a sequence with 85%, 90%, 95%, 96%, 97%, 98% or 99% identity thereof, and encodes the CAR comprising the amino acid sequence as set forth in SEQ ID NO: 90 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 91, and encodes the CAR comprising the amino acid sequence as set forth in SEQ ID NO: 92.

In yet another embodiment, the nucleic acid sequence encoding a CAR comprises the nucleic acid sequence of SEQ ID NO: 91 or a sequence with 85%, 90%, 95%, 96%, 97%, 98% or 99% identity thereof, and encodes the CAR comprising the amino acid sequence as set forth in SEQ ID NO: 92 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 93, and encodes the CAR comprising the amino acid sequence as set forth in SEQ ID NO: 94.

In yet another embodiment, the nucleic acid sequence encoding a CAR comprises the nucleic acid sequence of SEQ ID NO: 93 or a sequence with 85%, 90%, 95%, 96%, 97%, 98% or 99% identity thereof, and encodes the CAR comprising the amino acid sequence as set forth in SEQ ID NO: 94 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 95, and encodes the CAR comprising the amino acid sequence as set forth in SEQ ID NO: 96.

In yet another embodiment, the nucleic acid sequence encoding a CAR comprises the nucleic acid sequence of SEQ ID NO: 95 or a sequence with 85%, 90%, 95%, 96%, 97%, 98% or 99% identity thereof, and encodes the CAR comprising the amino acid sequence as set forth in SEQ ID NO: 96 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 97, and encodes the CAR comprising the amino acid sequence as set forth in SEQ ID NO: 98.

In yet another embodiment, the nucleic acid sequence encoding a CAR comprises the nucleic acid sequence of SEQ ID NO: 97 or a sequence with 85%, 90%, 95%, 96%, 97%, 98% or 99% identity thereof, and encodes the CAR comprising the amino acid sequence as set forth in SEQ ID NO: 98 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 99, and encodes the CAR comprising the amino acid sequence as set forth in SEQ ID NO: 100.

In yet another embodiment, the nucleic acid sequence encoding a CAR comprises the nucleic acid sequence of SEQ ID NO: 99 or a sequence with 85%, 90%, 95%, 96%, 97%, 98% or 99% identity thereof, and encodes the CAR comprising the amino acid sequence as set forth in SEQ ID NO: 100 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 101, and encodes the CAR comprising the amino acid sequence as set forth in SEQ ID NO: 102.

In yet another embodiment, the nucleic acid sequence encoding a CAR comprises the nucleic acid sequence of SEQ ID NO: 101 or a sequence with 85%, 90%, 95%, 96%, 97%, 98% or 99% identity thereof, and encodes the CAR comprising the amino acid sequence as set forth in SEQ ID NO: 102 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 103, and encodes the CAR comprising the amino acid sequence as set forth in SEQ ID NO: 104.

In yet another embodiment, the nucleic acid sequence encoding a CAR comprises the nucleic acid sequence of SEQ ID NO: 103 or a sequence with 85%, 90%, 95%, 96%, 97%, 98% or 99% identity thereof, and encodes the CAR comprising the amino acid sequence as set forth in SEQ ID NO: 104 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 105, and encodes the CAR comprising the amino acid sequence as set forth in SEQ ID NO: 106.

In yet another embodiment, the nucleic acid sequence encoding a CAR comprises the nucleic acid sequence of SEQ ID NO: 105 or a sequence with 85%, 90%, 95%, 96%, 97%, 98% or 99% identity thereof, and encodes the CAR comprising the amino acid sequence as set forth in SEQ ID NO: 106 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 107, and encodes the CAR comprising the amino acid sequence as set forth in SEQ ID NO: 108.

In yet another embodiment, the nucleic acid sequence encoding a CAR comprises the nucleic acid sequence of SEQ ID NO: 107 or a sequence with 85%, 90%, 95%, 96%, 97%, 98% or 99% identity thereof, and encodes the CAR comprising the amino acid sequence as set forth in SEQ ID NO: 108 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 109, and encodes the CAR comprising the amino acid sequence as set forth in SEQ ID NO: 110.

In yet another embodiment, the nucleic acid sequence encoding a CAR comprises the nucleic acid sequence of SEQ ID NO: 109 or a sequence with 85%, 90%, 95%, 96%, 97%, 98% or 99% identity thereof, and encodes the CAR comprising the amino acid sequence as set forth in SEQ ID NO: 110 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 111, and encodes the CAR comprising the amino acid sequence as set forth in SEQ ID NO: 112.

In yet another embodiment, the nucleic acid sequence encoding a CAR comprises the nucleic acid sequence of SEQ ID NO: 111 or a sequence with 85%, 90%, 95%, 96%, 97%, 98% or 99% identity thereof, and encodes the CAR comprising the amino acid sequence as set forth in SEQ ID NO: 112 or a sequence with 85%, 90%, 95%, 96%, 97%, 98% or 99% identity thereof.

The surface expression of anti-CD123 CARs incorporating immunoglobulin heavy chain variable domain (VH) and single chain fragment variable (ScFv) sequences reactive with CD123 antigen, is shown in Example 2 infra. The expression level for each ScFv- or VH-containing CAR was determined by flow cytometric analysis of LV-transduced T cells from healthy donors using a recombinant CD123-Fc peptide, followed by anti-human Fc F(ab')2 fragment conjugated to AF647, and detected in the APC channel, (c.f, Example 2, FIG. 3). The VH-based anti-CD123 CAR constructs 1905 and 1906 (black traces) were readily detected on the surface of T cells from two donors, demonstrating the reproducibility of T cell transduction. By contrast, no CAR expression was detected in the negative control non-transduced T cells (gray traces), and GFP control (not shown), thus demonstrating the specificity of the detection method used (c.f, Example 2, FIG. 3). Similarly, the ScFv-based anti-CD123 CAR constructs 1936, 1937, 1938 and 1939 were highly expressed in human primary T cells (black traces) as compared to non-transduced T cell controls (gray traces). Representative results from one donor are shown.

Figure 2:
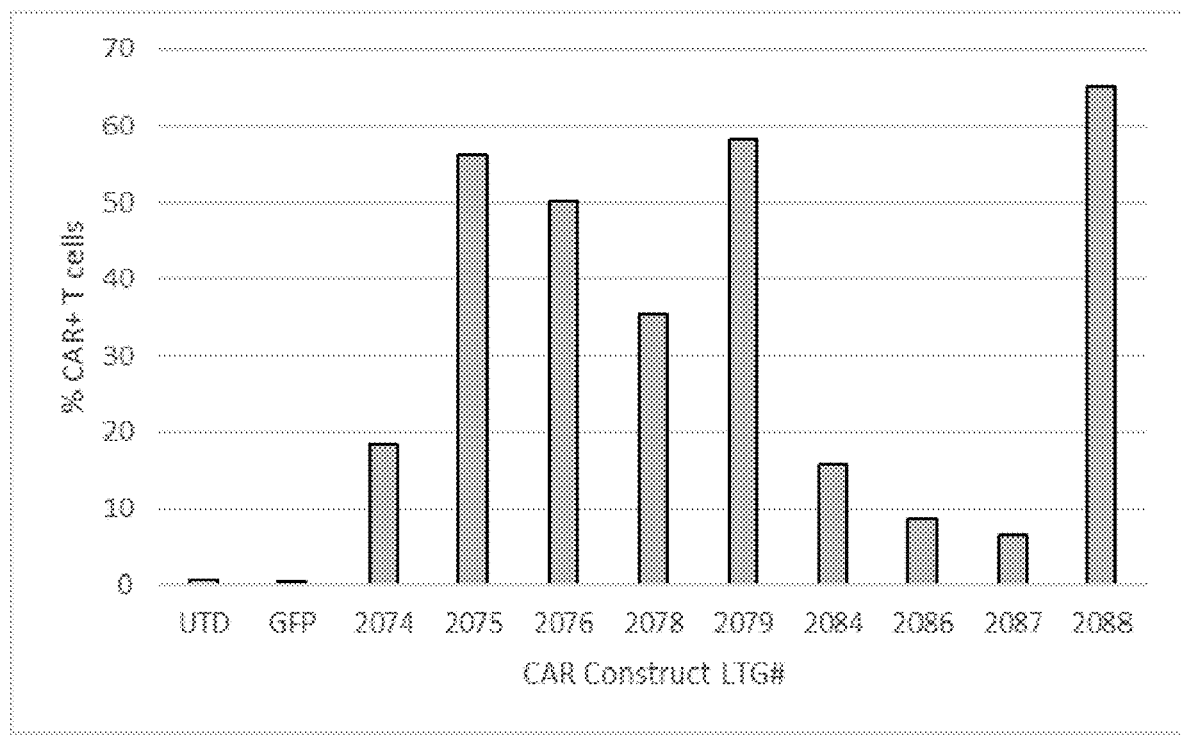
FIG. 2 depicts surface expression of CD123-targeting CAR T constructs on human primary T cells. CAR T expression was determined by flow cytometry. T cells were activated with Miltenyi Biotec TransAct TM CD3 CD28 reagent in the presence of IL-2, and transduced with LV as described in Materials and Methods. On culture day 8, viable transduced T cells (7-AAD negative) were assayed for CAR surface expression using Protein L-biotin reagent, followed by streptavidin-PE. The LV used in transduction is listed below each bar. Bars represent the percentage of CAR T-positive populations in relation to non-transduced T cell control (UTD). Data are representative of three independent experiments performed with CAR T cells from three separate donors.
Figure 3:
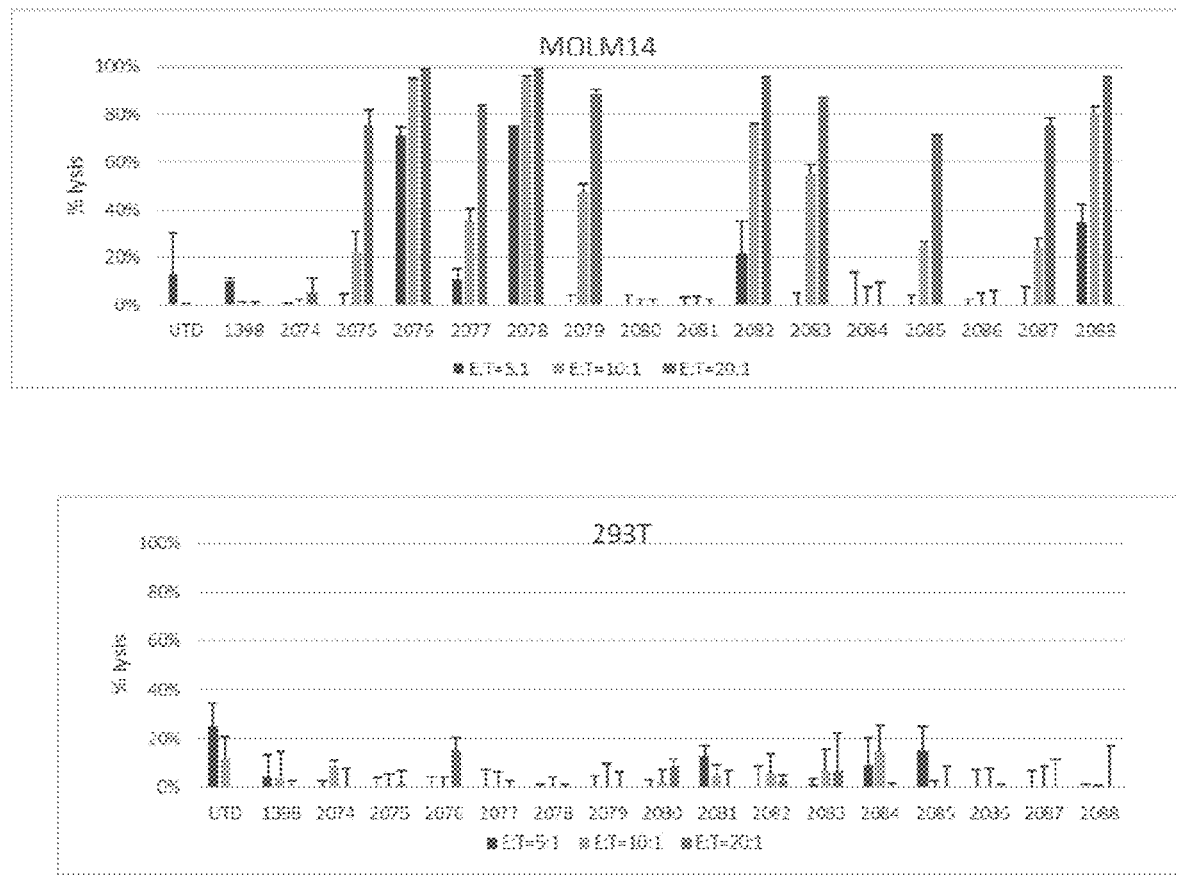
FIG. 3 depicts CAR T cytotoxicity in vitro. Luciferase-based cytotoxicity assays were performed using, CD123-positive AML line MOLM-14, or CD123-negative cell line 293T, stably transduced with luciferase. Bars represent mean+SD values from three technical replicates. Data are representative of three independent experiments performed with CAR T cells from three separate donors.

As shown in Example 2, high cytolytic activity of the CD123 CARs was demonstrated when lentiviral vectors (LV) expressing the following CARs were created and tested for anti-leukemia activity. Each experimental CAR contains the CD8 hinge and transmembrane domain, the 4-1BB costimulatory domain and the CD3-zeta chain signaling domain, and the specific anti-CD123 ScFv-derived targeting domain as noted therein (FIG. 1). In order to generate CAR T cells, lentiviral vector preparations encoding each of the novel anti-CD123 CAR constructs were generated, and used for the transduction of primary human T cells. CAR expression was determined by flow cytometry using Protein L (FIG. 2). CAR constructs LTG 2075, LTG2076, LTG2078, LTG2079, LTG2088 demonstrated high CAR surface expression, ranging 35%-55% CAR+ T cells (FIG. 2). Protein L is only suitable for the detection of ScFv sequences comprised of kappa light chain, therefore some sequences comprised of lambda light chain which were not detected, could nevertheless be expressed in CAR T cells. The cytotoxic potential of CAR123 candidates was assessed in luciferase-based overnight killing assays using a CD123+ AML target line MOLM-14 or a control 293T line, which is CD33− (FIG. 3). CAR T cells (effectors) and tumor cells (targets) were co-incubated overnight at effector to target ratio (E:T) of 5, 10, or 20. CAR123 constructs LTG2075, LTG2076, LTG2077, LTG2078, LTG2079, LTG2082, LTG2083, LTG2085, LTG2087, LTG2088 demonstrated potent and dose-dependent cytotoxicity vs CD123+ MOLM-14 target cells (FIG. 3). Moreover, negative control comprised of untransduced T cells (UTD) or GFP-transduced T cells (LTG1398) yielded no cytotoxicity, confirming that the killing was CAR-specific (FIG. 3). By comparison, no killing activity against the control CD123-293T cells was observed, indicating that the cytotoxic function of CAR123 cells is target-specific (FIG. 3). Therefore, the cytolytic activity of anti CD123 CARs that was observed against CD123-expressing MOLM-14 tumor cells is both target-specific and CART-dependent.

Figure 4:
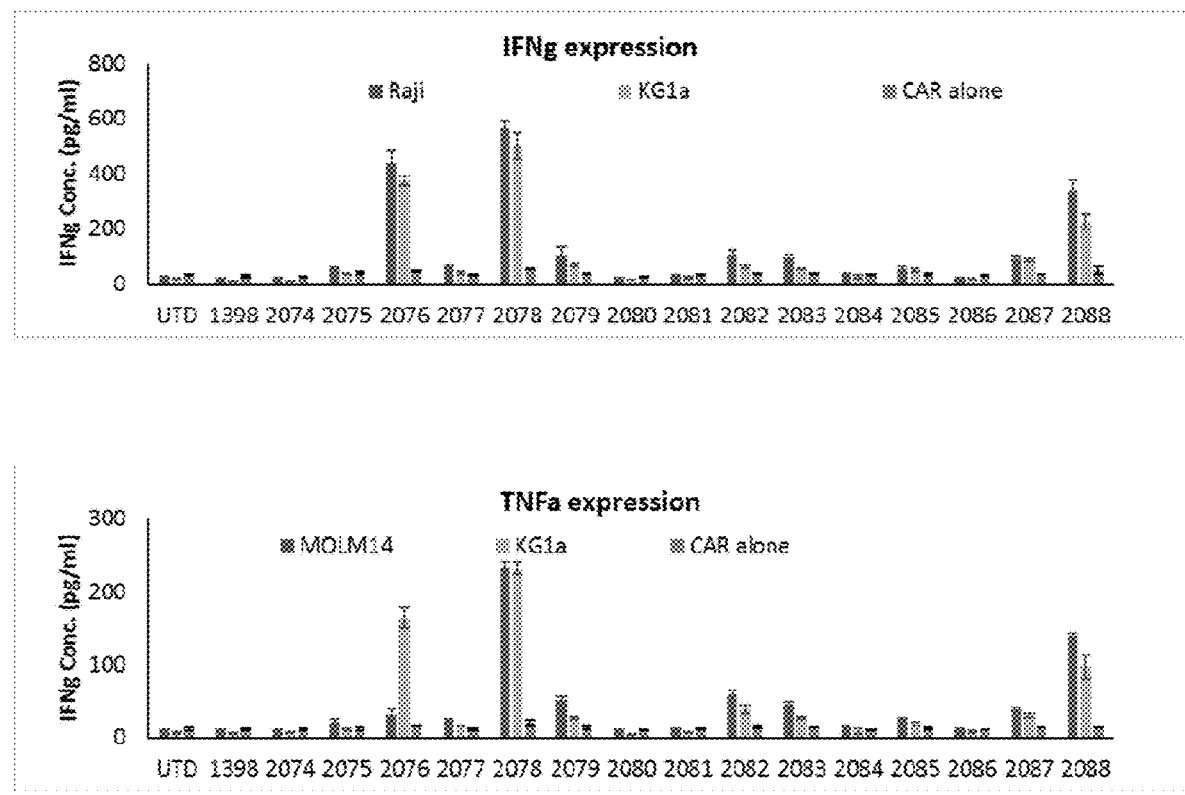
FIG. 4 depicts CAR T cytokine release in response to AML cell lines. Cytokine production by CAR-T, listed on the x-axis, upon overnight co-culture with MOLM-14 or KG-1a AML lines at an E:T ratio of 10:1, was measured using ELISA. Bars represent mean+SD of three replicate samples. Data are representative of three independent experiments performed with CAR T cells from three separate donors.

The capacity of anti-CD123 CAR T cells for cytokine secretion was then evaluated. CD123+ AML tumor cell lines MOLM-14 or Kg-1a were co-incubated with CAR T cells or control T cells at effector to target ratio of 10:1 overnight, and culture supernatants were analyzed by ELISA for IFN gamma and TNF alpha (FIG. 4). Of note, CAR T-expressing cells LTG2076, LTG2078 and LTG2088 elaborated high levels of IFN gamma and TNF alpha, whereas most of the other CAR constructs, as well as the negative control NT and 1398 groups yielded no appreciable cytokine induction. This result is in contrast with strong in vitro cytolytic function of LTG2075, LTG2077, LTG2082, LTG2083, LTG2085, LTG2087 (c.f, FIG. 3), and suggests that cytotoxicity does not always correlate with cytokine secretion profile, and multiple CAR T functional endpoints need to be tested on construct by construct basis. This finding also suggests that it may be possible to select CAR123 constructs which efficiently kill tumors yet have a low risk of inducing cytokine release syndrome, thus have a better safety profile.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular CD123 variable heavy chain only and ScFv antigen binding domains, other nucleotide and/or amino acid variants within the CD123 variable heavy chain only and ScFv antigen binding domains may be used to derive the CD123 antigen binding domains for use in the CARs described herein.

Depending on the desired antigen to be targeted, the CAR can be additionally engineered to include the appropriate antigen binding domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR additionally targets CD19. Preferably, the antigen binding domain in the CAR is anti-CD19 ScFv, wherein the nucleic acid sequence of the anti-CD19 ScFv comprises the sequence set forth in SEQ ID NO: 37 In one embodiment, the anti-CD19 ScFv comprises the nucleic acid sequence that encodes the amino acid sequence of SEQ ID NO: 30. In another embodiment, the anti-CD19 ScFv portion of the CAR comprises the amino acid sequence set forth in SEQ ID NO: 38.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picomaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas,* or *Salmonella*. Particularly, there is provided a CAR capable of binding to an antigen derived from an infectious bacterium, for example, *Helicobacter pyloris, Legionella pneumophilia,* a bacterial strain of Mycobacteria sps. (e.g. *M. tuberculosis, M. avium, M. intracellulare, M. kansaii,* or *M. gordonea), Staphylococcus aureus, Neisseria gonorrhoeae, Neisseria meningitides, Listeria monocytogenes, Streptococcus pyogenes,* Group A *Streptococcus,* Group B *Streptococcus (Streptococcus agalactiae), Streptococcus pneumoniae,* or *Clostridium tetani,* or a combination thereof.

2. Transmembrane Domain

With respect to the transmembrane domain, the CAR comprises one or more transmembrane domains fused to the extracellular CD33 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 27. In one embodiment, the CD8 transmembrane domain comprises the nucleic acid sequence that encodes the amino acid sequence of SEQ ID NO: 28. In another embodiment, the CD8 transmembrane domain comprises the amino acid sequence of SEQ ID NO: 28.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:28, or a sequence with 95-99% identity to an amino acid sequence of SEQ ID NO:28.

In some instances, the transmembrane domain of the CAR comprises the CD8.alpha.hinge domain. In one embodiment, the CD8 hinge domain comprises the nucleic acid sequence of SEQ ID NO: 29. In one embodiment, the CD8 hinge domain comprises the nucleic acid sequence that encodes the amino acid sequence of SEQ ID NO: 30. In another embodiment, the CD8 hinge domain comprises the amino acid sequence of SEQ ID NO: 30, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

In one embodiment, the transmembrane domain in the CAR of the invention is the TNFRSF19 transmembrane domain. In one embodiment, the TNFRSF19 transmembrane domain comprises the nucleic acid sequence of SEQ ID NO: 51. In one embodiment, the TNFRSF19 transmembrane domain comprises the nucleic acid sequence that encodes the amino acid sequence of SEQ ID NO: 52. In another embodiment, the TNFRSF19 transmembrane domain comprises the amino acid sequence of SEQ ID NO: 52.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 52, or a sequence with 95-99% identity to an amino acid sequence of SEQ ID NO: 52.

3. Spacer Domain

In the CAR, a spacer domain, also termed hinge domain, can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 31) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain (CH1 region or CL region, for example, a peptide having an amino acid sequence shown in SEQ ID NO: 32) can be used. Further, the spacer domain may be an artificially synthesized sequence.

In addition, an entire or a part of amino acids comprising the constant region of a human IgG4 (UniProt ID: P01861), including CH1, (amino acid numbers 1-98), hinge, SEQ ID NO: 80, and the corresponding nucleotide SEQ ID NO:79, (amino acid numbers 99-110), CH2, amino acid SEQ ID NO: 81 and corresponding nucleotide SEQ ID NO: 80, (amino acid numbers 111-220) and CH3, SEQ ID NO:84 and corresponding nucleotide SEQ ID NO: 83, (amino acid numbers 221-327) or a combination thereof, such as IgG4 Hinge CH2 CH3 domain, SEQ ID NO: 86, and the corresponding nucleotide SEQ ID NO: 85, can be used.

In one embodiment, the spacer domain of the CAR comprises the TNFRSF19 hinge domain which comprises the nucleic acid sequence of SEQ ID NO: 53. In one embodiment, the TNFRSF19 hinge domain comprises the nucleic acid sequence that encodes the amino acid sequence of SEQ ID NO: 54. In another embodiment, the TNFRSF19 hinge domain comprises the amino acid sequence of SEQ ID NO: 54, or a sequence with 95-99% identify thereof.

In one embodiment, the spacer domain of the CAR comprises the TNFRSF19 truncated hinge domain comprises the nucleic acid sequence of SEQ ID NO: 55. In one embodiment, the TNFRSF19 truncated hinge domain comprises the nucleic acid sequence that encodes the amino acid sequence of SEQ ID NO: 56. In another embodiment, the TNFRSF19 truncated hinge domain comprises the amino acid sequence of SEQ ID NO: 56, or a sequence with 95-99% identify thereof.

In one embodiment, the TNFRSF19 hinge and transmembrane domains comprise the nucleic acid sequence of SEQ ID NO: 49. In one embodiment, the TNFRSF19 hinge and transmembrane domains comprise the nucleic acid sequence that encodes the amino acid sequence of SEQ ID NO: 50. In another embodiment, the TNFRSF19 hinge and transmembrane domains comprise the amino acid sequence of SEQ ID NO: 50, or a sequence with 95-99% identify thereof.

In one embodiment, a CD8a hinge domain is fused to a TNFRSF19 transmembrane domain comprising the nucleic acid sequence of SEQ ID NO: 57. In one embodiment, the CD8a hinge domain is fused to a TNFRSF19 transmembrane domain comprises the nucleic acid sequence that encodes the amino acid sequence of SEQ ID NO: 58. In another embodiment, the CD8a hinge domain is fused to a TNFRSF19 transmembrane domain comprises the amino acid sequence of SEQ ID NO: 58, or a sequence with 95-99% identify thereof.

Further, in the CAR, a signal peptide sequence, also termed leader peptide, can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 14).

In one embodiment, the CD8 alpha leader peptide, is comprising the nucleic acid sequence of SEQ ID NO: 43. In one embodiment, CD8 alpha leader peptide comprises the nucleic acid sequence that encodes the amino acid sequence of SEQ ID NO: 44. In another embodiment, the CD8a hinge domain is fused to a TNFRSF19 transmembrane domain comprises the amino acid sequence of SEQ ID NO: 44, or a sequence with 95-99% identify thereof.

In another embodiment, the GMCSF leader peptide, is comprising the nucleic acid sequence of SEQ ID NO: 39. In one embodiment, the GMCSF leader peptide, comprises the nucleic acid sequence that encodes the amino acid sequence of SEQ ID NO: 40. In another embodiment, the CD8a hinge domain is fused to a TNFRSF19 transmembrane domain comprises the amino acid sequence of SEQ ID NO: 40, or a sequence with 95-99% identify thereof.

In another embodiment, the TNFRSF19 leader peptide is comprising the nucleic acid sequence of SEQ ID NO: 41. In one embodiment, TNFRSF19 leader peptide, and CD8 alpha leader peptide comprises the nucleic acid sequence that encodes the amino acid sequence of SEQ ID NO: 42. In another embodiment, the CD8a hinge domain is fused to a TNFRSF19 transmembrane domain comprises the amino acid sequence of SEQ ID NO: 42, or a sequence with 95-99% identify thereof.

In one embodiment, a tag sequence encoding a truncated sequence of epidermal growth factor receptor (tEGFR) is comprising the nucleic acid sequence of SEQ ID NO: 67. In one embodiment, tEGFR comprises the nucleic acid sequence that encodes the amino acid sequence of SEQ ID NO: 68. In another embodiment, the tEGFR tag comprises the amino acid sequence of SEQ ID NO: 68, or a sequence with 95-99% identify thereof.

In one embodiment, a furin recognition site and downstream T2A self-cleaving peptide sequence, designed for simultaneous bicistronic expression of the tag sequence and the CAR sequence, is comprising the nucleic acid sequence of SEQ ID NO: 65. In one embodiment, furin and T2A sequence comprises the nucleic acid sequence that encodes the amino acid sequence of SEQ ID NO: 66. In another embodiment, the tEGFR tag comprises the amino acid sequence of SEQ ID NO: 66 or a sequence with 95-99% identify thereof.

In one embodiment, an upstream furin recognition site and T2A self-cleaving peptide sequence and a furin recognition downstream site, designed for simultaneous bicistronic expression of the tag sequence and the CAR sequence, is comprising the nucleic acid sequence of SEQ ID NO: 67. In one embodiment, furin and T2A sequence comprises the nucleic acid sequence that encodes the amino acid sequence of SEQ ID NO: 68. In another embodiment, the tEGFR tag comprises the amino acid sequence of SEQ ID NO: 68 or a sequence with 95-99% identify thereof.

In one embodiment, the targeting domain of the CAR is expressed separately in the form of monoclonal antibody, ScFv Fab, Fab'2 and is containing at binding tag or epitope, whereas the effector-cell expressed component of the CAR contains a binding domain specifically directed to bind the tag or epitope expressed on the soluble CAR module, such as specific binding on the soluble component of the CAR to the cell bound component forms the full functional CAR structure.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.--932170.1), amino acid numbers 45 to 86 of Fc.epsilon.RI.gamma. (NCBI RefSeq: NP.sub.--004097.1), amino acid numbers 201 to 244 of Fc.epsilon.RI.beta. (NCBI RefSeq: NP.sub.--000130.1), amino acid numbers 139 to 182 of CD3.gamma. (NCBI RefSeq: NP.sub.--000064.1), amino acid numbers 128 to 171 of CD3.delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8.alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134 (OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 33, SEQ ID NO: 45, or SEQ ID NO: 59, respectively and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 34, SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 34, SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

In one embodiment, the intracellular domain in the CAR is designed to comprise the signaling domain of CD28 and the signaling domain of CD3-zeta, wherein the signaling domain of CD28 comprises the nucleic acid sequence set forth in SEQ ID NO: 45, or SEQ ID NO: 59, respectively, and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of CD28 and the signaling domain of CD3-zeta, wherein the signaling domain of CD28 comprises the nucleic acid sequence that encodes the amino acid sequence of SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of CD28 and the signaling domain of CD3-zeta, wherein the signaling domain of CD28 comprises the amino acid sequence set forth in SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, omithine, -aminocyclopentane carboxylic acid, a-aminocyclohexane carboxylic acid, a-aminocycloheptane carboxylic acid, a-(2-amino-2-norbomrane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used.

Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al. (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λvTIO, λvTI 1, λZapII (Stratagene), EMBL4, and λNMI 149, also can be used. Examples of plant expression vectors include pBIO1, pBI101.2, pBHO10.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a $E.$ $coli$ cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., Th1 and Th2 cells, $CD8^+$ T cells (e.g., cytotoxic T cells), tumor infiltrating cells, memory T cells, memory stem cells, i.e. Tscm, naive T cells, and the like. The T cell may be a $CD8^+$ T cell or a $CD4^+$ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-α, granulocyte/monocyte colony stimulating factor (GM-CSF), tumor necrosis factor a (TNF-α) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a non-toxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science,* 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Isolation of human CD123-Specific Antibodies from a Fully Human Yeast Display ScFv Library Materials and Methods:

A large yeast display human naive single chain variable fragment (ScFv) antibody library was used to isolate anti-human CD123 antibodies described herein. The library was constructed using a collection of human antibody gene repertoires from more than 60 individuals. Three rounds of magnetic-activated cell sorting (MACS) were performed to enrich human ScFv binders to the recombinant human CD123-Fc. For the first round of yeast library panning, the yeast display ScFv library ($5 \times 10^{10}$ cells) was incubated with 5 μg/mL CD123-Fc in 15 ml PBSA (consisting of 0.1% Bovine Serum Albumin (BSA) in Dulbecco's phosphate-buffered saline (PBS) buffer), at room temperature on a rotator for 1.5 hours. After two times washing with 25 ml PBSA, the yeast library mix was incubated with 100 μL Protein G microbeads (Miltenyi Biotec) at room temperature on a rotator for 30 minutes. After one time washing, the library mix was resuspended in 50 ml of PBSA and loaded onto the MACS cell separation column (LS column). After three times washing with 10 ml PBSA. The yeast displayed ScFv binders to the column were then eluted two times with 2 ml PBSA. These eluted yeast cells were combined and then resuspended into 50 ml SDCAA medium (20 g D-glucose, 6.7 g BD Difco™ Yeast Nitrogen Base without Amino Acids, 5 g Bacto™ Casamino Acids, 5.4 g Na2.HPO4, and 8.56 g NaH2PO4.H2O in 1 L water) and amplified with shaking at 225 rpm at 30° C. for 20 hours. The amplified pool was then induced in SGCAA medium (consisting of the same composition of SDCAA medium, but containing galactose instead of glucose), with shaking at 225 rpm at 30° C. for another 16 hours and used for next round of panning. The same process was repeated two more times to enrich the CD123-Fc specific binders.

To further enrich the binders with higher affinity and better specificity, FACS based sorting was employed to isolate the strongest binders from the pool. The induced pool was incubated with 1 μg/ml of CD123-Fc at room temperature for 1 hour and then stained with Anti-c-Myc-Alexa 488 and Goat anti-Hu-Fc PE conjugates, the top 1% of the pool with the highest PE versus FITC signal was gated and sorted. The sorted pool was amplified in SDCAA medium and yeast plasmid DNA was extracted and transformed into bacterial for single clone DNA sequencing. 40 random clones were sequenced and 36 unique sequences were identified. 15 CD123 ScFv clones designated as M12301, M12303, M12304, M12305, M12306, M12308, M12309, M12310, M12311, M12313, M12314, M12315, M12316, M12317 and M12318, respectively, which were cloned into CAR constructs for CAR-T function screening, as set forth in Example 2, Table 1.

Example 2

Generation of CD123-Targeting CAR T Constructs Incorporating Fully Human Binder ScFv Sequences Derived From Yeast Display Library Few treatment options exist for AML, and treatment-associated toxicities and post-treatment disease relapse are common. Moreover, immunotherapies employing non-human sequences, such as mouse-derived antibodies, may result in therapy rejection or adverse reactions in patients. In order to develop a new CAR T treatment for AML, fifteen CD123-targeting CAR T constructs incorporating fully human ScFv targeting domains were designed and evaluated for anti-tumor activity.

Materials and Methods:

(a) Cell Lines

The AML cell lines MOLM-14 and Kg-1a, were purchased from DSMZ (Leibniz Institute DSMZ, Braunschwieg, Germany) and the American Tissue Culture Collection (ATCC, Manassass, Va.), respectively. Human Embryonic kidney line 293T was purchased from ATCC (Gibco/Thermo Fisher Scientific, Grand Island, N.Y.). Single-cell clones of luciferase-expressing cell lines were generated by stably transducing wild-type tumor lines with lentiviral vector encoding firefly luciferase (Lentigen). Whole blood was collected from healthy volunteers at Oklahoma Blood Institute (OBI) with donors' written consent. Processed buffy coats were purchased from OBI (Oklahoma City, Okla.). The CD4-positive and CD8-positive human T cells were purified from buffy coats via positive selection using a 1:1 mixture of CD4– and CD8– Micro-Beads (Miltenyi Biotec, Bergisch Gladbach, Germany) according to manufacturer's protocol.

(b) Creation of Chimeric Antigen Receptor (CAR)—Expression Vectors

CAR antigen-binding domains, ScFv, sequences were derived from human anti-CD123 ScFv. CAR T constructs were generated by linking the binder sequence in frame to CD8a linking and transmembrane domains (aa 123-191, Ref sequence ID NP_001759.3), and then to 4-1BB (CD137, aa 214-255, UniProt sequence ID Q07011) signaling domain and CD3 zeta signaling domain (CD247, aa 52-163, Ref sequence ID: NP_000725.1). CAR constructs sequences were cloned into a third generation lentiviral plasmid backbone (Lentigen Technology Inc., Gaithersburg, Md.). Lentiviral vector (LV) containing supernatants were generated by transient transfection of HEK 293T cells and vector pelleted by centrifugation of lentiviral vector-containing supernatants, and stored at −80° C.

(c) Primary T Cell Purification and Transduction

Human primary T cells from healthy volunteers were purified from whole blood or buffy coats (purchased from commercial provider with donor's written consent) using immunomagnetic bead selection of CD4+ and CD8+ cells according to manufacturer's protocol (Miltenyi Biotec, Bergisch Gladbach, Germany). T cells were cultivated in TexMACS™ medium supplemented with 200 IU/ml IL-2 at a density of 0.3 to 2×106 cells/ml, activated with CD3/CD28 MACS® GMP T Cell TransAct reagent (Miltenyi Biotec) and transduced on day 2 with lentiviral vectors encoding CAR constructs in the presence of 10 ug/ml protamine sulfate (Sigma-Aldrich, St. Louis, Mo.) overnight, and media exchanged on day 3. Cultures were propagated in TexMACS™ medium supplemented with 200 IU/ml IL-2 until harvest on day 8-13.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). Supernatants from co-cultures at E:T ratio of 10:1 were removed and analyzed by ELISA (eBioscience, San Diego, Calif.) for IFNγ and TNFα concentration.

(e) Flow Cytometric Analysis of CAR Surface Expression

For cell staining, half a million CAR T transduced cells were harvested from culture, washed two times in cold AutoMACS® buffer supplemented with 0.5% bovine serum albumin (Miltenyi Biotec), and CAR surface expression detected by staining with Protein L-biotin followed by streptavidin-PE conjugate (Jackson ImmunoResearch, West Grove, Pa.). Anti-CD4 antibody conjugated to VioBlue® fluorophore (Miltenyi Biotec) was used where indicated, as per vendors' protocol. Non-transduced cells were used as negative controls. Dead cells in all studies were excluded by 7AAD staining (BD Biosciences, San Jose, Calif.). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, Oreg.).

Results:

This example describes the creation of a CAR T cells targeting the tumor antigen CD123 for the treatment if AML and other CD123+ malignancies.

Each CAR was comprised of a human ScFv binder, CD8 hinge and transmembrane domain, 4-1BB co-stimulatory domain and CD3z activation domain (FIG. 1)

Table 1 below details the CAR123 constructs that were developed, designated by LTG numbers, and the ScFvs used in each construct.

| CAR construct LTG# | CD123 ScFv binder |
| --- | --- |
| 2074 | M12301 |
| 2075 | M12303 |
| 2076 | M12304 |
| 2077 | M12305 |
| 2078 | M12306 |
| 2079 | M12308 |
| 2080 | M12309 |
| 2081 | M12310 |
| 2082 | M12311 |
| 2083 | M12313 |
| 2084 | M12314 |
| 2085 | M12315 |
| 2086 | M12316 |
| 2087 | M12317 |
| 2088 | M12318 |

Schema of CD123 CAR design is shown in FIG. 1. Fully human ScFv binders targeting CD123 were linked in frame to CD8 hinge and transmembrane domain, 4-1BB costimulatory domain and CD3 zeta activation domain. CAR sequences were incorporated into a 3rd generation lentiviral vectors and applied to primary human T cells for transduction.

The surface expression of anti-CD123 CARs incorporating single chain fragment variable (ScFv) sequences, is shown in FIG. 2. The expression level for each ScFv-containing CAR was determined by flow cytometric analysis of LV-transduced T cells from healthy donors using Protein L-biotin, followed by streptavidin-PE. A subset of ScFv-based anti-CD123 CAR constructs were highly expressed in human primary T cells as detected by protein L, and as compared to non-transduced T cell controls (UTD), FIG. 2. These constructs included LTG ##2074, 2075, 2076, 2078, 2079, 2084, 2088.

As shown in FIG. 3, high cytolytic activity of the CD123 CARs was demonstrated for a subset of constructs analyzed. The non-transduced T cells (UTD), and GFP-transduced T cells (LTG1398) were used a s negative controls for CAR cytolytic function.

Human primary T cells were transduced with LV encoding CAR constructs (see Methods), then incubated for 18 hours with the MOLM-14, a CD123+ tumor line, or HEK293, a CD123-negative control line. Each target line was stably transduced with firefly luciferase, for luminescence based in vitro killing assays. MOLM-14 cells were lysed effectively by constructs LTG 2075, 2076, 2078, 2079, 2082, 2083, 2085, 2087, and 2088. However, CARs LTG ##2074, 2080, 2081, 2084, 2086 were not able to effectively lyse CD123+ MOLM-14 tumor cells, in concordance with relatively low expression of CAR LTG 2074, 2084 and 2087. The expression levels of LTG #2080, 2081 could not be detected. Notably, no killing function was detected for the negative control groups, UTD and GFP-transduced T cells LTG1398. These results demonstrate that the intensity of CAR lytic activity is dependent on CAR expression levels, and therefore is CAR-specific (FIG. 3). CD123-targeting CAR construct were then tested against a CD123-negative cell line, 293T, and no cytolytic activity above negative control level (T cells alone-UTD, or GFP-transduced T cells, LTG1398) was observed in any of the CD123 CAR constructs tested, despite dramatic cytolysis of CD123-positive cell line observed for a number of CAR123 constructs. This observation demonstrates that the cytolytic activity of CAR T cells is target-dependent. (FIG. 3).

The capacity of anti-CD123 CAR T cells for elaborating cytokines in response to antigen-expressing target cells was then evaluated (FIG. 4) Tumor lines positive for Cd123 expression MOLM-14 and KG-1a, or negative for CD123 expression, 293T, were co-incubated with CAR T cells incorporating CAR123 constructs LTG ##2074-2088, or negative untransduced T cells (UTD), or GFP-transduced T cells (LTG1398), at effector to target ratio of 10:1 overnight, and culture supernatants were analyzed by ELISA for IFN gamma and TNF alpha, CAR123 constructs LTG ##2076, 2078, and 2088 strongly induced cytokines in response to tumor cells, whereas the rest of CAR123 constructs tested, and the negative control (untransduced, UTD; GFP, LTG1398) yielded no appreciable cytokine induction. Importantly, CAR123 constructs LTG ##2076, 2078, and 2088 produced no cytokine secretion in the absence of tumor cells (CART alone group), which further confirms CAR specificity, and indicates a lack of tonic signaling by the tandem car.

Without being intended to limit to any particular mechanism of action, it is believed that possible reasons for the enhanced therapeutic function associated with the exemplary CD123 targeting CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or e) superior ability to engage with tumor antigen due to two distinct targeting domains present in each CAR molecule, or any combination thereof.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. A method of treating a subject with a B-cell cancer or a lymphoma, the method comprising administering to the subject a pharmaceutical composition comprising an anti-tumor effective amount of a population of autologous T-cells, wherein the autologous T-cells comprise a nucleic acid sequence that encodes a chimeric antigen receptor (CAR) and is operably linked to a promoter, wherein the CAR comprises at least one extracellular antigen binding domain comprising a CD 123 antigen binding domain comprising the amino acid sequence of SEQ ID NO: 78, 88, 92, 94, 100, 102, 106, 110, or 112, at least one linker or at least one spacer domain, at least one transmembrane domain, and at least one intracellular signaling domain thereby treating the B-cell cancer or the lymphoma in the subject.

2. The method of claim 1, wherein the at least one transmembrane domain comprises a transmembrane domain of the alpha, the beta or the zeta chain of a T-cell receptor, a CD8, a CD28, a CD3 epsilon, a CD45, a CD4, a CD5, a CD8, a CD9, a CD16, a CD22, a CD33, a CD37, a CD64, a CD80, a CD86, a CD134, a CD137, or CD154.

3. The method of claim 1, wherein the at least one extracellular antigen binding domain comprising the CD123 antigen binding domain, the at least one intracellular signaling domain, or both are connected to the at least one transmembrane domain by the at least one linker or the at least one spacer domain.

4. The method of claim 1, wherein the at least one linker or the at least one spacer domain is obtained from the extracellular domain of CD8, TNFRSF19, or CD28, and is linked to the at least one transmembrane domain.

5. The method of claim 1, wherein the at least one extracellular antigen binding domain comprising the CD123 antigen binding domain is preceded by a leader nucleotide sequence encoding a leader peptide.

6. The method of claim 1, wherein the at least one intracellular signaling domain further comprises a CD3 zeta intracellular domain.

7. The method of claim 1, wherein the at least one intracellular signaling domain comprises a costimulatory domain, a primary signaling domain, or any combination thereof.

8. The method of claim 7, wherein the at least one costimulatory domain comprises a functional signaling domain of OX40, CD70, CD27, CD28, CD5, ICAM-1, LFA-1 (CD11a/CD18), ICOS (CD278), DAP10, DAP12, or 4-1BB (CD137).

9. The method of claim 1, wherein the B-cell cancer is a hematological B-cell cancer.

10. The method of claim 1, wherein the B-cell cancer is chronic myelogenous leukemia (CML), chronic lymphocytic leukemia (CLL), or acute lymphoblastic B cell leukemia (B-ALL).

11. The method of claim 1, wherein the lymphoma is mantle cell lymphoma, non-Hodgkin's lymphoma or Hodgkin's lymphoma.

* * * * *

SEQUENCE LISTING

```
<160> NUMBER OF SEQ ID NOS: 112

<210> SEQ ID NO 1
<211> LENGTH: 729
<212> TYPE: DNA
<213> ORGANISM: Artificial Sequence
<220> FEATURE:
<223> OTHER INFORMATION: CD123 hScFv binder M12301

<400> SEQUENCE: 1
gaagtgcaac tcgtccaaag cggagctgaa gtgaagaaac caggcggatc cctgagactg      60
tcttgcgccg catcgggctt caccttctcc tcgtattcca tgaactgggt cagacaggcc     120
cctggaaagg gtctggaatg ggtgtcctcc atttcctcct cgtcgagcta catctactac     180
gccgactccg tgaaggggcg cttcacaatc tcccgggaca acgcgaagaa ctccctgtac     240
ctccaaatga actccctgag ggccgaggat actgccgtgt actactgcgc catcgagagc     300
tggggctccc tcgactattg gggccaggga accctggtca ccgtgtcatc cggcggtgga     360
ggatcgggtg gtggcggatc cggaggaggg ggatcccaga gcgtgctgac ccaacccccg     420
tcagtgtcag ccgcgcctgg acagaaggtc accatcagct gtagcggctc atcctccaat     480
atcggcgacg attacgtgtc ctggtaccag cagcttcctg gaaccgctcc caagctcctg     540
atctacgaca accacaagcg cccgtcggga attccggacc ggtttagcgg ttcaaagtcc     600
gggactagcg cgactctggg gattaccgga ctgcagacgg cgacgaagc cgattactac      660 tgcgggactt gggatgactc gcttagcgga gtggtgttcg gtggcgggac caagctcact     720
gtgttggga                                                              729
```

<210> SEQ ID NO 2
<211> LENGTH: 243
<212> TYPE: PRT
<213> ORGANISM: Artificial Sequence
<220> FEATURE:
<223> OTHER INFORMATION: CD123 hScFv binder M12301

<400> SEQUENCE: 2

```
Glu Val Gln Leu Val Gln Ser Gly Ala Glu Val Lys Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ile Glu Ser Trp Gly Ser Leu Asp Tyr Trp Gly Gln Gly Thr Leu
            100                 105                 110

Val Thr Val Ser Ser Gly Gly Gly Gly Ser Gly Gly Gly Ser Gly
        115                 120                 125

Gly Gly Gly Ser Gln Ser Val Leu Thr Gln Pro Pro Ser Val Ser Ala
    130                 135                 140

Ala Pro Gly Gln Lys Val Thr Ile Ser Cys Ser Gly Ser Ser Ser Asn
145                 150                 155                 160

Ile Gly Asp Asp Tyr Val Ser Trp Tyr Gln Gln Leu Pro Gly Thr Ala
                165                 170                 175

Pro Lys Leu Leu Ile Tyr Asp Asn His Lys Arg Pro Ser Gly Ile Pro
            180                 185                 190

Asp Arg Phe Ser Gly Ser Lys Ser Gly Thr Ser Ala Thr Leu Gly Ile
        195                 200                 205

Thr Gly Leu Gln Thr Gly Asp Glu Ala Asp Tyr Tyr Cys Gly Thr Trp
    210                 215                 220

Asp Asp Ser Leu Ser Gly Val Val Phe Gly Gly Gly Thr Lys Leu Thr
225                 230                 235                 240

Val Leu Gly
```

<210> SEQ ID NO 3
<211> LENGTH: 720
<212> TYPE: DNA
<213> ORGANISM: Artificial Sequence
<220> FEATURE:
<223> OTHER INFORMATION: CD123 hScFv binder M12303

<400> SEQUENCE: 3

```
gaagtgcaac tcgtcgaaac tggagccgaa gtgaaaaagc ctggagcgtc cgtcaaagtg    60
tcgtgcaagg cctccggcta caccttcacg acctactacg tgcactgggt cagacaggct   120
ccgggtcaag ggctggagtg gatgggcatc attaacccct ccggtggaag cacctcctat   180
gcgcaaaagt tccagggtcg cgtcaccatg actcgcgata cctccacttc cactgtgtac   240
atggaactga gctccctgag gtccgaggac accgccgtgt actactgcgc acgggatgga   300
ggcttgggcg gctacgaggc ttggggacag ggcaccctcg tgactgtgtc aagcggaggg   360
```

| | | |
|---|---|---|
| ggtggatccg gagggggagg atcaggcggt ggtggaagcg atatccagct tacccagtcg | 420 |
| ccttccgcgc tgtctgcatc ggccggcgac agagtgacaa ttacctgtca agccagccag | 480 |
| gacatctcca actatctgaa ctggtaccag cagaagcccg aaaggctcc gaagctgctg | 540 |
| atctacgacg ccagcaacct ggaacggggc gtgccatcac ggttctcggg atcagggtcg | 600 |
| ggcactgagt tcaccttcac catctcctcc ctccaacccg aggacattgc cacctactac | 660 |
| tgccagcagt acgacaacct cccgatcacc tttggacagg ggactcgcct ggaaatcaag | 720 |

<210> SEQ ID NO 4
<211> LENGTH: 240
<212> TYPE: PRT
<213> ORGANISM: Artificial Sequence
<220> FEATURE:
<223> OTHER INFORMATION: CD123 hScFv binder M12303

<400> SEQUENCE: 4

Glu Val Gln Leu Val Glu Thr Gly Ala Glu Val Lys Lys Pro Gly Ala
1               5                   10                  15
Ser Val Lys Val Ser Cys Lys Ala Ser Gly Tyr Thr Phe Thr Thr Tyr
            20                  25                  30
Tyr Val His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Gly Gly Leu Gly Gly Tyr Glu Ala Trp Gly Gln Gly Thr
            100                 105                 110
Leu Val Thr Val Ser Ser Gly Gly Gly Ser Gly Gly Gly Gly Ser
        115                 120                 125
Gly Gly Gly Gly Ser Asp Ile Gln Leu Thr Gln Ser Pro Ser Ala Leu
    130                 135                 140
Ser Ala Ser Ala Gly Asp Arg Val Thr Ile Thr Cys Gln Ala Ser Gln
145                 150                 155                 160
Asp Ile Ser Asn Tyr Leu Asn Trp Tyr Gln Gln Lys Pro Gly Lys Ala
                165                 170                 175
Pro Lys Leu Leu Ile Tyr Asp Ala Ser Asn Leu Glu Arg Gly Val Pro
            180                 185                 190
Ser Arg Phe Ser Gly Ser Gly Ser Gly Thr Glu Phe Thr Phe Thr Ile
        195                 200                 205
Ser Ser Leu Gln Pro Glu Asp Ile Ala Thr Tyr Tyr Cys Gln Gln Tyr
    210                 215                 220
Asp Asn Leu Pro Ile Thr Phe Gly Gln Gly Thr Arg Leu Glu Ile Lys
225                 230                 235                 240

<210> SEQ ID NO 5
<211> LENGTH: 759
<212> TYPE: DNA
<213> ORGANISM: Artificial Sequence
<220> FEATURE:
<223> OTHER INFORMATION: CD123 hScFv binder M12304

<400> SEQUENCE: 5
gaagtgcaat tggtccagag cggaggagga cttgtgaagc caggcggatc cctgagattg    60

```
tcatgcgccg catcggggtt cacctttcc tcctactcca tgaactgggt cagacaggcg      120
cccggaaagg gacttgaatg ggtgtcgtcc atttcctcct cctcgtccta catctactac      180
gccgactccg tgaagggccg cttcaccatc tcccgggaca acgccaagaa cagcctgtat      240
ctccaaatga actccctgcg ggccgaagat actgctgtgt attactgcgc tcgggacttc      300
ccgtacgact catcgggcta ttactcggac gcgttcgata tctggggcca gggaactatg      360
gtcaccgtca gctctggtgg cggtggttcc ggagggggtg gatccggtgg cggaggatca      420
gagattgtgc tgacccagtc cccgctgtca ctgcccgtga ctccgggaga gcctgcctcg      480
atctcgtgtc ggtccagcca gtccctgctg cactcgaatg gtacaactac ctcgattgg      540 tacctccaaa agcctgggca gtcaccccaa ctgctgatct acctcgggag caacagagcc      600
agcggagtgc ctgaccgctt tagcggttcc ggatccggca ccgacttcac cctgaaaatc      660
agccgggtgg aagccgagga tgtcggcgtg tactactgca tgcaggcact gcagactctg      720
gggtacacct tcggccaggg cacgaagctc gagatcaag                              759

<210> SEQ ID NO 6
<211> LENGTH: 253
<212> TYPE: PRT
<213> ORGANISM: Artificial Sequence
<220> FEATURE:
<223> OTHER INFORMATION: CD123 hScFv binder M12304

<400> SEQUENCE: 6

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Pro Tyr Asp Ser Gly Tyr Tyr Ser Asp Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Ile Val Leu
    130                 135                 140

Thr Gln Ser Pro Leu Ser Leu Pro Val Thr Pro Gly Glu Pro Ala Ser
145                 150                 155                 160

Ile Ser Cys Arg Ser Ser Gln Ser Leu Leu His Ser Asn Gly Tyr Asn
                165                 170                 175

Tyr Leu Asp Trp Tyr Leu Gln Lys Pro Gly Gln Ser Pro Gln Leu Leu
            180                 185                 190

Ile Tyr Leu Gly Ser Asn Arg Ala Ser Gly Val Pro Asp Arg Phe Ser
        195                 200                 205

Gly Ser Gly Ser Gly Thr Asp Phe Thr Leu Lys Ile Ser Arg Val Glu
    210                 215                 220

Ala Glu Asp Val Gly Val Tyr Tyr Cys Met Gln Ala Leu Gln Thr Leu
225                 230                 235                 240
```

Gly Tyr Thr Phe Gly Gln Gly Thr Lys Leu Glu Ile Lys
            245                 250

<210> SEQ ID NO 7
<211> LENGTH: 747
<212> TYPE: DNA
<213> ORGANISM: Artificial Sequence
<220> FEATURE:
<223> OTHER INFORMATION: CD123 hScFv binder M12305

<400> SEQUENCE: 7
caagtgcaac tcgtccaatc cggtgccgaa gtcaagaagc ctggttcctc cgtgaaagtg      60
tcgtgcaaag ccagcggcgg gacttttagc tcctacgcga tcagctgggt cagacaggcc     120
cctggacaag cctcgagtg gatgggcggc atcattccga ttttcggtac cgccaactac     180
gcccagaagt tccagggacg cgtgaccatt actaccgacg agagcacctc aaccgcatac     240
atggaactgt ccagcctgcg ctccgaggac acggctgtgt actattgcgc cagacgggga     300
tggggaggat tctcctccgg ctccgcattc gacatctggg gacagggcac tatggtcact     360
gtgtcatccg ggggaggagg atcaggcggt ggaggatccg gtggtggcgg atccaacttc     420
atgctgaccc agccccactc agtgtcggaa tcgcccggca acaccgtgac tatcagctgc     480
accggatcca gcgggaccat cggctctaat ttcgtgcagt ggtaccagca gtccccaggg     540
agagctccga ccctgttgat ctacgaggac acaaagcggc aagcggagt gccgcctaga      600 ttcgccggct ccgtggattc ctcgtccaac tcggcgtcgc tgaccatcag cggactcaag     660
actgaagatg aagccgacta ctactgtcag tcctacgact cgagcaactg ggtgtttggg     720
ggcgggacta agctgaccgt gcttgga                                          747

<210> SEQ ID NO 8
<211> LENGTH: 249
<212> TYPE: PRT
<213> ORGANISM: Artificial Sequence
<220> FEATURE:
<223> OTHER INFORMATION: CD123 hScFv binder M12305

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Trp Gly Gly Phe Ser Ser Gly Ser Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Ser Asn Phe Met Leu Thr Gln
    130                 135                 140

Pro His Ser Val Ser Glu Ser Pro Gly Asn Thr Val Thr Ile Ser Cys
145                 150                 155                 160

```
Thr Gly Ser Ser Gly Thr Ile Gly Ser Asn Phe Val Gln Trp Tyr Gln
            165                 170                 175

Gln Ser Pro Gly Arg Ala Pro Thr Leu Leu Ile Tyr Glu Asp Thr Lys
        180                 185                 190

Arg Pro Ser Gly Val Pro Pro Arg Phe Ala Gly Ser Val Asp Ser Ser
            195                 200                 205

Ser Asn Ser Ala Ser Leu Thr Ile Ser Gly Leu Lys Thr Glu Asp Glu
        210                 215                 220

Ala Asp Tyr Tyr Cys Gln Ser Tyr Asp Ser Ser Asn Trp Val Phe Gly
225                 230                 235                 240

Gly Gly Thr Lys Leu Thr Val Leu Gly
            245

<210> SEQ ID NO 9
<211> LENGTH: 735
<212> TYPE: DNA
<213> ORGANISM: Artificial Sequence
<220> FEATURE:
<223> OTHER INFORMATION: CD123 hScFv binder M12306

<400> SEQUENCE: 9
gaagtccaat tggtgcagag cggatccgaa cttaagaaac ctggcgcgag cgtgaaagtg      60
tcctgcaagg cctccggagg gactttctcg tcgtacgcca ttagctgggt ccgccaagct     120
cctggccaag gctggagtg atgggcggg attatcccca tcttcgggac tgcgaactac     180
gcccagaagt tcagggccg ggtcactatc accgccacg aatcaacctc gaccgcctac     240
atggaactgt cctcgcttcg gtccgaggat actgccgtgt actattgtgc ctcaacggcc     300
agacgcggat gggacaccgc tggtccgctc gattactggg ccagggaac cctcgtgacc     360 gtcagctccg gaggaggagg ctccggtggt ggaggatccg ggggtggtgg atccgacatc     420
caaatgaccc agtccccctc gtccctgagc gcctctgtgg gcgacagagt gacaattgca     480
tgcagggcct cacagactat ctcccgctac ctgaactggt accagcagaa gccaggaaag     540
gcccctaagc tgctcatcta cgctgcgtcc tcgctccaat ccggggtgtc ctcacggttt     600
tccggatcgg gttccggcac cgagttcacc ctgaccatca gcagcctgca gcccgaggac     660
ttcgcaacct acttctgcca gcaaacctac tccccgccga ttacgttcgg acaggggact     720
cggctggaaa tcaag                                                     735

<210> SEQ ID NO 10
<211> LENGTH: 245
<212> TYPE: PRT
<213> ORGANISM: Artificial Sequence
<220> FEATURE:
<223> OTHER INFORMATION: CD123 hScFv binder M12306

<400> SEQUENCE: 10

Glu Val Gln Leu Val Gln Ser Gly Ser Glu Leu Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
            85                  90                  95

Ala Ser Thr Ala Arg Arg Gly Trp Asp Thr Ala Gly Pro Leu Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Asp Ile Gln Met Thr Gln
130                 135                 140

Ser Pro Ser Ser Leu Ser Ala Ser Val Gly Asp Arg Val Thr Ile Ala
145                 150                 155                 160

Cys Arg Ala Ser Gln Thr Ile Ser Arg Tyr Leu Asn Trp Tyr Gln Gln
            165                 170                 175

Lys Pro Gly Lys Ala Pro Lys Leu Leu Ile Tyr Ala Ala Ser Ser Leu
            180                 185                 190

Gln Ser Gly Val Ser Ser Arg Phe Ser Gly Ser Gly Ser Gly Thr Glu
            195                 200                 205

Phe Thr Leu Thr Ile Ser Ser Leu Gln Pro Glu Asp Phe Ala Thr Tyr
            210                 215                 220

Phe Cys Gln Gln Thr Tyr Ser Pro Pro Ile Thr Phe Gly Gln Gly Thr
225                 230                 235                 240

Arg Leu Glu Ile Lys
            245

<210> SEQ ID NO 11
<211> LENGTH: 729
<212> TYPE: DNA
<213> ORGANISM: Artificial Sequence
<220> FEATURE:
<223> OTHER INFORMATION: CD123 hScFv binder M12308

<400> SEQUENCE: 11
gaagtgcaac tcgtcgaaac aggggcagaa gtgaaaaacc caggctcaag cgtgaaagtg      60
tcgtgcaagg cttcgggcgg aactctgtcc aactacgcca tctcctgggt ccgccaagct     120
ccgggaaagg gcctcgagtg gatgggcgga atcattccca ttttcgggac cgccaactac     180
gcgcaaaagt tccagggccg ggtcactatc accgcggacg aaagcaccag caccgcctac     240
atggaactgt cctccctgcg ctccgaggac actgccgtgt actattgcgc ccggaggtca     300
tcgtggtacc ccgagggctg cttccagcac tggggacagg gcactctcgt gaccgtgtcg     360
tcgggtggtg gtggatcagg aggggagga tccggaggag gcggaagcga tattcagctg     420
acccagtcac cgagctccct gtccgcctcc accggagaca gagtgaccat cacgtgtcgg     480
gcctcccaag ggatctcctc ctacctggcc tggtaccagc agaagcctgg aaaggcaccg     540
aagttgctga tctacgccgc gagcacccttt cagtccggag tgcctagccg cttctcgggt     600
tccggctctg gcactgactt cactctgacc attagctgcc tgcagtccga ggattttgcc     660
acctactact gccagcagta ctatagctac ccctgacct cggggcgg aaccaagctc     720
gacatcaag                                                             729

<210> SEQ ID NO 12
<211> LENGTH: 243
<212> TYPE: PRT
<213> ORGANISM: Artificial Sequence
<220> FEATURE:
<223> OTHER INFORMATION: CD123 hScFv binder M12308

<400> SEQUENCE: 12

Glu Val Gln Leu Val Glu Thr Gly Ala Glu Val Lys Asn Pro Gly Ser
1               5                   10                  15

Ser Val Lys Val Ser Cys Lys Ala Ser Gly Gly Thr Leu Ser Asn Tyr
                20                  25                  30

Ala Ile Ser Trp Val Arg Gln Ala Pro Gly Lys Gly Leu Glu Trp Met
            35                  40                  45

Gly Gly Ile Ile Pro Ile Phe Gly Thr Ala Asn Tyr Ala Gln Lys Phe
50                      55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Arg Ser Ser Trp Tyr Pro Glu Gly Cys Phe Gln His Trp Gly
            100                 105                 110

Gln Gly Thr Leu Val Thr Val Ser Gly Gly Gly Ser Gly Gly
        115                 120                 125

Gly Gly Ser Gly Gly Gly Ser Asp Ile Gln Leu Thr Gln Ser Pro
130                 135                 140

Ser Ser Leu Ser Ala Ser Thr Gly Asp Arg Val Thr Ile Thr Cys Arg
145                 150                 155                 160

Ala Ser Gln Gly Ile Ser Ser Tyr Leu Ala Trp Tyr Gln Gln Lys Pro
                165                 170                 175

Gly Lys Ala Pro Lys Leu Leu Ile Tyr Ala Ala Ser Thr Leu Gln Ser
            180                 185                 190

Gly Val Pro Ser Arg Phe Ser Gly Ser Gly Ser Gly Thr Asp Phe Thr
        195                 200                 205

Leu Thr Ile Ser Cys Leu Gln Ser Glu Asp Phe Ala Thr Tyr Tyr Cys
    210                 215                 220

Gln Gln Tyr Tyr Ser Tyr Pro Leu Thr Phe Gly Gly Thr Lys Leu
225                 230                 235                 240

Asp Ile Lys

<210> SEQ ID NO 13
<211> LENGTH: 66
<212> TYPE: DNA
<213> ORGANISM: Artificial Sequence
<220> FEATURE:
<223> OTHER INFORMATION: leader/signal peptide sequence

<400> SEQUENCE: 13
atgctgctgc tggtgaccag cctgctgctg tgcgaactgc cgcatccggc gtttctgctg    60
attccg    66

<210> SEQ ID NO 14
<211> LENGTH: 22
<212> TYPE: PRT
<213> ORGANISM: Artificial Sequence
<220> FEATURE:
<223> OTHER INFORMATION: leader/signal peptide sequence

<400> SEQUENCE: 14

Met Leu Leu Leu Val Thr Ser Leu Leu Leu Cys Glu Leu Pro His Pro
1               5                   10                  15

Ala Phe Leu Leu Ile Pro
            20

-continued

```
<210> SEQ ID NO 15
<211> LENGTH: 741
<212> TYPE: DNA
<213> ORGANISM: Artificial Sequence
<220> FEATURE:
<223> OTHER INFORMATION: CD123 hScFv binder M12309

<400> SEQUENCE: 15
gaagtccaat tggtgcagag cggagctgaa gtgaagaaac ctggcgcgac cgtgaagatc        60
tcgtgcaaag tgtccggcta cactttcacc gactactata tgcactgggt gcaacaggcg       120
ccgggaaagg gactggagtg gattggcctt gtggaccccg aagatggcga accatctac        180
gccgagaagt tccagggccg ggtcactatc accgcggaca cttccacgga caccgcctac       240
atggaactga gctccctgag atccgaggac accgccgtgt actactgcgc cactgcccca       300
ctggggaaa tcggcgcagc agtggactac tggggacagg gaactctcgt cactgtgtcc        360
agcggtggag gaggcagcgg tggtggaggc tccggtggtg gtggatccca tgtcattctg       420
actcagccgc cgtcagtgtc agccgccccct ggacaagagg tgtccatctc ctgttcgggg      480
tccgatgcca acattgggac caacttggtg tcgtggtacc agcacgtgcc tggaacagcc       540
cccaagctgc tcatctacga gaactcgaag aggccatccg gaattcccgc ccggttttca       600
tcgagccagt cagggaccctc cgctaccctg gctatcagcg ggctccagtc tgggatgaa       660
gcgatctact actgcctgac ctgggatcgc accctctccg gaaagatctt cggtggcggc       720
actcagctga ccgtgcttgg a                                                 741

<210> SEQ ID NO 16
<211> LENGTH: 247
<212> TYPE: PRT
<213> ORGANISM: Artificial Sequence
<220> FEATURE:
<223> OTHER INFORMATION: CD123 hScFv binder M12309

<400> SEQUENCE: 16

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Ile
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Pro Leu Gly Glu Val Gly Ala Ala Val Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser His Val Ile Leu Thr Gln Pro Pro
    130                 135                 140

Ser Val Ser Ala Ala Pro Gly Gln Glu Val Ser Ile Ser Cys Ser Gly
145                 150                 155                 160

Ser Asp Ala Asn Ile Gly Thr Asn Leu Val Ser Trp Tyr Gln His Val
                165                 170                 175

Pro Gly Thr Ala Pro Lys Leu Leu Ile Tyr Glu Asn Ser Lys Arg Pro
```

```
                  180                 185                 190
Ser Gly Ile Pro Ala Arg Phe Ser Ser Gln Ser Gly Thr Ser Ala
            195                 200                 205

Thr Leu Ala Ile Ser Gly Leu Gln Ser Gly Asp Glu Ala Ile Tyr Tyr
        210                 215                 220

Cys Leu Thr Trp Asp Arg Thr Leu Ser Gly Lys Ile Phe Gly Gly Gly
225                 230                 235                 240

Thr Gln Leu Thr Val Leu Gly
                245

<210> SEQ ID NO 17
<211> LENGTH: 744
<212> TYPE: DNA
<213> ORGANISM: Artificial Sequence
<220> FEATURE:
<223> OTHER INFORMATION: CD123 hScFv binder M12310

<400> SEQUENCE: 17
gaagtgcaac ttgtccaaag cggagccgaa gtgaagaagc caggatcctc cgtgaaagtg     60
tcttgcaaag catccggcgg cactttctcc tcctacgcca tctcctgggt cagacaggcg    120
cctggacagg gtctggagtg gatgggcatt atcaatccta gcggtggctc cacttcgtat    180
gcccagaagt tccagggtcg ggtcaccatg acccgggata cttcaactag caccgtgtac    240
atggaactct cctcgctgcg ctcggacgat accgccgtgt actactgtgc ccgcgagctg    300
ctctggtttg gagagctgga cacctacgga atggacgtct ggggacaggg gaccactgtg    360
acggtgtcgt caggaggcgg aggctcagga ggggtggtt ccgagggggg aggatccctc    420
ccggtgctga cccagccccc aagcgtcagc gtggctccgg aaagaccgc cgcatcaca    480 tgcggcggga caacatcgg ctccaagtcc gtgcattggt accagcagaa gcctggacaa    540
gcgccggtgc tggtcatcta cgacgactca gatcggccct ccggcattcc cgagcggttc    600
agcggctcca actcgggcaa cactgctact ctgaccatct cgagggtgga agcggggac    660 gaagcagatt actactgcca agtctgggac tccagctccg accacggggt gttcggcgga    720
ggaacccagc tgaccgtgtt ggga                                           744

<210> SEQ ID NO 18
<211> LENGTH: 248
<212> TYPE: PRT
<213> ORGANISM: Artificial Sequence
<220> FEATURE:
<223> OTHER INFORMATION: CD123 hScFv binder M12310

<400> SEQUENCE: 18

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Glu Leu Leu Trp Phe Gly Glu Leu Asp Thr Tyr Gly Met Asp
```

```
                100              105                110
Val Trp Gly Gln Gly Thr Thr Val Thr Val Ser Ser Gly Gly Gly
            115                 120                 125

Ser Gly Gly Gly Gly Ser Gly Gly Gly Ser Leu Pro Val Leu Thr
            130                 135                 140

Gln Pro Pro Ser Val Ser Val Ala Pro Gly Lys Thr Ala Arg Ile Thr
145                 150                 155                 160

Cys Gly Gly Asn Asn Ile Gly Ser Lys Ser Val His Trp Tyr Gln Gln
                165                 170                 175

Lys Pro Gly Gln Ala Pro Val Leu Val Ile Tyr Asp Asp Ser Asp Arg
            180                 185                 190

Pro Ser Gly Ile Pro Glu Arg Phe Ser Gly Ser Asn Ser Gly Asn Thr
            195                 200                 205

Ala Thr Leu Thr Ile Ser Arg Val Glu Ala Gly Asp Glu Ala Asp Tyr
            210                 215                 220

Tyr Cys Gln Val Trp Asp Ser Ser Ser Asp His Gly Val Phe Gly Gly
225                 230                 235                 240

Gly Thr Gln Leu Thr Val Leu Gly
                245

<210> SEQ ID NO 19
<211> LENGTH: 732
<212> TYPE: DNA
<213> ORGANISM: Artificial Sequence
<220> FEATURE:
<223> OTHER INFORMATION: CD123 hScFv binder M12311

<400> SEQUENCE: 19
gaagtgcaac tcgtccaatc tggtgccgaa gtcaagaagc tggctcaag  cgtgaaagtg      60 tcctgcaaag cgtcgggagg gaccttcagc tcctacgcca tttcctgggt ccgccaagca     120
ccaggacagg gcctggagtg gatgggcggc atcatcccga tcttcgggac tgccaactac     180
gcccagaagt tccaggggag agtgaccatt accgccgacg agtcgaccag cacggcctac     240
atggaactgt ccagcctgcg ctccgaggac actgccgtgt actactgcgc gagggccaga     300
ctcggtggag cgttcgacat ctggggacag ggcaccatgg tcaccgtgtc atccggtggc     360
ggaggatccg gtggtggcgg atcaggaggg ggaggatccc agtccgtgct gactcagcct     420
ccctccgtga gcgctgcacc gggacagaag gtcaccatct catgctcggg gggaagctcc     480
aacatcggga ccactacgt gtcctggtac aacagttgc ctggtgccgc tccaaagctg      540
ctgatctatg acgataacaa gcggccgtcc ggaatccccg accggttctc ggggtctaga     600
tccggaacca gcgcaactct cggcattacc ggactgcaga gcggcgatga ggccgactac     660
tactgtggca catgggactc gtcgctggct gcccacgtgt ttggcactgg caccaaggtc     720
accgtgcttg ga                                                         732

<210> SEQ ID NO 20
<211> LENGTH: 244
<212> TYPE: PRT
<213> ORGANISM: Artificial Sequence
<220> FEATURE:
<223> OTHER INFORMATION: CD123 hScFv binder M12311

<400> SEQUENCE: 20

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
            20                  25                  30
Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Arg Leu Gly Gly Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Ala Ala Pro Gly Gln Lys Val Thr Ile Ser Cys Ser Gly Gly Ser Ser
145                 150                 155                 160

Asn Ile Gly Asn His Tyr Val Ser Trp Tyr Gln Gln Leu Pro Gly Ala
                165                 170                 175

Ala Pro Lys Leu Leu Ile Tyr Asp Asp Asn Lys Arg Pro Ser Gly Ile
            180                 185                 190

Pro Asp Arg Phe Ser Gly Ser Arg Ser Gly Thr Ser Ala Thr Leu Gly
        195                 200                 205

Ile Thr Gly Leu Gln Ser Gly Asp Glu Ala Asp Tyr Tyr Cys Gly Thr
    210                 215                 220

Trp Asp Ser Ser Leu Ala Ala His Val Phe Gly Thr Gly Thr Lys Val
225                 230                 235                 240

Thr Val Leu Gly

<210> SEQ ID NO 21
<211> LENGTH: 747
<212> TYPE: DNA
<213> ORGANISM: Artificial Sequence
<220> FEATURE:
<223> OTHER INFORMATION: CD123 hScFv binder M12313

<400> SEQUENCE: 21
gaagtgcaac ttgtccagag cggagccgaa gtgaagaaac tggatcctc cgtcaaagtg     60 tcgtgcaagg cttcgggcgg aaccttctcc tcgtacgcga tctcatgggt cagacaggca    120
cccggacagg gactggagtg gatgggcggc atcattccca tcttcggcac cgctaattac    180
gcccagaagt ttcaggggag agtgaccatc accgccgacg agtccacctc cactgcctac    240
atggaactgt cctcactgag gtccgaggat actgccgtgt actactgcgc gtcgcaaaag    300
gggggtggat ggtccattga cgccttcgat atttgggac aggggacgat ggtcacagtg    360
tcatccggcg gtggtggatc cggtggtggc ggatccggag gaggaggcag ccagtccgtg    420
ctgacccagc cgcctagcgt gtcggccgca tctgggcagc gcgtgaccat tcctgttcc    480 gggtcctcgt ccaacatcgg caacaactac gcctcctggt accaacagct cccgggaatg    540 gccctaagc tgctgatcta cgaggacaac aagcggccat ccgggatctc agaccggttc    600
agcggatccc agtccggcac ttccgcgagc ctcgccatca ccggactgca ggctgaggac    660
gaagccgact actactgcca atcatatgac agctcgctca gcggcgatgt ggtgttcggc    720
ggtggcacta agctgaccgt gttggga                                       747
```

<210> SEQ ID NO 22
<211> LENGTH: 249
<212> TYPE: PRT
<213> ORGANISM: Artificial Sequence
<220> FEATURE:
<223> OTHER INFORMATION: CD123 hScFv binder M12313

<400> SEQUENCE: 22

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gln Lys Gly Gly Gly Trp Ser Ile Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Gln Ser Val Leu Thr Gln Pro
    130                 135                 140

Pro Ser Val Ser Ala Ala Ser Gly Gln Arg Val Thr Ile Ser Cys Ser
145                 150                 155                 160

Gly Ser Ser Ser Asn Ile Gly Asn Asn Tyr Ala Ser Trp Tyr Gln Gln
                165                 170                 175

Leu Pro Gly Met Ala Pro Lys Leu Leu Ile Tyr Glu Asp Asn Lys Arg
            180                 185                 190

Pro Ser Gly Ile Ser Asp Arg Phe Ser Gly Ser Gln Ser Gly Thr Ser
        195                 200                 205

Ala Ser Leu Ala Ile Thr Gly Leu Gln Ala Glu Asp Glu Ala Asp Tyr
    210                 215                 220

Tyr Cys Gln Ser Tyr Asp Ser Ser Leu Ser Gly Asp Val Val Phe Gly
225                 230                 235                 240

Gly Gly Thr Lys Leu Thr Val Leu Gly
                245

<210> SEQ ID NO 23
<211> LENGTH: 729
<212> TYPE: DNA
<213> ORGANISM: Artificial Sequence
<220> FEATURE:
<223> OTHER INFORMATION: CD123 hScFv binder M12314

<400> SEQUENCE: 23
gaagtccaac tcgtccaaag cggtgcagaa gtgaaaaagc caggctcctc agtgaaagtg      60
tcctgcaaag cctcgggggg aaccttctcc tcctacgcca tctcctgggt ccgccaagca     120
ccaggacagg gcctggagtg gatgggcggg atcattccga tcttcggcac cgccaactac     180
gcccagaagt ttcagggccg cgtgactatc accgccgacg agtccacctc cactgcgtac     240
atggaactgt ccagcctgcg gtccgaggac actgccgtgt attactgcgc gagagtcggt     300
tgctccgggg gatcgtgtta tcccgactac tggggacagg ggaccctcgt gaccgtgtcg     360

```
tcgggtggtg gtggaagcgg cggtggagga tccggtggag gaggcagcga aatcgtgctg    420
actcagtcgc cgtcctcgct ttccgcctcc gtgggagatc gcgtgaccat cacgtgtcag    480
gcttctcaag acattagcaa ctacctgaat tggtaccagc agaagcctgg aaaggctccg    540
aagctgctca tctacgacgc gtccaacctg gagacagggg tgccttcacg gttctcggga    600
agcggatccg gcaccgattt caccttcacc atttcaagcc tgcaacccga ggatattgcc    660
acctactact gccagcagta cgacaacctc ccctgactt tcgggggcgg cactaagttg    720
gacatcaag                                                            729
```

<210> SEQ ID NO 24
<211> LENGTH: 243
<212> TYPE: PRT
<213> ORGANISM: Artificial Sequence
<220> FEATURE:
<223> OTHER INFORMATION: CD123 hScFv binder M12314

<400> SEQUENCE: 24

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Cys Ser Gly Gly Ser Cys Tyr Pro Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Ser Glu Ile Val Leu Thr Gln Ser Pro
    130                 135                 140

Ser Ser Leu Ser Ala Ser Val Gly Asp Arg Val Thr Ile Thr Cys Gln
145                 150                 155                 160

Ala Ser Gln Asp Ile Ser Asn Tyr Leu Asn Trp Tyr Gln Gln Lys Pro
                165                 170                 175

Gly Lys Ala Pro Lys Leu Leu Ile Tyr Asp Ala Ser Asn Leu Glu Thr
            180                 185                 190

Gly Val Pro Ser Arg Phe Ser Gly Ser Gly Ser Gly Thr Asp Phe Thr
        195                 200                 205

Phe Thr Ile Ser Ser Leu Gln Pro Glu Asp Ile Ala Thr Tyr Tyr Cys
    210                 215                 220

Gln Gln Tyr Asp Asn Leu Pro Leu Thr Phe Gly Gly Gly Thr Lys Leu
225                 230                 235                 240

Asp Ile Lys
```

<210> SEQ ID NO 25
<211> LENGTH: 735
<212> TYPE: DNA
<213> ORGANISM: Artificial Sequence
<220> FEATURE:
<223> OTHER INFORMATION: CD123 hScFv binder M12315

<400> SEQUENCE: 25

```
caagtccagt tgcaacaatg gggagcaggc cttctgaaac cgtccgagac actgagcctg      60
acgtgcgccg tctatggcgg atcgttctcc ggatactact ggtcgtggat cagacagcct     120
ccgggaaagg gtctggaatg gatcggcgaa atcaaccaca gcggcagcac caattacaac     180
ccgtcactga agtcaagggt caccattagc gtggacactt ccaagaacca gttctccctg     240
aaactgtcga gcgtgaccgc tgccgatact gccgtgtact actgtgcccg cggccaagtc     300
aagtatagct caagcctcgg ctactggggc cagggaaccc tcgtgaccgt gtcctcgggt     360
ggaggaggct ccggtggtgg aggatccggt ggcggaggat cgcagtccgt gctgacccag     420
cctccctccg tgtctgctgc ccctgggcaa aaggtcacca tttcgtgctc cggctcatcg     480
tccaacatcg ggaacaactt tgtgtcctgg taccagcagc tgcccggtac tgccccaaag     540
ctgctgatct acgaggacaa caagcgccca tccggattc cggatcggtt cagcggatca     600
cggtccggaa ctagcgcgac cctggggatc accgggctcc agactggcga cgaagcggac     660
tactactgcg gaacttggga ctcctccttg ggggcctggg tgttcggcgg agggaccaag     720
ctcaccgtgc ttgga                                                    735
```

<210> SEQ ID NO 26  
<211> LENGTH: 245  
<212> TYPE: PRT  
<213> ORGANISM: Artificial Sequence  
<220> FEATURE:  
<223> OTHER INFORMATION: CD123 hScFv binder M12315

<400> SEQUENCE: 26

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gln Val Lys Tyr Ser Ser Leu Gly Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Ser
145                 150                 155                 160

Ser Asn Ile Gly Asn Asn Phe Val Ser Trp Tyr Gln Gln Leu Pro Gly
                165                 170                 175

Thr Ala Pro Lys Leu Leu Ile Tyr Glu Asp Asn Lys Arg Pro Ser Gly
            180                 185                 190

Ile Pro Asp Arg Phe Ser Gly Ser Arg Ser Gly Thr Ser Ala Thr Leu
        195                 200                 205

Gly Ile Thr Gly Leu Gln Thr Gly Asp Glu Ala Asp Tyr Tyr Cys Gly
```

```
                210               215               220
Thr Trp Asp Ser Ser Leu Gly Ala Trp Val Phe Gly Gly Gly Thr Lys
225                 230                 235                 240

Leu Thr Val Leu Gly
                245

<210> SEQ ID NO 27
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 27
atctacatct gggcgccctt ggccgggact tgtggggtcc ttctcctgtc actggttatc    60
accctttact gc                                                       72

<210> SEQ ID NO 28
<211> LENGTH: 22
<212> TYPE: PRT
<213> ORGANISM: Artificial Sequence
<220> FEATURE:
<223> OTHER INFORMATION: CD8 transmembrane domain

<400> SEQUENCE: 28

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 29
<211> LENGTH: 135
<212> TYPE: DNA
<213> ORGANISM: Artificial Sequence
<220> FEATURE:
<223> OTHER INFORMATION: CD8 hinge domain

<400> SEQUENCE: 29
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                   135

<210> SEQ ID NO 30
<211> LENGTH: 47
<212> TYPE: PRT
<213> ORGANISM: Artificial Sequence
<220> FEATURE:
<223> OTHER INFORMATION: CD8 hinge domain

<400> SEQUENCE: 30

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 31
<211> LENGTH: 42
<212> TYPE: PRT
<213> ORGANISM: Artificial Sequence
<220> FEATURE:
```

<223> OTHER INFORMATION: amino acid sequence of amino acid numbers 118
      to 178 hinge region of CD8.alpha

<400> SEQUENCE: 31

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 32
<211> LENGTH: 106
<212> TYPE: PRT
<213> ORGANISM: Artificial Sequence
<220> FEATURE:
<223> OTHER INFORMATION: Human IgG CL sequence

<400> SEQUENCE: 32

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 33
<211> LENGTH: 126
<212> TYPE: DNA
<213> ORGANISM: Artificial Sequence
<220> FEATURE:
<223> OTHER INFORMATION: signaling domain of 4-1BB

<400> SEQUENCE: 33
aaacggggca gaaagaaact cctgtatata ttcaaacaac catttatgag accagtacaa        60
actactcaag aggaagatgg ctgtagctgc cgatttccag aagaagaaga aggaggatgt       120
gaactg                                                                 126

<210> SEQ ID NO 34
<211> LENGTH: 42
<212> TYPE: PRT
<213> ORGANISM: Artificial Sequence
<220> FEATURE:
<223> OTHER INFORMATION: signaling domain of 4-1BB

<400> SEQUENCE: 34

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 35
<211> LENGTH: 336
<212> TYPE: DNA
<213> ORGANISM: Artificial Sequence
<220> FEATURE:
<223> OTHER INFORMATION: signaling domain of CD3-zeta

<400> SEQUENCE: 35

```
agagtgaagt tcagcaggag cgcagacgcc cccgcgtaca agcagggcca gaaccagctc    60
tataacgagc tcaatctagg acgaagagag gagtacgatg tttggacaa gagacgtggc    120 cgggaccctg agatggggg aaagccgaga aggaagaacc ctcaggaagg cctgtacaat    180
gaactgcaga aagataagat ggcggaggcc tacagtgaga ttgggatgaa aggcgagcgc    240 cggagggca aggggcacga tggcctttac cagggtctca gtacagccac caaggacacc    300
tacgacgccc ttcacatgca ggccctgccc cctcgc                             336
```

<210> SEQ ID NO 36
<211> LENGTH: 112
<212> TYPE: PRT
<213> ORGANISM: Artificial Sequence
<220> FEATURE:
<223> OTHER INFORMATION: CD3zeta

<400> SEQUENCE: 36

```
Arg Val Lys Phe Ser Arg Ser Ala Asp Ala Pro Ala Tyr Lys Gln Gly
  1               5                  10                  15

Gln Asn Gln Leu Tyr Asn Glu Leu Asn Leu Gly Arg Arg Glu Glu Tyr
             20                  25                  30

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 37
<211> LENGTH: 726
<212> TYPE: DNA
<213> ORGANISM: Artificial Sequence
<220> FEATURE:
<223> OTHER INFORMATION: ScFv CD 19

<400> SEQUENCE: 37

```
gacatccaga tgacacagac tacatcctcc ctgtctgcct ctctgggaga cagagtcacc    60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt ttgccaacag gtaatacgc ttccgtacac gttcggaggg    300
gggaccaagc tggagatcac aggtggcggt ggctcgggcg gtggtgggtc gggtggcggc    360
ggatctgagg tgaaactgca ggagtcagga cctggcctgg tggcgccctc acagagcctg    420
tccgtcacat gcactgtctc aggggtctca ttacccgact atggtgtaag ctggattcgc    480
```
cagcctccac gaaagggtct ggagtggctg ggagtaatat ggggtagtga aaccacatac    540
tataattcag ctctcaaatc cagactgacc atcatcaagg acaactccaa gagccaagtt    600
ttcttaaaaa tgaacagtct gcaaactgat gacacagcca tttactactg tgccaaacat    660
tattactacg gtggtagcta tgctatggac tactggggcc aaggaacctc agtcaccgtc    720
tcctca    726

```
<210> SEQ ID NO 38
<211> LENGTH: 242
<212> TYPE: PRT
<213> ORGANISM: Artificial Sequence
<220> FEATURE:
<223> OTHER INFORMATION: ScFv CD 19

<400> SEQUENCE: 38
```

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

```
<210> SEQ ID NO 39
<211> LENGTH: 66
<212> TYPE: DNA
<213> ORGANISM: Artificial Sequence
<220> FEATURE:
<223> OTHER INFORMATION: GMCSF leader peptide

<400> SEQUENCE: 39
```
atgctgctgc tggtgaccag cctgctgctg tgcgaactgc cgcatccggc gtttctgctg    60
attccg 66

<210> SEQ ID NO 40
<211> LENGTH: 22
<212> TYPE: PRT
<213> ORGANISM: Artificial Sequence
<220> FEATURE:
<223> OTHER INFORMATION: GMCSF leader peptide

<400> SEQUENCE: 40

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 41
<211> LENGTH: 85
<212> TYPE: DNA
<213> ORGANISM: Artificial Sequence
<220> FEATURE:
<223> OTHER INFORMATION: TNFRSF19 leader peptide

<400> SEQUENCE: 41
ggctctgaaa gtgctgttgg aacaagaaaa gaccttcttc accttgctcg tgttgctggg      60
gtacctgtcc tgcaaagtca cctgt      85

<210> SEQ ID NO 42
<211> LENGTH: 29
<212> TYPE: PRT
<213> ORGANISM: Artificial Sequence
<220> FEATURE:
<223> OTHER INFORMATION: TNFRSF19 leader peptide

<400> SEQUENCE: 42

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys
            20                  25

<210> SEQ ID NO 43
<211> LENGTH: 63
<212> TYPE: DNA
<213> ORGANISM: Artificial Sequence
<220> FEATURE:
<223> OTHER INFORMATION: CD8 alpha leader peptide

<400> SEQUENCE: 43
atggcgctgc cggtgaccgc gctgctgctg ccgctggcgc tgctgctgca tgcggcgcgc      60
ccg      63

<210> SEQ ID NO 44
<211> LENGTH: 21
<212> TYPE: PRT
<213> ORGANISM: Artificial Sequence
<220> FEATURE:
<223> OTHER INFORMATION: CD8 alpha leader peptide

<400> SEQUENCE: 44

Met Ala Leu Pro Val Thr Ala Leu Leu Leu Pro Leu Ala Leu Leu Leu
1               5                   10                  15

His Ala Ala Arg Pro
            20

<210> SEQ ID NO 45
<211> LENGTH: 123
<212> TYPE: DNA
<213> ORGANISM: Artificial Sequence
<220> FEATURE:
<223> OTHER INFORMATION: CD28 co-stimulatory domain

<400> SEQUENCE: 45

```
cggtcgaaga ggtccagact cttgcactcc gactacatga acatgactcc tagaaggccc      60
ggacccacta gaaagcacta ccagccgtac gcccctcctc gggatttcgc cgcataccgg     120
tcc                                                                    123
```

<210> SEQ ID NO 46
<211> LENGTH: 41
<212> TYPE: PRT
<213> ORGANISM: Artificial Sequence
<220> FEATURE:
<223> OTHER INFORMATION: CD28 co-stimulatory domain

<400> SEQUENCE: 46

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 47
<211> LENGTH: 336
<212> TYPE: DNA
<213> ORGANISM: Artificial Sequence
<220> FEATURE:
<223> OTHER INFORMATION: CD3 zeta activation domain

<400> SEQUENCE: 47

```
agagtgaagt tcagccgctc agccgatgca ccggcctacc agcagggaca gaaccagctc      60
tacaacgagc tcaacctggg tcggcgggaa gaatatgacg tgctggacaa acggcgcggc     120
agagatccgg agatggggg aaagccgagg aggaagaacc ctcaagaggg cctgtacaac      180
gaactgcaga aggacaagat ggcggaagcc tactccgaga tcggcatgaa gggagaacgc     240
cggagaggga aggtcatga cggactgtac cagggcctgt caactgccac taaggacact      300
tacgatgcgc tccatatgca agctttgccc ccgcgg                                336
```

<210> SEQ ID NO 48
<211> LENGTH: 112
<212> TYPE: PRT
<213> ORGANISM: Artificial Sequence
<220> FEATURE:
<223> OTHER INFORMATION: CD3 zeta activation domain

<400> SEQUENCE: 48

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60
```

```
Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 49
<211> LENGTH: 201
<212> TYPE: DNA
<213> ORGANISM: Artificial Sequence
<220> FEATURE:
<223> OTHER INFORMATION: TNFRSF19 hinge and transmembrane domain

<400> SEQUENCE: 49

```
gcggccgcgg tcggattcca agacatggaa tgcgtgccct gcggcgaccc gccacctcct      60
tacgagccgc actgcgcatc gaaggtcaac ctcgtgaaga tcgcgagcac cgcgtcctca     120
ccccgggata tgctctggc cgccgtgatt tgttccgcct ggccaccgt gcttctggcc      180 ctgctgatcc tctgtgtgat c                                               201
```

<210> SEQ ID NO 50
<211> LENGTH: 67
<212> TYPE: PRT
<213> ORGANISM: Artificial Sequence
<220> FEATURE:
<223> OTHER INFORMATION: TNFRSF19 hinge and transmembrane domain

<400> SEQUENCE: 50

```
Ala Ala Ala Val Gly Phe Gln Asp Met Glu Cys Val Pro Cys Gly Asp
  1               5                  10                  15

Pro Pro Pro Pro Tyr Glu Pro His Cys Ala Ser Lys Val Asn Leu Val
                 20                  25                  30

Lys Ile Ala Ser Thr Ala Ser Ser Pro Arg Asp Thr Ala Leu Ala Ala
             35                  40                  45

Val Ile Cys Ser Ala Leu Ala Thr Val Leu Leu Ala Leu Leu Ile Leu
         50                  55                  60

Cys Val Ile
 65
```

<210> SEQ ID NO 51
<211> LENGTH: 63
<212> TYPE: DNA
<213> ORGANISM: Artificial Sequence
<220> FEATURE:
<223> OTHER INFORMATION: TNFRSF19 transmembrane domain

<400> SEQUENCE: 51

```
gccgccgtga tttgttccgc cttggccacc gtgcttctgg ccctgctgat cctctgtgtg      60
atc                                                                   63
```

<210> SEQ ID NO 52
<211> LENGTH: 21
<212> TYPE: PRT
<213> ORGANISM: Artificial Sequence
<220> FEATURE:
<223> OTHER INFORMATION: TNFRSF19 transmembrane domain

<400> SEQUENCE: 52

```
Ala Ala Val Ile Cys Ser Ala Leu Ala Thr Val Leu Leu Ala Leu Leu
  1               5                  10                  15
```

Ile Leu Cys Val Ile
          20

<210> SEQ ID NO 53
<211> LENGTH: 138
<212> TYPE: DNA
<213> ORGANISM: Artificial Sequence
<220> FEATURE:
<223> OTHER INFORMATION: TNFRSF19 hinge domain

<400> SEQUENCE: 53
gcggccgcgg tcggattcca agacatggaa tgcgtgccct gcggcgaccc gccacctcct        60
tacgagccgc actgcgcatc gaaggtcaac ctcgtgaaga tcgcgagcac cgcgtcctca       120
ccccgggata ctgctctg                                                    138

<210> SEQ ID NO 54
<211> LENGTH: 46
<212> TYPE: PRT
<213> ORGANISM: Artificial Sequence
<220> FEATURE:
<223> OTHER INFORMATION: TNFRSF19 hinge domain

<400> SEQUENCE: 54

Ala Ala Ala Val Gly Phe Gln Asp Met Glu Cys Val Pro Cys Gly Asp
1               5                   10                  15

Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu
        35                  40                  45

<210> SEQ ID NO 55
<211> LENGTH: 80
<212> TYPE: DNA
<213> ORGANISM: Artificial Sequence
<220> FEATURE:
<223> OTHER INFORMATION: truncated TNFRSF19 hinge domain

<400> SEQUENCE: 55
tacgagcctc actgcgccag caaagtcaac ttggtgaaga tcgcgagcac tgcctcgtcc        60
cctcgggaca ctgctctggc                                                   80

<210> SEQ ID NO 56
<211> LENGTH: 26
<212> TYPE: PRT
<213> ORGANISM: Artificial Sequence
<220> FEATURE:
<223> OTHER INFORMATION: truncated TNFRSF19 hinge domain

<400> SEQUENCE: 56

Tyr Glu Pro His Cys Ala Ser Lys Val Asn Leu Val Lys Ile Ala Ser
1               5                   10                  15

Thr Ala Ser Ser Pro Arg Asp Thr Ala Leu
            20                  25

<210> SEQ ID NO 57
<211> LENGTH: 222
<212> TYPE: DNA
<213> ORGANISM: Artificial Sequence
<220> FEATURE:
<223> OTHER INFORMATION: CD8a hinge domain fused to TNFRSF19
      transmembrane domain

<400> SEQUENCE: 57

```
gcggccgcgc cgcccctcg gccccgact cctgcccga cgatcgcttc ccaacctctc    60
tcgctgcgcc cggaagcatg ccggcccgcc gccggtggcg ctgtccacac tcgcggactg   120
gactttgata ccgcactggc ggccgtgatc tgtagcgccc tggccaccgt gctgctggcg   180
ctgctcatcc tttgcgtgat ctactgcaag cggcagccta gg                      222
```

```
<210> SEQ ID NO 58
<211> LENGTH: 74
<212> TYPE: PRT
<213> ORGANISM: Artificial Sequence
<220> FEATURE:
<223> OTHER INFORMATION: CD8a hinge domain fused to TNFRSF19
      transmembrane domain

<400> SEQUENCE: 58
```

Ala Ala Ala Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Asp Thr Ala Leu Ala Ala
        35                  40                  45

Val Ile Cys Ser Ala Leu Ala Thr Val Leu Leu Ala Leu Leu Ile Leu
    50                  55                  60

Cys Val Ile Tyr Cys Lys Arg Gln Pro Arg
65                  70

```
<210> SEQ ID NO 59
<211> LENGTH: 123
<212> TYPE: DNA
<213> ORGANISM: Artificial Sequence
<220> FEATURE:
<223> OTHER INFORMATION: CD28 co-stimulatory domain

<400> SEQUENCE: 59
cggtcgaaga ggtccagact cttgcactcc gactacatga acatgactcc tagaaggccc    60
ggacccacta gaaagcacta ccagccgtac gcccctcctc gggatttcgc cgcataccgg   120
tcc                                                                 123
```

```
<210> SEQ ID NO 60
<211> LENGTH: 41
<212> TYPE: PRT
<213> ORGANISM: Artificial Sequence
<220> FEATURE:
<223> OTHER INFORMATION: CD28 co-stimulatory domain

<400> SEQUENCE: 60
```

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

```
<210> SEQ ID NO 61
<211> LENGTH: 336
<212> TYPE: DNA
<213> ORGANISM: Artificial Sequence
<220> FEATURE:
<223> OTHER INFORMATION: CD3 zeta version 2

<400> SEQUENCE: 61
```

```
cgcgtgaaat ttagccgcag cgcggatgcg ccggcgtatc agcagggcca gaaccagctg      60
tataacgaac tgaacctggg ccgccgcgaa gaatatgatg tgctggataa acgccgcggc     120
cgcgatccgg aaatgggcgg caaaccgcgc cgcaaaaacc cgcaggaagg cctgtataac     180
gaactgcaga agataaaat ggcggaagcg tatagcgaaa ttggcatgaa aggcgaacgc     240
cgccgcggca aaggccatga tggcctgtat cagggcctga gcaccgcgac caaagatacc     300
tatgatgcgc tgcatatgca ggcgctgccg ccgcgc                               336
```

```
<210> SEQ ID NO 62
<211> LENGTH: 112
<212> TYPE: PRT
<213> ORGANISM: Artificial Sequence
<220> FEATURE:
<223> OTHER INFORMATION: CD3 zeta version 2

<400> SEQUENCE: 62

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 63
<211> LENGTH: 93
<212> TYPE: DNA
<213> ORGANISM: Artificial Sequence
<220> FEATURE:
<223> OTHER INFORMATION: Furin P2A Furin

<400> SEQUENCE: 63
cgcgcgaaac gcagcggcag cggcgcgacc aactttagcc tgctgaaaca ggcgggcgat      60
gtggaagaaa acccgggccc gcgagcaaag agg                                  93
```

```
<210> SEQ ID NO 64
<211> LENGTH: 31
<212> TYPE: PRT
<213> ORGANISM: Artificial Sequence
<220> FEATURE:
<223> OTHER INFORMATION: Furin P2A Furin

<400> SEQUENCE: 64

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro Arg Ala Lys Arg
            20                  25                  30
```

```
<210> SEQ ID NO 65
<211> LENGTH: 78
<212> TYPE: DNA
<213> ORGANISM: Artificial Sequence
<220> FEATURE:
```

<223> OTHER INFORMATION: Furin T2A

<400> SEQUENCE: 65

```
agagctaaac gctctgggtc tggtgaagga cgaggtagcc ttcttacgtg cggagacgtg    60
gaggaaaacc caggaccc                                                  78
```

<210> SEQ ID NO 66
<211> LENGTH: 26
<212> TYPE: PRT
<213> ORGANISM: Artificial Sequence
<220> FEATURE:
<223> OTHER INFORMATION: Furin T2A

<400> SEQUENCE: 66

```
Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25
```

<210> SEQ ID NO 67
<211> LENGTH: 1005
<212> TYPE: DNA
<213> ORGANISM: Artificial Sequence
<220> FEATURE:
<223> OTHER INFORMATION: truncated EGFR (tEGFR) tag

<400> SEQUENCE: 67

```
aggaaggttt gcaatggaat cggtataggg gagtttaagg attcacttag cataaacgct    60
actaatatta aacacttcaa aaactgtacg agtataagtg gagatcttca cattttgccg   120
gttgcattcc gaggcgattc attcacccac acgccaccgc ttgacccaca agaattggat   180
attcttaaaa ccgttaaaga aataacgggg ttttgctca ttcaagcgtg gccagaaaat    240
cgcactgacc tccatgcttt cgagaacctg gagattataa gaggacgaac taagcagcat   300
ggtcaattct cccttgctgt ggtcagcctg aacatcacca gtcttggttt gcggtccctc   360
aaggaaattt cagatggaga tgtcatcata agcggcaaca gaatttgtg ctatgcaaat    420 accataaact ggaaaaaact gtttggcact tccggccaga aaccaagat tatttcaaat    480 cggggtgaga acagctgcaa agccaccggc caggtttgtc atgccttgtg ctctccggaa   540
ggctgttggg ggccagaacc cagggactgc gtcagttgca gaaacgtctc aagaggccgc   600
gaatgcgttg acaagtgtaa cctccttgag ggtgagccac gagagtttgt tgagaacagc   660
gagtgtatac aatgtcaccc tgaatgtttg ccccaggcta tgaatataac ctgcacaggc   720
cgcgggcctg ataactgcat ccagtgtgct cattacatag atggacctca ctgtgtgaaa   780
acctgcccgg ccggagttat gggagaaaac aacactctgg tgtggaaata cgctgatgca   840
ggccacgtgt gccacctttg tcacccgaat tgtacatatg gtgtaccgg tcctggactt    900 gaaggttgcc ctaccaatgg ccctaaaata cccagtatcg caactggcat ggtaggcgct   960
cttctcttgc tcttggtagt tgctctcggc ataggtcttt ttatg                 1005
```

<210> SEQ ID NO 68
<211> LENGTH: 335
<212> TYPE: PRT
<213> ORGANISM: Artificial Sequence
<220> FEATURE:
<223> OTHER INFORMATION: truncated EGFR (tEGFR) tag

<400> SEQUENCE: 68

Arg Lys Val Cys Asn Gly Ile Gly Ile Gly Glu Phe Lys Asp Ser Leu

```
            1               5                   10                  15
        Ser Ile Asn Ala Thr Asn Ile Lys His Phe Lys Asn Cys Thr Ser Ile
                        20                  25                  30

Ser Gly Asp Leu His Ile Leu Pro Val Ala Phe Arg Gly Asp Ser Phe
                        35                  40                  45

Thr His Thr Pro Pro Leu Asp Pro Gln Glu Leu Asp Ile Leu Lys Thr
                        50                  55                  60

Val Lys Glu Ile Thr Gly Phe Leu Leu Ile Gln Ala Trp Pro Glu Asn
        65                  70                  75                  80

Arg Thr Asp Leu His Ala Phe Glu Asn Leu Glu Ile Ile Arg Gly Arg
                            85                  90                  95

Thr Lys Gln His Gly Gln Phe Ser Leu Ala Val Val Ser Leu Asn Ile
                        100                 105                 110

Thr Ser Leu Gly Leu Arg Ser Leu Lys Glu Ile Ser Asp Gly Asp Val
                        115                 120                 125

Ile Ile Ser Gly Asn Lys Asn Leu Cys Tyr Ala Asn Thr Ile Asn Trp
                        130                 135                 140

Lys Lys Leu Phe Gly Thr Ser Gly Gln Lys Thr Lys Ile Ile Ser Asn
        145                 150                 155                 160

Arg Gly Glu Asn Ser Cys Lys Ala Thr Gly Gln Val Cys His Ala Leu
                            165                 170                 175

Cys Ser Pro Glu Gly Cys Trp Gly Pro Glu Pro Arg Asp Cys Val Ser
                        180                 185                 190

Cys Arg Asn Val Ser Arg Gly Arg Glu Cys Val Asp Lys Cys Asn Leu
                        195                 200                 205

Leu Glu Gly Glu Pro Arg Glu Phe Val Glu Asn Ser Glu Cys Ile Gln
        210                 215                 220

Cys His Pro Glu Cys Leu Pro Gln Ala Met Asn Ile Thr Cys Thr Gly
        225                 230                 235                 240

Arg Gly Pro Asp Asn Cys Ile Gln Cys Ala His Tyr Ile Asp Gly Pro
                            245                 250                 255

His Cys Val Lys Thr Cys Pro Ala Gly Val Met Gly Glu Asn Asn Thr
                        260                 265                 270

Leu Val Trp Lys Tyr Ala Asp Ala Gly His Val Cys His Leu Cys His
                        275                 280                 285

Pro Asn Cys Thr Tyr Gly Cys Thr Gly Pro Gly Leu Glu Gly Cys Pro
                        290                 295                 300

Thr Asn Gly Pro Lys Ile Pro Ser Ile Ala Thr Gly Met Val Gly Ala
        305                 310                 315                 320

Leu Leu Leu Leu Leu Val Val Ala Leu Gly Ile Gly Leu Phe Met
                            325                 330                 335

<210> SEQ ID NO 69
<211> LENGTH: 717
<212> TYPE: DNA
<213> ORGANISM: Artificial Sequence
<220> FEATURE:
<223> OTHER INFORMATION: CD123 hScFv binder M12316

<400> SEQUENCE: 69
gaagtgcagt tggtggagag cggtggagga cttgtgcaac tggtggatc cctgagattg     60 tcgtgcgcag cttcagggtt caccttctcc tcctacgcca tgcactgggt ccgccaagca    120
ccaggaaagg gcctggaatg ggtcagctcc atctcctcgt cgtcctcgta catctactat    180
gccgactccg tgaagggccg cttcaccatt agccgggaca actcaaagaa cactctgtac    240
```

```
cttcaaatga actccctgcg ggctgaagat accgccgtgt actactgcgc gagggattgg      300
gatgacgcgt tcgacatttg gggccagggg actaccgtca ccgtgtcgtc gggtggagga      360
ggatccgggg gtggaggatc gggagggggt ggaagcgaca ttcagatgac tcagagcccg      420 tcctcccctgt cggcctcagt gggcgacaga gtgaccatca cctgtcaagc cagccaggac      480
atctcaaact acctgaactg gtaccagcag aagcccggaa aggcccctaa gctgctcatc      540
tacgacgcct ccaacctgga gactggagtg ccctcacggt tttccggctc tggaagcggc      600
accgatttca ccttcacgat ctcctccctg caaccggaag atatcgcgac ctactactgc      660
cagcagtatg acaatctccc gctcaccttc ggtggcggca ctaagctcga gatcaaa        717
```

<210> SEQ ID NO 70
<211> LENGTH: 239
<212> TYPE: PRT
<213> ORGANISM: Artificial Sequence
<220> FEATURE:
<223> OTHER INFORMATION: CD123 hScFv binder M12316

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Asp Asp Ala Phe Asp Ile Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Gln Ala Ser Gln Asp
145                 150                 155                 160

Ile Ser Asn Tyr Leu Asn Trp Tyr Gln Gln Lys Pro Gly Lys Ala Pro
                165                 170                 175

Lys Leu Leu Ile Tyr Asp Ala Ser Asn Leu Glu Thr Gly Val Pro Ser
            180                 185                 190

Arg Phe Ser Gly Ser Gly Ser Gly Thr Asp Phe Thr Phe Thr Ile Ser
        195                 200                 205

Ser Leu Gln Pro Glu Asp Ile Ala Thr Tyr Tyr Cys Gln Gln Tyr Asp
    210                 215                 220

Asn Leu Pro Leu Thr Phe Gly Gly Gly Thr Lys Leu Glu Ile Lys
225                 230                 235
```

<210> SEQ ID NO 71
<211> LENGTH: 723
<212> TYPE: DNA
<213> ORGANISM: Artificial Sequence
<220> FEATURE:
<223> OTHER INFORMATION: CD123 hScFv binder M12317

<400> SEQUENCE: 71

```
caagtccaac tcgtcgaaac tggtggtggc ctcgtgaagc tggaggatcc cctgcgcctt      60
tcctgtgccg cttccggctt tactttctcg tcgtactcca tgaactgggt cagacaggct     120
cccgaaaggg cctggaatg ggtgtcctcc atctcgtcct catcctccta catctattac      180
gcggactccg tgaagggcag attcaccatt tcccgggaca cgccaagaa cagcttgtac      240
ctccaaatga actccctgcg ggcagaggac accgccgtgt actactgcgc gagggatggg     300
gatttctgga gcggagccat cgactactgg ggccagggaa ctctcgtgac cgtcagctcc     360
ggtggtggtg aagcggagg cggaggttct ggggggggag gatcagacat tcagctgacc      420
cagtcgccat cctccctgag cgcctcagtg ggggaccgcg tgactattac atgccaggcc     480
tcccaagata tctcgaacta cctgaactgg tatcagcaga agcctggaaa gccccgaag      540
ctgttgatct acgatgccag caacctggag actggggtgc cttcccggtt ctcgggatca     600
ggctcgggca ccgatttcac cttcacgatc agcagcctgc agcccgagga cattgcaacc     660
tactactgcc agcagtacga caatctgccg cttttgggg gaggcaccaa gctggaaatc      720
aaa                                                                    723
```

<210> SEQ ID NO 72
<211> LENGTH: 241
<212> TYPE: PRT
<213> ORGANISM: Artificial Sequence
<220> FEATURE:
<223> OTHER INFORMATION: CD123 hScFv binder M12317

<400> SEQUENCE: 72

```
Gln Val Gln Leu Val Glu Thr Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asp Phe Trp Ser Gly Ala Ile Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Leu Thr Gln Ser Pro Ser
    130                 135                 140

Ser Leu Ser Ala Ser Val Gly Asp Arg Val Thr Ile Thr Cys Gln Ala
145                 150                 155                 160

Ser Gln Asp Ile Ser Asn Tyr Leu Asn Trp Tyr Gln Gln Lys Pro Gly
                165                 170                 175

Lys Ala Pro Lys Leu Leu Ile Tyr Asp Ala Ser Asn Leu Glu Thr Gly
            180                 185                 190

Val Pro Ser Arg Phe Ser Gly Ser Gly Ser Gly Thr Asp Phe Thr Phe
        195                 200                 205

Thr Ile Ser Ser Leu Gln Pro Glu Asp Ile Ala Thr Tyr Tyr Cys Gln
```

Gln Tyr Asp Asn Leu Pro Leu Phe Gly Gly Gly Thr Lys Leu Glu Ile
225                 230                 235                 240

Lys

<210> SEQ ID NO 73
<211> LENGTH: 723
<212> TYPE: DNA
<213> ORGANISM: Artificial Sequence
<220> FEATURE:
<223> OTHER INFORMATION: CD123 hScFv binder  M12318

<400> SEQUENCE: 73

```
gaggtgcaat tggtgcagtc aggtggtgga gtggtgcagc caggaagatc ccttagactc    60
tcgtgtgcgg cgtcaggctt taccttctcc tcgtactcca tgaactgggt cagacaggca   120
ccgggaaagg gactggaatg ggtgtcctcc atctcgtcct cctcctccta catctactac   180
gccgatagcg tgaagggccg gttcaccatt tcgcgcgaca cgccaagaa caccctgtac    240
ctccaaatga attcgctgcg ggccgaagat accgctgtct attactgcgc ccgcgacaac   300
tggggctcgc tggactattg gggccaggga accctcgtca ccgtgtcaag cggagggggt   360
ggatccggag gcggaggatc cggtggaggg ggaagcgaca ttcagatgac tcagagcccg   420
tcctcccctgt ctgcctccgt gggggatcgc gtgaccatca catgccaggc ctcacaagac   480
atcagcaatt acctgaactg gtaccagcag aagcctggaa aggcccccaa gctgctgatc   540
tacgatgcca gcaacctgga gactggggtg ccttcaaggt tctccggttc cggaagcggc   600
actgacttca ccttcactat ctcgagcctg caacccgagg acattgccac ctactactgc   660
cagcagtacg acaaccttcc gcacatgtac acgttcggcc agggcaccaa gctcgaaatc   720
aaa                                                                  723
```

<210> SEQ ID NO 74
<211> LENGTH: 241
<212> TYPE: PRT
<213> ORGANISM: Artificial Sequence
<220> FEATURE:
<223> OTHER INFORMATION: CD123 hScFv binder M12318

<400> SEQUENCE: 74

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Gly Ser Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
    130                 135                 140

```
Ala Ser Val Gly Asp Arg Val Thr Ile Thr Cys Gln Ala Ser Gln Asp
145                 150                 155                 160

Ile Ser Asn Tyr Leu Asn Trp Tyr Gln Gln Lys Pro Gly Lys Ala Pro
                165                 170                 175

Lys Leu Leu Ile Tyr Asp Ala Ser Asn Leu Glu Thr Gly Val Pro Ser
            180                 185                 190

Arg Phe Ser Gly Ser Gly Ser Gly Thr Asp Phe Thr Phe Thr Ile Ser
        195                 200                 205

Ser Leu Gln Pro Glu Asp Ile Ala Thr Tyr Tyr Cys Gln Gln Tyr Asp
    210                 215                 220

Asn Leu Pro His Met Tyr Thr Phe Gly Gln Gly Thr Lys Leu Glu Ile
225                 230                 235                 240

Lys
```

<210> SEQ ID NO 75
<211> LENGTH: 1473
<212> TYPE: DNA
<213> ORGANISM: Artificial Sequence
<220> FEATURE:
<223> OTHER INFORMATION: LTG 2074 (hScFv aCD123 CD8 TM 4-1BB CD3 zeta)

<400> SEQUENCE: 75

```
atgctgctgc tggtgaccag cctgctgctg tgcgaactgc cgcatccggc gtttctgctg    60
attccggaag tgcaactcgt ccaaagcgga gctgaagtga agaaaccagg cggatccctg   120
agactgtctt gcgccgcatc gggcttcacc ttctcctcgt attccatgaa ctgggtcaga   180
caggcccctg gaaagggtct ggaatgggtg tcctccattt cctcctcgtc gagctacatc   240
tactacgccg actccgtgaa ggggcgcttc acaatctccc gggacaacgc gaagaactcc   300
ctgtacctcc aaatgaactc cctgagggcc gaggatactg ccgtgtacta ctgcgccatc   360
gagagctggg gctccctcga ctattggggc cagggaaccc tggtcaccgt gtcatccggc   420
ggtggaggat cgggtggtgg cggatccgga ggaggggat cccagagcgt gctgacccaa   480
ccccgtcag tgtcagccgc gcctggacag aaggtcacca tcagctgtag cggctcatcc   540
tccaatatcg gcgacgatta cgtgtcctgg taccagcagc ttcctggaac cgctcccaag   600
ctcctgatct acgacaacca caagcgcccg tcgggaattc cggaccggtt tagcggttca   660
aagtccggga ctagcgcgac tctggggatt accggactgc agacgggcga cgaagccgat   720
tactactgcg ggacttggga tgactcgctt agcggagtgg tgttcggtgg cgggaccaag   780
ctcactgtgt tgggagcggc cgcaactacc accctgccc tcggccgcc gactccggcc   840
ccaaccatcg caagccaacc cctctccttg cgccccgaag cttgccgccc ggccgcgggt   900
ggagccgtgc atacccgggg gctggacttt gcctgcgata tctacatttg gcccccgctg   960
gccggcactt gcggcgtgct cctgctgtcg ctggtcatca ccctttactg caagagggggc  1020
cggaagaagc tgctttacat cttcaagcag ccgttcatgc ggcccgtgca cgacgactcag 1080
gaagaggacg gatgctcgtg cagattccct gaggaggaag aggggggatg cgaactgcgc  1140
gtcaagttct caccggtccgc cgacgccccc gcatatcaac agggccagaa tcagctctac  1200
aacgagctga acctgggaag agagaggag tacgacgtgc tggacaagcg acgcggacgc   1260
gacccggaga tggggggaa accacggcgg aaaaaccctc aggaaggact gtacaacgaa   1320
ctccagaaag acaagatggc ggaagcctac tcagaaatcg gatgaaggg agagcggagg   1380
aggggaaagg gtcacgacgg gctgtaccag ggactgagca ccgccactaa ggatacctac   1440
```
gatgccttgc atatgcaagc actcccaccc cgg                    1473

<210> SEQ ID NO 76
<211> LENGTH: 491
<212> TYPE: PRT
<213> ORGANISM: Artificial Sequence
<220> FEATURE:
<223> OTHER INFORMATION: LTG 2074 (hScFv aCD123 CD8 TM 4-1BB CD3 zeta)

<400> SEQUENCE: 76

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Gly Ser Leu Arg Leu Ser Cys Ala Ala Ser Gly
        35                  40                  45

Phe Thr Phe Ser Ser Tyr Ser Met Asn Trp Val Arg Gln Ala Pro Gly
    50                  55                  60

Lys Gly Leu Glu Trp Val Ser Ser Ile Ser Ser Ser Ser Tyr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Ile Glu Ser Trp Gly Ser Leu Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Gln Ser Val Leu Thr Gln
145                 150                 155                 160

Pro Pro Ser Val Ser Ala Ala Pro Gly Gln Lys Val Thr Ile Ser Cys
                165                 170                 175

Ser Gly Ser Ser Ser Asn Ile Gly Asp Asp Tyr Val Ser Trp Tyr Gln
            180                 185                 190

Gln Leu Pro Gly Thr Ala Pro Lys Leu Leu Ile Tyr Asp Asn His Lys
        195                 200                 205

Arg Pro Ser Gly Ile Pro Asp Arg Phe Ser Gly Ser Lys Ser Gly Thr
    210                 215                 220

Ser Ala Thr Leu Gly Ile Thr Gly Leu Gln Thr Gly Asp Glu Ala Asp
225                 230                 235                 240

Tyr Tyr Cys Gly Thr Trp Asp Asp Ser Leu Ser Gly Val Val Phe Gly
                245                 250                 255

Gly Gly Thr Lys Leu Thr Val Leu Gly Ala Ala Ala Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
```

```
                355                 360                 365
Phe Pro Glu Glu Glu Gly Gly Cys Glu Leu Arg Val Lys Phe Ser
        370                 375                 380
Arg Ser Ala Asp Ala Pro Ala Tyr Gln Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
            420                 425                 430
Pro Gln Glu Gly Leu Tyr Asn Glu Leu Gln Lys Asp Lys Met Ala Glu
                435                 440                 445
Ala Tyr Ser Glu Ile Gly Met Lys Gly Glu Arg Arg Arg Gly Lys Gly
            450                 455                 460
His Asp Gly Leu Tyr Gln Gly Leu Ser Thr Ala Thr Lys Asp Thr Tyr
465                 470                 475                 480
Asp Ala Leu His Met Gln Ala Leu Pro Pro Arg
                485                 490

<210> SEQ ID NO 77
<211> LENGTH: 1464
<212> TYPE: DNA
<213> ORGANISM: Artificial Sequence
<220> FEATURE:
<223> OTHER INFORMATION: LTG 2075 (hScFv aCD123 CD8 TM 4-1BB CD3 zeta)

<400> SEQUENCE: 77
atgctgctgc tggtgaccag cctgctgctg tgcgaactgc cgcatccggc gtttctgctg      60
attccggaag tgcaactcgt cgaaactgga gccgaagtga aaaagcctgg agcgtccgtc     120
aaagtgtcgt gcaaggcctc cggctacacc ttcacgacct actacgtgca ctgggtcaga     180
caggctccgg gtcaagggct ggagtggatg ggcatcatta ccccgtccgg tggaagcacc     240
tcctatgcgc aaaagttcca gggtcgcgtc accatgactc gcgataccgc cacttccact     300
gtgtacatgg aactgagctc cctgaggtcc gaggacaccg ccgtgtacta ctgcgcacgg     360
gatggaggct gggcggcta cgaggcttgg ggacagggca ccctcgtgac tgtgtcaagc     420 ggaggggtg atccggagg ggaggatca ggcggtggtg aagcgatat ccagcttacc     480 cagtcgcctt ccgcgctgtc tgcatcggcc ggcgacagag tgacaattac ctgtcaagcc     540
agccaggaca tctccaacta tctgaactgg taccagcaga gcccggaaa ggctccgaag     600 ctgctgatct acgacgccag caacctggaa cggggcgtgc catcacggtt ctcgggatca     660
gggtcgggca ctgagttcac cttcaccatc tcctccctcc aacccgagga cattgccacc     720
tactactgcc agcagtacga caacctcccg atcacctttg acaggggac tcgcctggaa     780 atcaaggcgg ccgcaactac caccctgcc cctcggccgc cgactccggc cccaaccatc     840
gcaagccaac cctctccctt cgccccgaa gcttgccgcc cggccgcggg tggagccgtg     900
catacccggg ggctggactt tgcctgcgat atctacattt gggccccgct ggccggcact     960
tgcggcgtgc tcctgctgtc gctggtcatc acccttact gcaagagggg ccggaagaag    1020
ctgctttaca tcttcaagca gccgttcatg cggcccgtgc agacgactca ggaagaggac    1080
ggatgctcgt gcagattccc tgaggaggaa aggggggat gcgaactgcg cgtcaagttc    1140
tcacggtccg ccgacgcccc cgcatatcaa cagggccaga tcagctcta caacgagctg    1200 aacctgggaa ggagagagga gtacgacgtg ctggacaagc gacgcggacg cgacccggag    1260 atgggggga accacggcg gaaaaccct caggaaggac tgtacaacga actccagaaa    1320
```

```
gacaagatgg cggaagccta ctcagaaatc gggatgaagg gagagcggag gaggggaaag    1380
ggtcacgacg ggctgtacca gggactgagc accgccacta aggataccta cgatgccttg    1440
catatgcaag cactcccacc ccgg                                          1464
```

<210> SEQ ID NO 78  
<211> LENGTH: 488  
<212> TYPE: PRT  
<213> ORGANISM: Artificial Sequence  
<220> FEATURE:  
<223> OTHER INFORMATION: LTG 2075 (hScFv aCD123 CD8 TM 4-1BB CD3 zeta)

<400> SEQUENCE: 78

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Thr Gly Ala Glu
            20                  25                  30

Val Lys Lys Pro Gly Ala Ser Val Lys Val Ser Cys Lys Ala Ser Gly
        35                  40                  45

Tyr Thr Phe Thr Thr Tyr Tyr Val His Trp Val Arg Gln Ala Pro Gly
    50                  55                  60

Gln Gly Leu Glu Trp Met Gly Ile Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Asp Gly Leu Gly Gly Tyr Glu
        115                 120                 125

Ala Trp Gly Gln Gly Thr Leu Val Thr Val Ser Ser Gly Gly Gly Gly
    130                 135                 140

Ser Gly Gly Gly Gly Ser Gly Gly Gly Gly Ser Asp Ile Gln Leu Thr
145                 150                 155                 160

Gln Ser Pro Ser Ala Leu Ser Ala Ser Ala Gly Asp Arg Val Thr Ile
                165                 170                 175

Thr Cys Gln Ala Ser Gln Asp Ile Ser Asn Tyr Leu Asn Trp Tyr Gln
            180                 185                 190

Gln Lys Pro Gly Lys Ala Pro Lys Leu Leu Ile Tyr Asp Ala Ser Asn
        195                 200                 205

Leu Glu Arg Gly Val Pro Ser Arg Phe Ser Gly Ser Gly Ser Gly Thr
    210                 215                 220

Glu Phe Thr Phe Thr Ile Ser Ser Leu Gln Pro Glu Asp Ile Ala Thr
225                 230                 235                 240

Tyr Tyr Cys Gln Gln Tyr Asp Asn Leu Pro Ile Thr Phe Gly Gln Gly
                245                 250                 255

Thr Arg Leu Glu Ile Lys Ala Ala Ala Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335
```

```
Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 79
<211> LENGTH: 36
<212> TYPE: DNA
<213> ORGANISM: Artificial Sequence
<220> FEATURE:
<223> OTHER INFORMATION: human IgG4 hinge

<400> SEQUENCE: 79
gagagcaaat acgggccgcc atgtcccccg tgtccg                              36

<210> SEQ ID NO 80
<211> LENGTH: 12
<212> TYPE: PRT
<213> ORGANISM: Artificial Sequence
<220> FEATURE:
<223> OTHER INFORMATION: human IgG4 hinge

<400> SEQUENCE: 80

Glu Ser Lys Tyr Gly Pro Pro Cys Pro Pro Cys Pro
1               5                   10

<210> SEQ ID NO 81
<211> LENGTH: 327
<212> TYPE: DNA
<213> ORGANISM: Artificial Sequence
<220> FEATURE:
<223> OTHER INFORMATION: human IgG4 CH2 domain

<400> SEQUENCE: 81
gcaccaccag ttgctggccc tagtgtcttc ttgttccctc ccaagcccaa agacaccttg     60
atgatttcca gaactcctga ggttacctgc gttgtcgtag atgtttctca ggaggaccca    120
gaggtccaat ttaactggta cgttgatggg gtggaagttc acaatgcgaa gacaaagccg    180
cgggaagaac aatttcagtc cacttaccgg gttgtcagcg ttctgacggt attgcatcaa    240
gactggctta tggaaaagga atataagtgt aaggtgtcca caaaggtttt gccgagcagt    300
attgagaaga ccatatcaaa ggcgaag                                       327
```

-continued

<210> SEQ ID NO 82
<211> LENGTH: 109
<212> TYPE: PRT
<213> ORGANISM: Artificial Sequence
<220> FEATURE:
<223> OTHER INFORMATION: human IgG4 CH2 domain

<400> SEQUENCE: 82

```
Ala Pro Pro Val Ala Gly Pro Ser Val Phe Leu Phe Pro Pro Lys Pro
 1               5                  10                  15

Lys Asp Thr Leu Met Ile Ser Arg Thr Pro Glu Val Thr Cys Val Val
             20                  25                  30

Val Asp Val Ser Gln Glu Asp Pro Glu Val Gln Phe Asn Trp Tyr Val
         35                  40                  45

Asp Gly Val Glu Val His Asn Ala Lys Thr Lys Pro Arg Glu Glu Gln
     50                  55                  60

Phe Gln Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Gly
                 85                  90                  95

Leu Pro Ser Ser Ile Glu Lys Thr Ile Ser Lys Ala Lys
            100                 105
```

<210> SEQ ID NO 83
<211> LENGTH: 321
<212> TYPE: DNA
<213> ORGANISM: Artificial Sequence
<220> FEATURE:
<223> OTHER INFORMATION: human IgG4 CH3 domain

<400> SEQUENCE: 83

```
gggcagccgc gcgagccaca agtttacact tgccgccat ctcaagagga aatgactaaa      60
aaccaggtat ccttgacatg cctcgtaaaa ggatttttatc catctgatat tgctgtggaa    120
tgggagtcta acgggcagcc ggaaaataat tacaaaacta caccacctgt gctcgattca    180
gatggaagtt tcttcctttta cagtagactt acggtggaca atctaggtg caggaaggg     240 aatgtgtttta gttgtagtgt aatgcacgag gcacttcata accactatac acagaagtca    300
ctgagtttga gtcttggcaa a                                                321
```

<210> SEQ ID NO 84
<211> LENGTH: 107
<212> TYPE: PRT
<213> ORGANISM: Artificial Sequence
<220> FEATURE:
<223> OTHER INFORMATION: human IgG4 CH3 domain

<400> SEQUENCE: 84

```
Gly Gln Pro Arg Glu Pro Gln Val Tyr Thr Leu Pro Pro Ser Gln Glu
 1               5                  10                  15

Glu Met Thr Lys Asn Gln Val Ser Leu Thr Cys Leu Val Lys Gly Phe
             20                  25                  30

Tyr Pro Ser Asp Ile Ala Val Glu Trp Glu Ser Asn Gly Gln Pro Glu
         35                  40                  45

Asn Asn Tyr Lys Thr Thr Pro Pro Val Leu Asp Ser Asp Gly Ser Phe
     50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95
```

Thr Gln Lys Ser Leu Ser Leu Ser Leu Gly Lys
            100                 105

<210> SEQ ID NO 85
<211> LENGTH: 684
<212> TYPE: DNA
<213> ORGANISM: Artificial Sequence
<220> FEATURE:
<223> OTHER INFORMATION: human IgG4 hinge CH2 CH3 domain

<400> SEQUENCE: 85

```
gagagcaaat acgggccgcc atgtcccccg tgtccggcac caccagttgc tggccctagt      60
gtcttcttgt tccctcccaa gcccaaagac accttgatga tttccagaac tcctgaggtt     120
acctgcgttg tcgtagatgt ttctcaggag acccagagg tccaatttaa ctggtacgtt      180
gatgggggtgg aagttcacaa tgcgaagaca aagccgcggg aagaacaatt tcagtccact    240
taccgggttg tcagcgttct gacggtattg catcaagact ggcttaatgg aaaggaatat    300
aagtgtaagg tgtccaacaa aggtttgccg agcagtattg agaagaccat atcaaaggcg    360
aagggggcagc cgcgcgagcc acaagtttac actttgccgc catctcaaga ggaaatgact    420
aaaaaccagg tatccttgac atgcctcgta aaaggatttt atccatctga tattgctgtg    480
gaatgggagt ctaacgggca gccggaaaat aattacaaaa ctacaccacc tgtgctcgat    540
tcagatggaa gtttcttcct ttacagtaga cttacggtgg acaaatctag gtggcaggaa    600
gggaatgtgt ttagttgtag tgtaatgcac gaggcacttc ataaccacta tacacagaag    660
tcactgagtt tgagtcttgg caaa                                           684
```

<210> SEQ ID NO 86
<211> LENGTH: 228
<212> TYPE: PRT
<213> ORGANISM: Artificial Sequence
<220> FEATURE:
<223> OTHER INFORMATION: human IgG4 hinge CH2 CH3 domain

<400> SEQUENCE: 86

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro

```
              165                 170                 175
Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
210                 215                 220

Ser Leu Gly Lys
225

<210> SEQ ID NO 87
<211> LENGTH: 1503
<212> TYPE: DNA
<213> ORGANISM: Artificial Sequence
<220> FEATURE:
<223> OTHER INFORMATION: LTG 2076 (hScFv aCD123 CD8 TM 4-1BB CD3 zeta)

<400> SEQUENCE: 87
atgctgctgc tggtgaccag cctgctgctg tgcgaactgc cgcatccggc gtttctgctg      60
attccggaag tgcaattggt ccagagcgga ggaggacttg tgaagccagg cggatccctg     120
agattgtcat gcgccgcatc ggggttcacc ttttcctcct actccatgaa ctgggtcaga     180
caggcgccgg aaagggact tgaatgggtg tcgtccattt cctcctcctc gtcctacatc     240
tactacgccg actccgtgaa gggccgcttc accatctccc gggacaacgc caagaacagc     300
ctgtatctcc aaatgaactc cctgcgggcc gaagatactg ctgtgtatta ctgcgctcgg     360
gacttcccgt acgactcatc gggctattac tcggacgcgt tcgatatctg gggccaggga     420
actatggtca ccgtcagctc tggtggcggt ggttccggag ggggtggatc cggtggcgga     480
ggatcagaga ttgtgctgac ccagtccccg ctgtcactgc ccgtgactcc gggagagcct     540
gcctcgatct cgtgtcggtc agccagtcc ctgctgcact cgaatgggta caactacctc     600
gattggtacc tccaaaagcc tgggcagtca ccccaactgc tgatctacct cgggagcaac     660
agagccagcg gagtgcctga ccgctttagc ggttccggat ccggcaccga cttcaccctg     720
aaaatcagcc gggtggaagc cgaggatgtc ggcgtgtact actgcatgca ggcactgcag     780
actctggggt acaccttcgg ccagggcacg aagctcgaga tcaaggcggc cgcaactacc     840
acccctgccc ctcggccgcc gactccggcc caaccatcg caagccaacc cctctccttg     900
cgccccgaag cttgccgccc ggccgcgggt ggagccgtgc atacccgggg gctggacttt     960
gcctgcgata tctacatttg gccccgctg ccggcacttt cggcgtgct cctgctgtcg    1020 ctggtcatca ccctttactg caagaggggc cggaagaagc tgctttacat cttcaagcag    1080
ccgttcatgc ggcccgtgca gacgactcag gaagaggacg gatgctcgtg cagattccct    1140
gaggaggaag aggggggatg cgaactgcgc gtcaagttct cacggtccgc cgacgccccc    1200
gcatatcaac agggccagaa tcagctctac aacgagctga acctgggaag agagaggag    1260 tacgacgtgc tggacaagcg acgcggacgc gacccggaga tggggggaa accacggcgg    1320 aaaaaccctc aggaaggact gtacaacgaa ctccagaaag acaagatggc ggaagcctac    1380
tcagaaatcg gatgaaggg agagcggagg aggggaagg gtcacgacgg gctgtaccag    1440
ggactgagca ccgccactaa ggataccctac gatgccttgc atatgcaagc actcccaccc    1500
cgg                                                                  1503

<210> SEQ ID NO 88
<211> LENGTH: 501
```

```
<212> TYPE: PRT
<213> ORGANISM: Artificial Sequence
<220> FEATURE:
<223> OTHER INFORMATION: LTG 2076 (hScFv aCD123 CD8 TM 4-1BB CD3 zeta)

<400> SEQUENCE: 88
```

| | | | | | | | | | | | | | | |
|---|---|---|---|---|---|---|---|---|---|---|---|---|---|---|
| Met | Leu | Leu | Leu | Val | Thr | Ser | Leu | Leu | Cys | Glu | Leu | Pro | His | Pro |
| 1 | | | | 5 | | | | | 10 | | | | | 15 |
| Ala | Phe | Leu | Leu | Ile | Pro | Glu | Val | Gln | Leu | Val | Gln | Ser | Gly | Gly |
| | | | 20 | | | | | 25 | | | | | 30 | |
| Leu | Val | Lys | Pro | Gly | Gly | Ser | Leu | Arg | Leu | Ser | Cys | Ala | Ala | Ser | Gly |
| | | 35 | | | | | 40 | | | | | 45 | | | |
| Phe | Thr | Phe | Ser | Ser | Tyr | Ser | Met | Asn | Trp | Val | Arg | Gln | Ala | Pro | Gly |
| | 50 | | | | | 55 | | | | | 60 | | | | |
| Lys | Gly | Leu | Glu | Trp | Val | Ser | Ser | Ile | Ser | Ser | Ser | Ser | Ser | Tyr | Ile |
| 65 | | | | | 70 | | | | | 75 | | | | | 80 |
| Tyr | Tyr | Ala | Asp | Ser | Val | Lys | Gly | Arg | Phe | Thr | Ile | Ser | Arg | Asp | Asn |
| | | | | 85 | | | | | 90 | | | | | 95 | |
| Ala | Lys | Asn | Ser | Leu | Tyr | Leu | Gln | Met | Asn | Ser | Leu | Arg | Ala | Glu | Asp |
| | | | 100 | | | | | 105 | | | | | 110 | | |
| Thr | Ala | Val | Tyr | Tyr | Cys | Ala | Arg | Asp | Phe | Pro | Tyr | Asp | Ser | Ser | Gly |
| | | | 115 | | | | | 120 | | | | | 125 | | |
| Tyr | Tyr | Ser | Asp | Ala | Phe | Asp | Ile | Trp | Gly | Gln | Gly | Thr | Met | Val | Thr |
| | 130 | | | | | 135 | | | | | 140 | | | | |
| Val | Ser | Ser | Gly | Gly | Gly | Gly | Ser | Gly | Gly | Gly | Gly | Ser | Gly | Gly | Gly |
| 145 | | | | | 150 | | | | | 155 | | | | | 160 |
| Gly | Ser | Glu | Ile | Val | Leu | Thr | Gln | Ser | Pro | Leu | Ser | Leu | Pro | Val | Thr |
| | | | | 165 | | | | | 170 | | | | | 175 | |
| Pro | Gly | Glu | Pro | Ala | Ser | Ile | Ser | Cys | Arg | Ser | Ser | Gln | Ser | Leu | Leu |
| | | | 180 | | | | | 185 | | | | | 190 | | |
| His | Ser | Asn | Gly | Tyr | Asn | Tyr | Leu | Asp | Trp | Tyr | Leu | Gln | Lys | Pro | Gly |
| | | | 195 | | | | | 200 | | | | | 205 | | |
| Gln | Ser | Pro | Gln | Leu | Leu | Ile | Tyr | Leu | Gly | Ser | Asn | Arg | Ala | Ser | Gly |
| | 210 | | | | | 215 | | | | | 220 | | | | |
| Val | Pro | Asp | Arg | Phe | Ser | Gly | Ser | Gly | Ser | Gly | Thr | Asp | Phe | Thr | Leu |
| 225 | | | | | 230 | | | | | 235 | | | | | 240 |
| Lys | Ile | Ser | Arg | Val | Glu | Ala | Glu | Asp | Val | Gly | Val | Tyr | Tyr | Cys | Met |
| | | | | 245 | | | | | 250 | | | | | 255 | |
| Gln | Ala | Leu | Gln | Thr | Leu | Gly | Tyr | Thr | Phe | Gly | Gln | Gly | Thr | Lys | Leu |
| | | | 260 | | | | | 265 | | | | | 270 | | |
| Glu | Ile | Lys | Ala | Ala | Ala | Thr | Thr | Thr | Pro | Ala | Pro | Arg | Pro | Pro | Thr |
| | | 275 | | | | | 280 | | | | | 285 | | | |
| Pro | Ala | Pro | Thr | Ile | Ala | Ser | Gln | Pro | Leu | Ser | Leu | Arg | Pro | Glu | Ala |
| | 290 | | | | | 295 | | | | | 300 | | | | |
| Cys | Arg | Pro | Ala | Ala | Gly | Gly | Ala | Val | His | Thr | Arg | Gly | Leu | Asp | Phe |
| 305 | | | | | 310 | | | | | 315 | | | | | 320 |
| Ala | Cys | Asp | Ile | Tyr | Ile | Trp | Ala | Pro | Leu | Ala | Gly | Thr | Cys | Gly | Val |
| | | | | 325 | | | | | 330 | | | | | 335 | |
| Leu | Leu | Leu | Ser | Leu | Val | Ile | Thr | Leu | Tyr | Cys | Lys | Arg | Gly | Arg | Lys |
| | | | 340 | | | | | 345 | | | | | 350 | | |
| Lys | Leu | Leu | Tyr | Ile | Phe | Lys | Gln | Pro | Phe | Met | Arg | Pro | Val | Gln | Thr |
| | | 355 | | | | | 360 | | | | | 365 | | | |
| Thr | Gln | Glu | Glu | Asp | Gly | Cys | Ser | Cys | Arg | Phe | Pro | Glu | Glu | Glu | Glu |
| 370 | | | | | 375 | | | | | 380 | | | | | |

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
            405                 410                 415

Arg Arg Glu Glu Tyr Asp Val Leu Asp Lys Arg Arg Gly Arg Asp Pro
        420                 425                 430

Glu Met Gly Gly Lys Pro Arg Arg Lys Asn Pro Gln Glu Gly Leu Tyr
    435                 440                 445

Asn Glu Leu Gln Lys Asp Lys Met Ala Glu Ala Tyr Ser Glu Ile Gly
450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
            485                 490                 495

Ala Leu Pro Pro Arg
            500

```
<210> SEQ ID NO 89
<211> LENGTH: 1491
<212> TYPE: DNA
<213> ORGANISM: Artificial Sequence
<220> FEATURE:
<223> OTHER INFORMATION: LTG 2077 (hScFv aCD123 CD8 TM 4-1BB CD3 zeta)

<400> SEQUENCE: 89
atgctgctgc tggtgaccag cctgctgctg tgcgaactgc cgcatccggc gtttctgctg      60
attccgcaag tgcaactcgt ccaatccggt gccgaagtca agaagcctgg ttcctccgtg     120
aaagtgtcgt gcaaagccag cggcgggact tttagctcct acgcgatcag ctgggtcaga     180 caggccctg acaaggcct cgagtggatg gcggcatca ttccgatttt cggtaccgcc        240
aactacgccc agaagttcca gggacgcgtg accattacta ccgacgagag cacctcaacc     300
gcatacatgg aactgtccag cctgcgctcc gaggacacgg ctgtgtacta ttgcgccaga     360
cggggatggg gaggattctc ctccggctcc gcattcgaca tctggggaca gggcactatg     420
gtcactgtgt catccggggg aggaggatca ggcggtggag atccggtgg tggcggatcc     480 aacttcatgc tgacccagcc ccactcagtg tcggaatcgc ccggcaacac cgtgactatc     540
agctgcaccg gatccagcgg gaccatcggc tctaatttcg tgcagtggta ccagcagtcc     600
ccagggagag ctccgaccct gttgatctac gaggacacaa agcggccaag cggagtgccg     660
cctagattcg ccggctccgt ggattcctcg tccaactcgg cgtcgctgac catcagcgga     720
ctcaagactg aagatgaagc cgactactac tgtcagtcct acgactcgag caactgggtg     780 tttggggcg ggactaagct gaccgtgctt ggagcggccg caactaccac ccctgccct       840 cggccgccga ctccggcccc aaccatcgca agccaacccc tctccttgcg ccccgaagct     900
tgccgcccgg ccgcgggtgg agccgtgcat cccgggggc tggactttgc ctgcgatatc     960
tacatttggg ccccgctggc cggcacttgc ggcgtgctcc tgctgtcgct ggtcatcacc    1020
ctttactgca gaggggccga gaagaagctg ctttacatct tcaagcagcc gttcatgcgg    1080
cccgtgcaga cgactcagga agaggacgga tgctcgtgca gattccctga ggaggaagag    1140
gggggatgcg aactgcgcgt caagttctca cggtccgccg acgcccccgc atatcaacag    1200
ggccagaatc agctctacaa cgagctgaac ctgggaagga gaggagta cgacgtgctg      1260 gacaagcgac gcgacgcgga cccggagatg ggggggaaac cacggcggaa aaaccctcag    1320
gaaggactgt acaacgaact ccagaaagac aagatggcgg aagcctactc agaaatcggg    1380
```

```
atgaaggag agcggaggag gggaaagggt cacgacgggc tgtaccaggg actgagcacc    1440
gccactaagg atacctacga tgccttgcat atgcaagcac tcccaccccg g            1491
```

<210> SEQ ID NO 90
<211> LENGTH: 497
<212> TYPE: PRT
<213> ORGANISM: Artificial Sequence
<220> FEATURE:
<223> OTHER INFORMATION: LTG 2077 (hScFv aCD123 CD8 TM 4-1BB CD3 zeta)

<400> SEQUENCE: 90

```
Met Leu Leu Leu Val Thr Ser Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Thr Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Arg Gly Trp Gly Gly Phe Ser Ser
        115                 120                 125

Gly Ser Ala Phe Asp Ile Trp Gly Gln Gly Thr Met Val Thr Val Ser
    130                 135                 140

Ser Gly Gly Gly Gly Ser Gly Gly Gly Ser Gly Gly Gly Gly Ser
145                 150                 155                 160

Asn Phe Met Leu Thr Gln Pro His Ser Val Ser Glu Ser Pro Gly Asn
                165                 170                 175

Thr Val Thr Ile Ser Cys Thr Gly Ser Ser Gly Thr Ile Gly Ser Asn
            180                 185                 190

Phe Val Gln Trp Tyr Gln Gln Ser Pro Gly Arg Ala Pro Thr Leu Leu
        195                 200                 205

Ile Tyr Glu Asp Thr Lys Arg Pro Ser Gly Val Pro Pro Arg Phe Ala
    210                 215                 220

Gly Ser Val Asp Ser Ser Asn Ser Ala Ser Leu Thr Ile Ser Gly
225                 230                 235                 240

Leu Lys Thr Glu Asp Glu Ala Asp Tyr Tyr Cys Gln Ser Tyr Asp Ser
                245                 250                 255

Ser Asn Trp Val Phe Gly Gly Gly Thr Lys Leu Thr Val Leu Gly Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
```

```
               340                 345                 350
Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Gly Gly Cys Glu
        370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Gly Arg Asp Pro Glu Met Gly Gly
            420                 425                 430

Lys Pro Arg Arg Lys Asn Pro Gln Glu Gly Leu Tyr Asn Glu Leu Gln
                435                 440                 445

Lys Asp Lys Met Ala Glu Ala Tyr Ser Glu Ile Gly Met Lys Gly Glu
            450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 91
<211> LENGTH: 1479
<212> TYPE: DNA
<213> ORGANISM: Artificial Sequence
<220> FEATURE:
<223> OTHER INFORMATION: LTG 2078 (hScFv aCD123 CD8 TM 4-1BB CD3 zeta)

<400> SEQUENCE: 91

```
atgctgctgc tggtgaccag cctgctgctg tgcgaactgc cgcatccggc gtttctgctg      60
attccggaag tccaattggt gcagagcgga tccgaactta agaaacctgg cgcgagcgtg     120
aaagtgtcct gcaaggcctc cggagggact ttctcgtcgt acgccattag ctgggtccgc     180
caagctcctg gccaaggcct ggagtggatg gcgggattac tccccatctt cgggactgcg     240
aactacgccc agaagtttca gggccgggtc actatcaccg ccgacgaatc aacctcgacc     300
gcctacatgg aactgtcctc gcttcggtcc gaggatactg ccgtgtacta ttgtgcctca     360
acggccagac gcggatggga caccgctggt ccgctcgatt actggggcca gggaaccctc     420
gtgaccgtca gctccggagg aggaggctcc ggtggtggag gatccggggg tggtggatcc     480
gacatccaaa tgacccagtc ccctcgtcc ctgagcgcct ctgtgggcga cagagtgaca     540
attgcatgca gggcctcaca gactatctcc cgctacctga actggtacca gcagaagcca     600
ggaaaggccc ctaagctgct catctacgct gcgtcctcgc tccaatccgg ggtgtcctca     660
cggttttccg gatcgggttc cggcaccgag ttcaccctga ccatcagcag cctgcagccc     720
gaggacttcg caacctactt ctgccagcaa acctactccc cgccgattac gttcggacag     780
gggactcggc tggaaatcaa ggcggccgca actaccaccc tgcccctcg gccgccgact     840 ccggccccaa ccatcgcaag ccaacccctc tccttgcgcc ccgaagcttg ccgcccggcc     900
gcgggtggag ccgtgcatac ccgggggctg actttgcct gcgatatcta catttgggcc     960
ccgctggccg gcacttgcgg cgtgctcctg ctgtcgctgg tcatcaccct ttactgcaag    1020
aggggccgga gaagctgct ttacatcttc aagcagccgt tcatgcggcc cgtgcagacg    1080
actcaggaag aggacggatg ctcgtgcaga ttccctgagg aggaagaggg gggatgcgaa    1140
```

-continued

```
ctgcgcgtca agttctcacg gtccgccgac gcccccgcat atcaacaggg ccagaatcag      1200
ctctacaacg agctgaacct gggaaggaga gaggagtacg acgtgctgga caagcgacgc      1260
ggacgcgacc cggagatggg ggggaaacca cggcggaaaa accctcagga aggactgtac      1320
aacgaactcc agaaagacaa gatggcggaa gcctactcag aaatcgggat gaagggagag      1380
cggaggaggg gaaagggtca cgacgggctg taccagggac tgagcaccgc cactaaggat      1440
acctacgatg ccttgcatat gcaagcactc ccaccccgg                              1479
```

<210> SEQ ID NO 92
<211> LENGTH: 493
<212> TYPE: PRT
<213> ORGANISM: Artificial Sequence
<220> FEATURE:
<223> OTHER INFORMATION: LTG 2078 (hScFv aCD123 CD8 TM 4-1BB CD3 zeta)

<400> SEQUENCE: 92

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ser Glu
            20                  25                  30

Leu Lys Lys Pro Gly Ala Ser Val Lys Val Ser Cys Lys Ala Ser Gly
        35                  40                      45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Ser Thr Ala Arg Arg Gly Trp Asp Thr
        115                 120                 125

Ala Gly Pro Leu Asp Tyr Trp Gly Gln Gly Thr Leu Val Thr Val Ser
    130                 135                 140

Ser Gly Gly Gly Gly Ser Gly Gly Gly Ser Gly Gly Gly Gly Ser
145                 150                 155                 160

Asp Ile Gln Met Thr Gln Ser Pro Ser Ser Leu Ser Ala Ser Val Gly
                165                 170                 175

Asp Arg Val Thr Ile Ala Cys Arg Ala Ser Gln Thr Ile Ser Arg Tyr
            180                 185                 190

Leu Asn Trp Tyr Gln Gln Lys Pro Gly Lys Ala Pro Lys Leu Leu Ile
        195                 200                 205

Tyr Ala Ala Ser Ser Leu Gln Ser Gly Val Ser Ser Arg Phe Ser Gly
    210                 215                 220

Ser Gly Ser Gly Thr Glu Phe Thr Leu Thr Ile Ser Ser Leu Gln Pro
225                 230                 235                 240

Glu Asp Phe Ala Thr Tyr Phe Cys Gln Gln Thr Tyr Ser Pro Pro Ile
                245                 250                 255

Thr Phe Gly Gln Gly Thr Arg Leu Glu Ile Lys Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300
```

| | | | | | | | | | | | | | | |
|---|---|---|---|---|---|---|---|---|---|---|---|---|---|---|
|Val|His|Thr|Arg|Gly|Leu|Asp|Phe|Ala|Cys|Asp|Ile|Tyr|Ile|Trp|Ala|
|305| | | |310| | | |315| | | |320| | | |

Pro Leu Ala Gly Thr Cys Gly Val Leu Leu Ser Leu Val Ile Thr
            325              330              335

Leu Tyr Cys Lys Arg Gly Arg Lys Lys Leu Leu Tyr Ile Phe Lys Gln
          340              345              350

Pro Phe Met Arg Pro Val Gln Thr Thr Gln Glu Glu Asp Gly Cys Ser
        355              360              365

Cys Arg Phe Pro Glu Glu Glu Glu Gly Gly Cys Glu Leu Arg Val Lys
370              375              380

Phe Ser Arg Ser Ala Asp Ala Pro Ala Tyr Gln Gln Gly Gln Asn Gln
385              390              395              400

Leu Tyr Asn Glu Leu Asn Leu Gly Arg Arg Glu Glu Tyr Asp Val Leu
          405              410              415

Asp Lys Arg Arg Gly Arg Asp Pro Glu Met Gly Gly Lys Pro Arg Arg
        420              425              430

Lys Asn Pro Gln Glu Gly Leu Tyr Asn Glu Leu Gln Lys Asp Lys Met
          435              440              445

Ala Glu Ala Tyr Ser Glu Ile Gly Met Lys Gly Glu Arg Arg Arg Gly
450              455              460

Lys Gly His Asp Gly Leu Tyr Gln Gly Leu Ser Thr Ala Thr Lys Asp
465              470              475              480

Thr Tyr Asp Ala Leu His Met Gln Ala Leu Pro Pro Arg
                  485              490

<210> SEQ ID NO 93
<211> LENGTH: 1473
<212> TYPE: DNA
<213> ORGANISM: Artificial Sequence
<220> FEATURE:
<223> OTHER INFORMATION: LTG 2079 (hScFv aCD123 CD8 TM 4-1BB CD3 zeta)

<400> SEQUENCE: 93

```
atgctgctgc tggtgaccag cctgctgctg tgcgaactgc cgcatccggc gtttctgctg      60
attccggaag tgcaactcgt cgaaacaggg gcagaagtga aaacccagg ctcaagcgtg     120
aaagtgtcgt gcaaggcttc gggcggaact ctgtccaact acgccatctc ctgggtccgc    180
caagctccgg gaaagggcct cgagtggatg gcgggaatca ttcccatttt cgggaccgcc    240
aactacgcgc aaaagttcca gggccgggtc actatcaccg cggacgaaag caccagcacc    300
gcctacatgg aactgtcctc cctgcgctcc gaggacactg ccgtgtacta ttgcgcccgg    360
aggtcatcgt ggtaccccga gggctgcttc agcactggg gacagggcac tctcgtgacc    420
gtgtcgtcgg gtggtggtgg atcaggaggg ggaggatccg gaggaggcgg aagcgatatt    480
cagctgaccc agtcaccgag ctccctgtcc gcctccaccg gagacagagt gaccatcacg    540
tgtcgggcct cccaagggat ctcctcctac ctggcctggt accagcagaa gcctggaaag    600
gcaccgaagt tgctgatcta cgccgcgagc acccttcagt ccggagtgcc tagccgcttc    660
tcgggttccg gctctggcac tgacttcact ctgaccatta gctgctgca gtccgaggat    720
tttgccacct actactgcca gcagtactat agctaccccc tgaccttcgg ggcggaacc    780
aagctcgaca tcaaggcggc cgcaactacc accctgccc ctcggccgcc gactccggcc    840
ccaaccatcg caagccaacc cctctccttg cgcccgaag cttgcgccc ggccgcgggt    900
ggagccgtgc ataccggggg ctggactttt gcctgcgata tctacatttg ggccccgctg    960
gccggcactt gcggcgtgct cctgctgtcg ctggtcatca ccctttactg caagaggggc   1020
```

-continued

```
cggaagaagc tgctttacat cttcaagcag ccgttcatgc ggcccgtgca gacgactcag    1080
gaagaggacg gatgctcgtg cagattccct gaggaggaag agggggggatg cgaactgcgc    1140 gtcaagttct cacggtccgc cgacgccccc gcatatcaac agggccagaa tcagctctac    1200
aacgagctga acctgggaag agagaggag tacgacgtgc tggacaagcg acgcggacgc    1260
gacccggaga tggggggggaa accacggcgg aaaaaccctc aggaaggact gtacaacgaa    1320
ctccagaaag acaagatggc ggaagcctac tcagaaatcg ggatgaaggg agagcggagg    1380
aggggaaagg gtcacgacgg gctgtaccag ggactgagca ccgccactaa ggatacctac    1440
gatgccttgc atatgcaagc actcccaccc cgg                                 1473
```

<210> SEQ ID NO 94
<211> LENGTH: 491
<212> TYPE: PRT
<213> ORGANISM: Artificial Sequence
<220> FEATURE:
<223> OTHER INFORMATION: LTG 2079 (hScFv aCD123 CD8 TM 4-1BB CD3 zeta)

<400> SEQUENCE: 94

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Thr Gly Ala Glu
            20                  25                  30

Val Lys Asn Pro Gly Ser Ser Val Lys Val Ser Cys Lys Ala Ser Gly
        35                  40                  45

Gly Thr Leu Ser Asn Tyr Ala Ile Ser Trp Val Arg Gln Ala Pro Gly
    50                  55                  60

Lys Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Arg Ser Ser Trp Tyr Pro Glu Gly
        115                 120                 125

Cys Phe Gln His Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Leu Thr Gln Ser Pro Ser Ser Leu Ser Ala Ser Thr Gly Asp Arg
                165                 170                 175

Val Thr Ile Thr Cys Arg Ala Ser Gln Gly Ile Ser Ser Tyr Leu Ala
            180                 185                 190

Trp Tyr Gln Gln Lys Pro Gly Lys Ala Pro Lys Leu Leu Ile Tyr Ala
        195                 200                 205

Ala Ser Thr Leu Gln Ser Gly Val Pro Ser Arg Phe Ser Gly Ser Gly
    210                 215                 220

Ser Gly Thr Asp Phe Thr Leu Thr Ile Ser Cys Leu Gln Ser Glu Asp
225                 230                 235                 240

Phe Ala Thr Tyr Tyr Cys Gln Gln Tyr Tyr Ser Tyr Pro Leu Thr Phe
                245                 250                 255

Gly Gly Gly Thr Lys Leu Asp Ile Lys Ala Ala Ala Thr Thr Thr Pro
            260                 265                 270

Ala Pro Arg Pro Pro Thr Pro Ala Pro Thr Ile Ala Ser Gln Pro Leu
```

-continued

```
                275                 280                 285
Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 95
<211> LENGTH: 1485
<212> TYPE: DNA
<213> ORGANISM: Artificial Sequence
<220> FEATURE:
<223> OTHER INFORMATION: LTG 2080 (hScFv aCD123 CD8 TM 4-1BB CD3 zeta)

<400> SEQUENCE: 95

```
atgctgctgc tggtgaccag cctgctgctg tgcgaactgc cgcatccggc gtttctgctg      60
attccggaag tccaattggt gcagagcgga gctgaagtga agaaacctgg cgcgaccgtg     120
aagatctcgt gcaaagtgtc cggctacact ttcaccgact actatatgca ctgggtgcaa     180
caggcgccgg gaaagggact ggagtggatt ggccttgtgg accccgaaga tggcgaaacc     240
atctacgccg agaagttcca gggccgggtc actatcaccg cggacacttc cacggacacc     300
gcctacatgg aactgagctc cctgagatcc gaggacaccg ccgtgtacta ctgcgccact     360
gccccactgg gggaagtcgg cgcagcagtg gactactggg gacagggaac tctcgtcact     420
gtgtccagcg gtgaggagg cagcggtggt ggaggctccg gtggtggtgg atcccatgtc     480
attctgactc agccgccgtc agtgtcagcc gcccctggac aagaggtgtc catctcctgt     540
tcggggtccg atgccaacat tgggaccaac ttggtgtcgt ggtaccagca cgtgcctgga     600
acagccccca agctgctcat ctacgagaac tcgaagaggc catccggaat tcccgccgg     660
ttttcatcga gccagtcagg gacctccgct accctggcta tcagcgggct ccagtctggg     720
gatgaagcga tctactactg cctgacctgg gatcgcaccc tctccggaaa gatcttcggt     780
ggcggcactc agctgaccgt gcttggagcg gccgcaacta ccaccctgc ccctcggccg     840
```

```
ccgactccgg ccccaaccat cgcaagccaa cccctctcct tgcgcccga agcttgccgc    900 ccggccgcgg gtggagccgt gcatacccgg gggctggact ttgcctgcga tatctacatt    960
tgggccccgc tggccggcac ttgcggcgtg ctcctgctgt cgctggtcat cacccttac   1020 tgcaagaggg gccggaagaa gctgctttac atcttcaagc agccgttcat gcggcccgtg   1080
cagacgactc aggaagagga cggatgctcg tgcagattcc ctgaggagga agaggggga   1140 tgcgaactgc gcgtcaagtt ctcacggtcc gccgacgccc ccgcatatca acagggccag   1200
aatcagctct acaacgagct gaacctggga aggagagagg agtacgacgt gctggacaag   1260
cgacgcggac gcgacccgga gatggggggg aaaccacggc ggaaaaaccc tcaggaagga   1320
ctgtacaacg aactccagaa agacaagatg gcggaagcct actcagaaat cgggatgaag   1380
ggagagcgga ggaggggaaa gggtcacgac gggctgtacc agggactgag caccgccact   1440
aaggatacct acgatgcctt gcatatgcaa gcactcccac cccgg                 1485
```

<210> SEQ ID NO 96
<211> LENGTH: 495
<212> TYPE: PRT
<213> ORGANISM: Artificial Sequence
<220> FEATURE:
<223> OTHER INFORMATION: LTG 2080 (hScFv aCD123 CD8 TM 4-1BB CD3 zeta)

<400> SEQUENCE: 96

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ala Thr Val Lys Ile Ser Cys Lys Val Ser Gly
        35                  40                  45

Tyr Thr Phe Thr Asp Tyr Tyr Met His Trp Val Gln Gln Ala Pro Gly
    50                  55                  60

Lys Gly Leu Glu Trp Ile Gly Leu Val Asp Pro Glu Asp Gly Glu Thr
65                  70                  75                  80

Ile Tyr Ala Glu Lys Phe Gln Gly Arg Val Thr Ile Thr Ala Asp Thr
                85                  90                  95

Ser Thr Asp Thr Ala Tyr Met Glu Leu Ser Ser Leu Arg Ser Glu Asp
            100                 105                 110

Thr Ala Val Tyr Tyr Cys Ala Thr Ala Pro Leu Gly Glu Val Gly Ala
        115                 120                 125

Ala Val Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser His Val
145                 150                 155                 160

Ile Leu Thr Gln Pro Pro Ser Val Ser Ala Ala Pro Gly Gln Glu Val
                165                 170                 175

Ser Ile Ser Cys Ser Gly Ser Asp Ala Asn Ile Gly Thr Asn Leu Val
            180                 185                 190

Ser Trp Tyr Gln His Val Pro Gly Thr Ala Pro Lys Leu Leu Ile Tyr
        195                 200                 205

Glu Asn Ser Lys Arg Pro Ser Gly Ile Pro Ala Arg Phe Ser Ser Ser
    210                 215                 220

Gln Ser Gly Thr Ser Ala Thr Leu Ala Ile Ser Gly Leu Gln Ser Gly
225                 230                 235                 240

Asp Glu Ala Ile Tyr Tyr Cys Leu Thr Trp Asp Arg Thr Leu Ser Gly
                245                 250                 255
```

```
Lys Ile Phe Gly Gly Gly Thr Gln Leu Thr Val Leu Gly Ala Ala Ala
            260                 265                 270

Thr Thr Thr Pro Ala Pro Arg Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
            355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 97
<211> LENGTH: 1488
<212> TYPE: DNA
<213> ORGANISM: Artificial Sequence
<220> FEATURE:
<223> OTHER INFORMATION: LTG 2081 (hScFv aCD123 CD8 TM 4-1BB CD3 zeta)

<400> SEQUENCE: 97
atgctgctgc tggtgaccag cctgctgctg tgcgaactgc cgcatccggc gtttctgctg      60
attccggaag tgcaacttgt ccaaagcgga gccgaagtga agaagccagg atcctccgtg     120
aaagtgtctt gcaaagcatc cggcggcact ttctcctcct acgccatctc ctgggtcaga     180
caggcgcctg gacagggtct ggagtggatg ggcattatca atcctagcgg tggctccact     240
tcgtatgccc agaagttcca gggtcgggtc accatgaccc gggatacttc aactagcacc     300
gtgtacatgg aactctcctc gctgcgctcg gacgatacca ccgtgtacta ctgtgcccgc     360
gagctgctct ggtttggaga gctggacacc tacgaatgga cgtctgggg acaggggacc     420 actgtgacgg tgtcgtcagg aggcggaggc tcaggagggg gtggttccgg aggggaggga     480
tccctcccgg tgctgaccca gcccccaagc gtcagcgtgg ctccgggaaa gaccgcccgc     540
atcacatgcg gcgggaacaa catcggctcc aagtccgtgc attggtacca gcagaagcct     600
ggacaagcgc cggtgctggt catctacgac gactcagatc ggccctccgg cattcccgag     660
cggttcagcg gctccaactc gggcaacact gctactctga ccatctcgag ggtggaagcg     720
```

```
ggggacgaag cagattacta ctgccaagtc tgggactcca gctccgacca cggggtgttc    780
ggcggaggaa cccagctgac cgtgttggga gcggccgcaa ctaccacccc tgcccctcgg    840
ccgccgactc cggccccaac catcgcaagc caacccctct ccttgcgccc gaagcttgc     900 cgcccggccg cgggtggagc cgtgcatacc cggggggctgg actttgcctg cgatatctac   960
atttgggccc cgctggccgg cacttgcggc gtgctcctgc tgtcgctggt catcacccTT   1020
tactgcaaga ggggccggaa gaagctgctt tacatcttca gcagccgtt catgcggccc    1080 gtgcagacga ctcaggaaga ggacggatgc tcgtgcagat ccctgagga ggaagagggg    1140 ggatgcgaac tgcgcgtcaa gttctcacgg tccgccgacg ccccgcata tcaacgggc     1200 cagaatcagc tctacaacga gctgaacctg gaaggagag aggagtacga cgtgctggac   1260
aagcgacgcg gacgcgaccc ggagatgggg gggaaaccac ggcggaaaaa ccctcaggaa   1320
ggactgtaca cgaactccca gaaagacaag atggcggaag cctactcaga aatcgggatg   1380 aaggagagc ggaggagggg aaagggtcac gacgggctgt accagggact gagcaccgcc    1440
actaaggata cctacgatgc cttgcatatg caagcactcc cacccccgg              1488
```

<210> SEQ ID NO 98
<211> LENGTH: 496
<212> TYPE: PRT
<213> ORGANISM: Artificial Sequence
<220> FEATURE:
<223> OTHER INFORMATION: LTG 2081 (hScFv aCD123 CD8 TM 4-1BB CD3 zeta)

<400> SEQUENCE: 98

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Ile Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Asp Asp
            100                 105                 110

Thr Ala Val Tyr Tyr Cys Ala Arg Glu Leu Leu Trp Phe Gly Glu Leu
        115                 120                 125

Asp Thr Tyr Gly Met Asp Val Trp Gly Gln Gly Thr Thr Val Thr Val
    130                 135                 140

Ser Ser Gly Gly Gly Gly Ser Gly Gly Gly Gly Ser Gly Gly Gly Gly
145                 150                 155                 160

Ser Leu Pro Val Leu Thr Gln Pro Pro Ser Val Ser Val Ala Pro Gly
                165                 170                 175

Lys Thr Ala Arg Ile Thr Cys Gly Gly Asn Asn Ile Gly Ser Lys Ser
            180                 185                 190

Val His Trp Tyr Gln Gln Lys Pro Gly Gln Ala Pro Val Leu Val Ile
        195                 200                 205

Tyr Asp Asp Ser Asp Arg Pro Ser Gly Ile Pro Glu Arg Phe Ser Gly
    210                 215                 220
```

```
Ser Asn Ser Gly Asn Thr Ala Thr Leu Thr Ile Ser Arg Val Glu Ala
225                 230                 235                 240

Gly Asp Glu Ala Asp Tyr Tyr Cys Gln Val Trp Asp Ser Ser Ser Asp
            245                 250                 255

His Gly Val Phe Gly Gly Gly Thr Gln Leu Thr Val Leu Gly Ala Ala
        260                 265                 270

Ala Thr Thr Thr Pro Ala Pro Arg Pro Pro Thr Pro Ala Pro Thr Ile
    275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
            325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
            355                 360                 365

Gly Cys Ser Cys Arg Phe Pro Glu Glu Glu Glu Gly Gly Cys Glu Leu
370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 99
<211> LENGTH: 1476
<212> TYPE: DNA
<213> ORGANISM: Artificial Sequence
<220> FEATURE:
<223> OTHER INFORMATION: LTG 2082 (hScFv aCD123 CD8 TM 4-1BB CD3 zeta)

<400> SEQUENCE: 99

```
atgctgctgc tggtgaccag cctgctgctg tgcgaactgc cgcatccggc gtttctgctg      60
attccggaag tgcaactcgt ccaatctggt gccgaagtca agaagcctgg ctcaagcgtg     120
aaagtgtcct gcaaagcgtc gggagggacc ttcagctcct acgccatttc ctgggtccgc     180
caagcaccag acagggcct ggagtggatg ggcggcatca tcccgatctt cgggactgcc      240
aactacgccc agaagttcca ggggagagtg accattaccg ccgacgagtc gaccagcacg     300
gcctacatgg aactgtccag cctgcgctcc gaggacactg ccgtgtacta ctgcgcgagg     360
gccagactcg gtggagcgtt cgacatctgg ggacagggca ccatggtcac cgtgtcatcc     420
ggtggcggag gatccggtgg tggcggatca ggaggggag atcccagtc cgtgctgact      480 cagcctccct ccgtgagcgc tgcaccggga cagaaggtca ccatctcatg ctcggggga     540
```

```
agctccaaca tcgggaacca ctacgtgtcc tggtaccaac agttgcctgg tgccgctcca    600
aagctgctga tctatgacga taacaagcgg ccgtccggaa tccccgaccg gttctcgggg    660
tctagatccg gaaccagcgc aactctcggc attaccggac tgcagagcgg cgatgaggcc    720
gactactact gtggcacatg ggactcgtcg ctggctgccc acgtgtttgg cactggcacc    780
aaggtcaccg tgcttggagc ggccgcaact accaccctg cccctcggcc gccgactccg    840
gccccaacca tcgcaagcca acccctctcc ttgcgcccg aagcttgccg ccggccgcg     900 ggtggagccg tgcataccg ggggctggac tttgcctgcg atatctacat ttgggccccg    960
ctggccggca cttgcggcgt gctcctgctg tcgctggtca tcacccttta ctgcaagagg   1020
ggccggaaga agctgcttta catcttcaag cagccgttca tgcggcccgt gcagacgact   1080
caggaagagg acggatgctc gtgcagattc cctgaggagg aagaggggg atgcgaactg    1140 cgcgtcaagt tctcacggtc cgccgacgcc cccgcatatc aacagggcca gaatcagctc   1200
tacaacgagc tgaacctggg aaggagagag gagtacgacg tgctggacaa gcgacgcgga   1260
cgcgacccgg agatgggggg gaaaccacg cggaaaaacc tcaggaagg actgtacaac    1320 gaactccaga agacaagat ggcggaagcc tactcagaaa tcgggatgaa gggagagcgg    1380
aggaggggaa agggtcacga cgggctgtac cagggactga gcaccgccac taaggatacc   1440
tacgatgcct tgcatatgca agcactccca ccccgg                            1476

<210> SEQ ID NO 100
<211> LENGTH: 492
<212> TYPE: PRT
<213> ORGANISM: Artificial Sequence
<220> FEATURE:
<223> OTHER INFORMATION: LTG 2082 (hScFv aCD123 CD8 TM 4-1BB CD3 zeta)

<400> SEQUENCE: 100

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Ala Arg Leu Gly Gly Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Gly Ser Ser Asn Ile Gly Asn His Tyr Val Ser Trp Tyr
            180                 185                 190

Gln Gln Leu Pro Gly Ala Ala Pro Lys Leu Leu Ile Tyr Asp Asp Asn
```

```
                195                 200                 205
Lys Arg Pro Ser Gly Ile Pro Asp Arg Phe Ser Gly Ser Arg Ser Gly
            210                 215                 220

Thr Ser Ala Thr Leu Gly Ile Thr Gly Leu Gln Ser Gly Asp Glu Ala
225                 230                 235                 240

Asp Tyr Tyr Cys Gly Thr Trp Asp Ser Ser Leu Ala Ala His Val Phe
                245                 250                 255

Gly Thr Gly Thr Lys Val Thr Val Leu Gly Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 101
<211> LENGTH: 1491
<212> TYPE: DNA
<213> ORGANISM: Artificial Sequence
<220> FEATURE:
<223> OTHER INFORMATION: LTG 2083 (hScFv aCD123 CD8 TM 4-1BB CD3 zeta)

<400> SEQUENCE: 101
atgctgctgc tggtgaccag cctgctgctg tgcgaactgc cgcatccggc gtttctgctg      60
attccggaag tgcaacttgt ccagagcgga gccgaagtga agaaacctgg atcctccgtc     120
aaagtgtcgt gcaaggcttc gggcggaacc ttctcctcgt acgcgatctc atgggtcaga     180
caggcacccg acagggact  ggagtggatg gcggcatca ttcccatctt cggcaccgct     240
aattacgccc agaagtttca ggggagagtg accatcaccg ccgacgagtc cacctccact     300
gcctacatgg aactgtcctc actgaggtcc gaggatactg ccgtgtacta ctgcgcgtcg     360 caaaagggg gtggatggtc cattgacgcc ttcgatattt ggggacaggg gacgatggtc     420
```

```
acagtgtcat ccggcggtgg tggatccggt ggtggcggat ccggaggagg aggcagccag    480
tccgtgctga cccagccgcc tagcgtgtcg gccgcatctg ggcagcgcgt gaccatttcc    540
tgttccgggt cctcgtccaa catcggcaac aactacgcct cctggtacca acagctcccg    600
ggaatggccc ctaagctgct gatctacgag gacaacaagc ggccatccgg gatctcagac    660
cggttcagcg gatcccagtc cggcacttcc gcgagcctcg ccatcaccgg actgcaggct    720
gaggacgaag ccgactacta ctgccaatca tatgacagct cgctcagcgg cgatgtggtg    780
ttcggcggtg gcactaagct gaccgtgttg ggagcggccg caactaccac ccctgcccct    840
cggccgccga ctccggcccc aaccatcgca agccaacccc tctccttgcg ccccgaagct    900
tgccgcccgg ccgcgggtgg agccgtgcat acccgggggc tggactttgc ctgcgatatc    960
tacatttggg ccccgctggc cggcacttgc ggcgtgctcc tgctgtcgct ggtcatcacc   1020
ctttactgca agagggccg gaagaagctg ctttacatct tcaagcagcc gttcatgcgg   1080
cccgtgcaga cgactcagga agaggacgga tgctcgtgca gattccctga ggaggaagag   1140
gggggatgcg aactgcgcgt caagttctca cggtccgccg acgcccccgc atatcaacag   1200
ggccagaatc agctctacaa cgagctgaac ctgggaagga gagaggagta cgacgtgctg   1260
gacaagcgac gcggacgcga cccggagatg gggggggaaac cacggcggaa aaaccctcag   1320
gaaggactgt acaacgaact ccagaaagac aagatggcgg aagcctactc agaaatcggg   1380
atgaagggag agcggaggag gggaaagggt cacgacgggc tgtaccaggg actgagcacc   1440
gccactaagg atacctacga tgccttgcat atgcaagcac tcccaccccg g             1491
```

<210> SEQ ID NO 102
<211> LENGTH: 497
<212> TYPE: PRT
<213> ORGANISM: Artificial Sequence
<220> FEATURE:
<223> OTHER INFORMATION: LTG 2083 (hScFv aCD123 CD8 TM 4-1BB CD3 zeta)

<400> SEQUENCE: 102

```
Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Ala Glu
                20                  25                  30

Val Lys Lys Pro Gly Ser Ser Val Lys Val Ser Cys Lys Ala Ser Gly
            35                  40                  45

Gly Thr Phe Ser Ser Tyr Ala Ile Ser Trp Val Arg Gln Ala Pro Gly
        50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Ser Gln Lys Gly Gly Gly Trp Ser Ile
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Ser Gly Gly Gly Ser Gln
145                 150                 155                 160

Ser Val Leu Thr Gln Pro Pro Ser Val Ser Ala Ala Ser Gly Gln Arg
                165                 170                 175
```

```
Val Thr Ile Ser Cys Ser Gly Ser Ser Asn Ile Gly Asn Asn Tyr
            180                 185                 190

Ala Ser Trp Tyr Gln Gln Leu Pro Gly Met Ala Pro Lys Leu Leu Ile
        195                 200                 205

Tyr Glu Asp Asn Lys Arg Pro Ser Gly Ile Ser Asp Arg Phe Ser Gly
    210                 215                 220

Ser Gln Ser Gly Thr Ser Ala Ser Leu Ala Ile Thr Gly Leu Gln Ala
225                 230                 235                 240

Glu Asp Glu Ala Asp Tyr Tyr Cys Gln Ser Tyr Asp Ser Ser Leu Ser
                245                 250                 255

Gly Asp Val Val Phe Gly Gly Gly Thr Lys Leu Thr Val Leu Gly Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 103
<211> LENGTH: 1473
<212> TYPE: DNA
<213> ORGANISM: Artificial Sequence
<220> FEATURE:
<223> OTHER INFORMATION: LTG 2084 (hScFv aCD123 CD8 TM 4-1BB CD3 zeta)

<400> SEQUENCE: 103
atgctgctgc tggtgaccag cctgctgctg tgcgaactgc cgcatccggc gtttctgctg      60
attccggaag tccaactcgt ccaaagcggt gcagaagtga aaaagccagg ctcctcagtg     120
aaagtgtcct gcaaagcctc gggggggaac ttctcctcct acgccatctc ctgggtccgc     180
```

```
caagcaccag  gacagggcct  ggagtggatg  ggcgggatca  ttccgatctt  cggcaccgcc    240
aactacgccc  agaagtttca  gggccgcgtg  actatcaccg  ccgacgagtc  cacctccact    300
gcgtacatgg  aactgtccag  cctgcggtcc  gaggacactg  ccgtgtatta  ctgcgcgaga    360
gtcggttgct  ccgggggatc  gtgttatccc  gactactggg  gacaggggac  cctcgtgacc    420
gtgtcgtcgg  gtggtggtgg  aagcggcggt  ggaggatccg  gtggaggagg  cagcgaaatc    480
gtgctgactc  agtcgccgtc  ctcgctttcc  gcctccgtgg  gagatcgcgt  gaccatcacg    540
tgtcaggctt  ctcaagacat  tagcaactac  ctgaattggt  accagcagaa  gcctggaaag    600
gctccgaagc  tgctcatcta  cgacgcgtcc  aacctggaga  cagggtgcc   ttcacggttc    660
tcgggaagcg  gatccggcac  cgatttcacc  ttcaccattt  caagcctgca  acccgaggat    720
attgccacct  actactgcca  gcagtacgac  aaccteccec  tgactttcgg  gggcggcact    780
aagttggaca  tcaaggcggc  cgcaactacc  accectgccc  ctcggccgcc  gactccggcc    840
ccaaccatcg  caagccaacc  cctctccttg  cgccccgaag  cttgccgccc  ggccgcgggt    900
ggagccgtgc  atacccgggg  gctggacttt  gcctgcgata  tctacatttg  ggccccgctg    960
gccggcactt  gcggcgtgct  cctgctgtcg  ctggtcatca  cccctttactg  caagagggc   1020
cggaagaagc  tgctttacat  cttcaagcag  ccgttcatgc  ggcccgtgca  gacgactcag   1080
gaagaggacg  gatgctcgtg  cagattccct  gaggaggaag  agggggggatg  cgaactgcgc  1140
gtcaagttct  cacggtccgc  cgacgccccc  gcatatcaac  agggccagaa  tcagctctac   1200
aacgagctga  acctgggaag  gagagaggag  tacgacgtgc  tggacaagcg  acgcggacgc   1260
gacccggaga  tggggggggaa  accacggcgg  aaaaaccctc  aggaaggact  gtacaacgaa  1320
ctccagaaag  acaagatggc  ggaagcctac  tcagaaatcg  ggatgaaggg  agagcggagg   1380
aggggaaagg  gtcacgacgg  gctgtaccag  ggactgagca  ccgccactaa  ggataccctac  1440
gatgccttgc  atatgcaagc  actcccaccc  cgg                                 1473
```

<210> SEQ ID NO 104
<211> LENGTH: 491
<212> TYPE: PRT
<213> ORGANISM: Artificial Sequence
<220> FEATURE:
<223> OTHER INFORMATION: LTG 2084 (hScFv aCD123 CD8 TM 4-1BB CD3 zeta)

<400> SEQUENCE: 104

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Val Gly Cys Ser Gly Gly Ser Cys
        115                 120                 125

Tyr Pro Asp Tyr Trp Gly Gln Gly Thr Leu Val Thr Val Ser Ser Gly
```

Gly Gly Gly Ser Gly Gly Gly Ser Gly Gly Gly Ser Glu Ile
145                 150                 155                 160

Val Leu Thr Gln Ser Pro Ser Leu Ser Ala Ser Val Gly Asp Arg
                165                 170                 175

Val Thr Ile Thr Cys Gln Ala Ser Gln Asp Ile Ser Asn Tyr Leu Asn
            180                 185                 190

Trp Tyr Gln Gln Lys Pro Gly Lys Ala Pro Lys Leu Leu Ile Tyr Asp
                195                 200                 205

Ala Ser Asn Leu Glu Thr Gly Val Pro Ser Arg Phe Ser Gly Ser Gly
210                 215                 220

Ser Gly Thr Asp Phe Thr Phe Thr Ile Ser Ser Leu Gln Pro Glu Asp
225                 230                 235                 240

Ile Ala Thr Tyr Tyr Cys Gln Gln Tyr Asp Asn Leu Pro Leu Thr Phe
                245                 250                 255

Gly Gly Gly Thr Lys Leu Asp Ile Lys Ala Ala Ala Thr Thr Thr Pro
                260                 265                 270

Ala Pro Arg Pro Pro Thr Pro Ala Pro Thr Ile Ala Ser Gln Pro Leu
                275                 280                 285

Ser Leu Arg Pro Glu Ala Cys Arg Pro Ala Ala Gly Gly Ala Val His
290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
                355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 105
<211> LENGTH: 1479
<212> TYPE: DNA
<213> ORGANISM: Artificial Sequence
<220> FEATURE:
<223> OTHER INFORMATION: LTG 2085 (hScFv aCD123 CD8 TM 4-1BB CD3 zeta)

<400> SEQUENCE: 105
atgctgctgc tggtgaccag cctgctgctg tgcgaactgc cgcatccggc gtttctgctg      60

```
attccgcaag tccagttgca acaatgggga gcaggccttc tgaaaccgtc cgagacactg      120
agcctgacgt gcgccgtcta tggcggatcg ttctccggat actactggtc gtggatcaga      180
cagcctccgg gaaagggtct ggaatggatc ggcgaaatca accacagcgg cagcaccaat      240
tacaacccgt cactgaagtc aagggtcacc attagcgtgg acacttccaa gaaccagttc      300
tccctgaaac tgtcgagcgt gaccgctgcc gatactgccg tgtactactg cccgcggc        360
caagtcaagt atagctcaag cctcggctac tggggccagg gaaccctcgt gaccgtgtcc      420
tcgggtggag gaggctccgg tggtggagga tccggtggcg aggatcgca gtccgtgctg       480
acccagcctc cctccgtgtc tgctgcccct gggcaaaagg tcaccatttc gtgctccggc      540
tcatcgtcca acatcgggaa caactttgtg tcctggtacc agcagctgcc cggtactgcc      600
ccaaagctgc tgatctacga ggacaacaag cgcccatccg ggattccgga tcggttcagc      660
ggatcacggt ccggaactag cgcgaccctg ggatcaccg gctccagac tggcgacgaa        720
gcggactact actgcggaac ttgggactcc tccttggggg cctgggtgtt cggcggaggg      780
accaagctca ccgtgcttgg agcggccgca actaccaccc ctgcccctcg ccgccgact       840
ccggccccaa ccatcgcaag ccaacccctc tccttgcgcc ccgaagcttg ccgcccggcc      900
gcgggtggag ccgtgcatac ccgggggctg gactttgcct gcgatatcta catttgggcc      960
ccgctggccg gcacttgcgg cgtgctcctg ctgtcgctgg tcatcaccct ttactgcaag     1020
agggccggaa gaagctgct ttacatcttc aagcagccgt tcatgcggcc cgtgcagacg      1080
actcaggaag aggacggatg ctcgtgcaga ttccctgagg aggaagaggg gggatgcgaa     1140
ctgcgcgtca gttctcacg gtccgccgac gccccgcat atcaacaggg ccagaatcag       1200
ctctacaacg agctgaacct gggaaggaga gaggagtacg acgtgctgga caagcgacgc     1260
ggacgcgacc cggagatggg ggggaaacca cggcggaaaa accctcagga aggactgtac     1320
aacgaactcc agaaagacaa gatggcggaa gcctactcag aaatcgggat gaagggagag     1380
cggaggaggg gaaagggtca cgacgggctg taccaggac tgagcaccgc cactaaggat      1440
acctacgatg ccttgcatat gcaagcactc ccacccccgg                           1479
```

<210> SEQ ID NO 106
<211> LENGTH: 493
<212> TYPE: PRT
<213> ORGANISM: Artificial Sequence
<220> FEATURE:
<223> OTHER INFORMATION: LTG 2085 (hScFv aCD123 CD8 TM 4-1BB CD3 zeta)

<400> SEQUENCE: 106

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Trp Gly Ala Gly
            20                  25                  30

Leu Leu Lys Pro Ser Glu Thr Leu Ser Leu Thr Cys Ala Val Tyr Gly
        35                  40                  45

Gly Ser Phe Ser Gly Tyr Tyr Trp Ser Trp Ile Arg Gln Pro Pro Gly
    50                  55                  60

Lys Gly Leu Glu Trp Ile Gly Glu Ile Asn His Ser Gly Ser Thr Asn
65                  70                  75                  80

Tyr Asn Pro Ser Leu Lys Ser Arg Val Thr Ile Ser Val Asp Thr Ser
                85                  90                  95

Lys Asn Gln Phe Ser Leu Lys Leu Ser Ser Val Thr Ala Ala Asp Thr
            100                 105                 110
```

-continued

Ala Val Tyr Tyr Cys Ala Arg Gly Gln Val Lys Tyr Ser Ser Ser Leu
            115                 120                 125

Gly Tyr Trp Gly Gln Gly Thr Leu Val Thr Val Ser Ser Gly Gly Gly
130                 135                 140

Gly Ser Gly Gly Gly Ser Gly Gly Gly Ser Gln Ser Val Leu
145                 150                 155                 160

Thr Gln Pro Pro Ser Val Ser Ala Ala Pro Gly Gln Lys Val Thr Ile
                    165                 170                 175

Ser Cys Ser Gly Ser Ser Ser Asn Ile Gly Asn Asn Phe Val Ser Trp
                180                 185                 190

Tyr Gln Gln Leu Pro Gly Thr Ala Pro Lys Leu Leu Ile Tyr Glu Asp
            195                 200                 205

Asn Lys Arg Pro Ser Gly Ile Pro Asp Arg Phe Ser Gly Ser Arg Ser
        210                 215                 220

Gly Thr Ser Ala Thr Leu Gly Ile Thr Gly Leu Gln Thr Gly Asp Glu
225                 230                 235                 240

Ala Asp Tyr Tyr Cys Gly Thr Trp Asp Ser Ser Leu Gly Ala Trp Val
                    245                 250                 255

Phe Gly Gly Gly Thr Lys Leu Thr Val Leu Gly Ala Ala Ala Thr Thr
                260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                    325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
            355                 360                 365

Cys Arg Phe Pro Glu Glu Glu Gly Gly Cys Glu Leu Arg Val Lys
        370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                    405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
        450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                    485                 490

<210> SEQ ID NO 107
<211> LENGTH: 1461
<212> TYPE: DNA
<213> ORGANISM: Artificial Sequence
<220> FEATURE:

<223> OTHER INFORMATION: LTG 2086 (hScFv aCD123 CD8 TM 4-1BB CD3 zeta)

<400> SEQUENCE: 107

```
atgctgctgc tggtgaccag cctgctgctg tgcgaactgc cgcatccggc gtttctgctg      60
attccggaag tgcagttggt ggagagcggt ggaggacttg tgcaacctgg tggatccctg     120
agattgtcgt gcgcagcttc agggttcacc ttctcctcct acgccatgca ctgggtccgc     180
caagcaccag aaagggcct ggaatgggtc agctccatct cctcgtcgtc ctcgtacatc     240
tactatgccg actccgtgaa gggccgcttc accattagcc gggacaactc aaagaacact     300
ctgtaccttc aaatgaactc cctgcgggct gaagataccg ccgtgtacta ctgcgcgagg     360
gattgggatg acgcgttcga catttggggc caggggacta ccgtcaccgt gtcgtcgggt     420
ggaggaggat ccggggggtgg aggatcggga ggggtggaa gcgacattca gatgactcag     480
agcccgtcct ccctgtcggc ctcagtgggc gacagagtga ccatcacctg tcaagccagc     540
caggacatct caaactacct gaactggtac cagcagaagc ccggaaaggc ccctaagctg     600
ctcatctacg acgcctccaa cctggagact ggagtgccct acggttttc cggctctgga     660
agcggcaccg atttcacctt cacgatctcc tccctgcaac cggaagatat cgcgacctac     720
tactgccagc agtatgacaa tctcccgctc accttcggtg cggcactaa gctcgagatc     780
aaagcggccg caactaccac ccctgcccct cggccgccga ctccggcccc aaccatcgca     840
agccaacccc tctccttgcg ccccgaagct tgccgcccgg ccgcgggtgg agccgtgcat     900
acccgggggc tggactttgc ctgcgatatc tacatttggg ccccgctggc cggcacttgc     960
ggcgtgctcc tgctgtcgct ggtcatcacc ctttactgca gaggggccg gaagaagctg    1020
ctttacatct tcaagcagcc gttcatgcgg cccgtgcaga cgactcagga agaggacgga    1080
tgctcgtgca gattccctga ggaggaagag ggggatgcg aactgcgcgt caagttctca    1140
cggtccgccg acgcccccgc atatcaacag gccagaatc agctctacaa cgagctgaac    1200
ctgggaagga gagaggagta cgacgtgctg gacaagcgac gcggacgcga cccggagatg    1260
ggggggaaac cacggcggaa aaaccctcag gaaggactgt acaacgaact ccagaaagac    1320
aagatggcgg aagcctactc agaaatcggg atgaagggag agcggaggag gggaaagggt    1380
cacgacgggc tgtaccaggg actgagcacc gccactaagg ataccctacga tgccttgcat    1440
atgcaagcac tcccaccccg g                                              1461
```

<210> SEQ ID NO 108
<211> LENGTH: 487
<212> TYPE: PRT
<213> ORGANISM: Artificial Sequence
<220> FEATURE:
<223> OTHER INFORMATION: LTG 2086 (hScFv aCD123 CD8 TM 4-1BB CD3 zeta)

<400> SEQUENCE: 108

```
Met Leu Leu Leu Val Thr Ser Leu Leu Leu Cys Glu Leu Pro His Pro
  1               5                  10                  15

Ala Phe Leu Leu Ile Pro Glu Val Gln Leu Val Glu Ser Gly Gly Gly
             20                  25                  30

Leu Val Gln Pro Gly Gly Ser Leu Arg Leu Ser Cys Ala Ala Ser Gly
         35                  40                  45

Phe Thr Phe Ser Ser Tyr Ala Met His Trp Val Arg Gln Ala Pro Gly
     50                  55                  60

Lys Gly Leu Glu Trp Val Ser Ser Ile Ser Ser Ser Ser Tyr Ile
 65                  70                  75                  80
```

```
Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Asp Trp Asp Ala Phe Asp Ile
            115                 120                 125

Trp Gly Gln Gly Thr Thr Val Thr Val Ser Ser Gly Gly Gly Ser
        130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Gln Ala Ser Gln Asp Ile Ser Asn Tyr Leu Asn Trp Tyr Gln Gln
            180                 185                 190

Lys Pro Gly Lys Ala Pro Lys Leu Leu Ile Tyr Asp Ala Ser Asn Leu
            195                 200                 205

Glu Thr Gly Val Pro Ser Arg Phe Ser Gly Ser Gly Ser Gly Thr Asp
            210                 215                 220

Phe Thr Phe Thr Ile Ser Ser Leu Gln Pro Glu Asp Ile Ala Thr Tyr
225                 230                 235                 240

Tyr Cys Gln Gln Tyr Asp Asn Leu Pro Leu Thr Phe Gly Gly Gly Thr
                245                 250                 255

Lys Leu Glu Ile Lys Ala Ala Ala Thr Thr Thr Pro Ala Pro Arg Pro
            260                 265                 270

Pro Thr Pro Ala Pro Thr Ile Ala Ser Gln Pro Leu Ser Leu Arg Pro
            275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 109
<211> LENGTH: 1467
<212> TYPE: DNA
<213> ORGANISM: Artificial Sequence
<220> FEATURE:
<223> OTHER INFORMATION: LTG 2087 (hScFv aCD123 CD8 TM 4-1BB CD3 zeta)

<400> SEQUENCE: 109

```
atgctgctgc tggtgaccag cctgctgctg tgcgaactgc cgcatccggc gtttctgctg      60
attccgcaag tccaactcgt cgaaactggt ggtggcctcg tgaagcctgg aggatccctg     120
cgcctttcct gtgccgcttc cggctttact ttctcgtcgt actccatgaa ctgggtcaga     180
caggctcccg gaaagggcct ggaatgggtg tcctccatct cgtcctcatc ctcctacatc     240
tattacgcgg actccgtgaa gggcagattc accatttccc gggacaacgc caagaacagc     300
ttgtacctcc aaatgaactc cctgcgggca gaggacaccg ccgtgtacta ctgcgcgagg     360
gatgggatt tctggagcgg agccatcgac tactggggcc agggaactct cgtgaccgtc     420
agctccggtg gtggtggaag cggaggcgga ggttctgggg gggaggatc agacattcag     480
ctgacccagt cgccatcctc cctgagcgcc tcagtggggg accgcgtgac tattacatgc     540
caggcctccc aagatatctc gaactacctg aactggtatc agcagaagcc tggaaaggcc     600
ccgaagctgt tgatctacga tgccagcaac ctggagactg gggtgccttc ccggttctcg     660
ggatcaggct cgggcaccga tttcaccttc acgatcagca gcctgcagcc cgaggacatt     720
gcaacctact actgccagca gtacgacaat ctgccgcttt tgggggagg caccaagctg     780
gaaatcaaag cggccgcaac taccacccct gcccctcggc cgccgactcc ggccccaacc     840
atcgcaagcc aaccctctc cttgcgcccc gaagcttgcc gccggccgc gggtggagcc     900
gtgcatatccc gggggctgga cttttgcctgc gatatctaca tttgggcccc gctggccggc     960
acttgcggcg tgctcctgct gtcgctggtc atcacccttt actgcaagag gggccggaag    1020
aagctgcttt acatcttcaa gcagccgttc atgcggcccg tgcagacgac tcaggaagag    1080
gacggatgct cgtgcagatt ccctgaggag aagaggggg gatgcgaact gcgcgtcaag    1140
ttctcacggt ccgccgacgc ccccgcatat caacagggcc agaatcagct ctacaacgag    1200
ctgaacctgg aaggagaga ggagtacgac gtgctggaca gcgacgcgg acgcgacccg    1260
gagatggggg ggaaaccacg gcggaaaaac cctcaggaag gactgtacaa cgaactccag    1320
aaagacaaga tggcggaagc ctactcagaa atcgggatga agggagagcg gaggagggga    1380
aagggtcacg acgggctgta ccagggactg agcaccgcca ctaaggatac ctacgatgcc    1440
ttgcatatgc aagcactccc accccgg                                         1467
```

<210> SEQ ID NO 110
<211> LENGTH: 489
<212> TYPE: PRT
<213> ORGANISM: Artificial Sequence
<220> FEATURE:
<223> OTHER INFORMATION: LTG 2087 (hScFv aCD123 CD8 TM 4-1BB CD3 zeta)

<400> SEQUENCE: 110

```
Met Leu Leu Leu Val Thr Ser Leu Leu Cys Glu Leu Pro His Pro
1               5                   10                  15

Ala Phe Leu Leu Ile Pro Gln Val Gln Leu Val Glu Thr Gly Gly Gly
            20                  25                  30

Leu Val Lys Pro Gly Gly Ser Leu Arg Leu Ser Cys Ala Ala Ser Gly
        35                  40                  45

Phe Thr Phe Ser Ser Tyr Ser Met Asn Trp Val Arg Gln Ala Pro Gly
```

```
            50                  55                  60
Lys Gly Leu Glu Trp Val Ser Ser Ile Ser Ser Ser Ser Tyr Ile
 65                  70                  75                  80

Tyr Tyr Ala Asp Ser Val Lys Gly Arg Phe Thr Ile Ser Arg Asp Asn
                     85                  90                  95

Ala Lys Asn Ser Leu Tyr Leu Gln Met Asn Ser Leu Arg Ala Glu Asp
                    100                 105                 110

Thr Ala Val Tyr Tyr Cys Ala Arg Asp Gly Asp Phe Trp Ser Gly Ala
                    115                 120                 125

Ile Asp Tyr Trp Gly Gln Gly Thr Leu Val Thr Val Ser Ser Gly Gly
            130                 135                 140

Gly Gly Ser Gly Gly Gly Ser Gly Gly Gly Ser Asp Ile Gln
145                 150                 155                 160

Leu Thr Gln Ser Pro Ser Ser Leu Ser Ala Ser Val Gly Asp Arg Val
                    165                 170                 175

Thr Ile Thr Cys Gln Ala Ser Gln Asp Ile Ser Asn Tyr Leu Asn Trp
                    180                 185                 190

Tyr Gln Gln Lys Pro Gly Lys Ala Pro Lys Leu Leu Ile Tyr Asp Ala
            195                 200                 205

Ser Asn Leu Glu Thr Gly Val Pro Ser Arg Phe Ser Gly Ser Gly Ser
210                 215                 220

Gly Thr Asp Phe Thr Phe Thr Ile Ser Ser Leu Gln Pro Glu Asp Ile
225                 230                 235                 240

Ala Thr Tyr Tyr Cys Gln Gln Tyr Asp Asn Leu Pro Leu Phe Gly Gly
                    245                 250                 255

Gly Thr Lys Leu Glu Ile Lys Ala Ala Ala Thr Thr Thr Pro Ala Pro
                    260                 265                 270

Arg Pro Pro Thr Pro Ala Pro Thr Ile Ala Ser Gln Pro Leu Ser Leu
                    275                 280                 285

Arg Pro Glu Ala Cys Arg Pro Ala Ala Gly Gly Ala Val His Thr Arg
            290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                    325                 330                 335

Arg Gly Arg Lys Lys Leu Leu Tyr Ile Phe Lys Gln Pro Phe Met Arg
                    340                 345                 350

Pro Val Gln Thr Thr Gln Glu Glu Asp Gly Cys Ser Cys Arg Phe Pro
                    355                 360                 365

Glu Glu Glu Glu Gly Gly Cys Glu Leu Arg Val Lys Phe Ser Arg Ser
            370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                    405                 410                 415

Gly Arg Asp Pro Glu Met Gly Gly Lys Pro Arg Arg Lys Asn Pro Gln
                    420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480
```

Leu His Met Gln Ala Leu Pro Pro Arg
           485

<210> SEQ ID NO 111
<211> LENGTH: 1467
<212> TYPE: DNA
<213> ORGANISM: Artificial Sequence
<220> FEATURE:
<223> OTHER INFORMATION: LTG 2088 (hScFv aCD123 CD8 TM 4-1BB CD3 zeta)

<400> SEQUENCE: 111

| | | |
|---|---|---|
| atgctgctgc tggtgaccag cctgctgctg tgcgaactgc cgcatccggc gtttctgctg | 60 |
| attccggagg tgcaattggt gcagtcaggt ggtggagtgg tgcagccagg aagatccctt | 120 |
| agactctcgt gtgcggcgtc aggctttacc ttctcctcgt actccatgaa ctgggtcaga | 180 |
| caggcaccgg gaaagggact ggaatgggtg tcctccatct cgtcctcctc ctcctacatc | 240 |
| tactacgccg atagcgtgaa gggccggttc accatttcgc gcgacaacgc caagaacacc | 300 |
| ctgtacctcc aaatgaattc gctgcgggcc gaagataccc tgtctattac tgcgcccgc | 360 |
| gacaactggg gctcgctgga ctattggggc cagggaaccc tcgtcaccgt gtcaagcgga | 420 |
| gggggtggat ccggaggcgg aggatccggt ggagggggaa gcgacattca gatgactcag | 480 |
| agcccgtcct ccctgtctgc ctccgtgggg gatcgcgtga ccatcacatg ccaggcctca | 540 |
| caagacatca gcaattacct gaactggtac cagcagaagc ctggaaaggc ccccaagctg | 600 |
| ctgatctacg atgccagcaa cctggagact ggggtgcctt caaggttctc cggttccgga | 660 |
| agcggcactg acttcacctt cactatctcg agcctgcaac ccgaggacat tgccacctac | 720 |
| tactgccagc agtacgacaa ccttccgcac atgtacacgt tcggccaggg caccaagctc | 780 |
| gaaatcaaag cggccgcaac taccacccct gccctcggc gccgactcc ggcccccaacc | 840 |
| atcgcaagcc aaccctctc cttgcgcccc gaagcttgcc gcccggccgc gggtggagcc | 900 |
| gtgcataccc gggggctgga ctttgcctgc gatatctaca tttgggcccc gctggccggc | 960 |
| acttgcggcg tgctcctgct gtcgctggtc atcacccttt actgcaagag gggccggaag | 1020 |
| aagctgcttt acatcttcaa gcagccgttc atgcggcccg tgcagacgac tcaggaagag | 1080 |
| gacggatgct cgtgcagatt ccctgaggag aagagggggg gatgcgaact gcgcgtcaag | 1140 |
| ttctcacggt ccgccgacgc ccccgcatat aacagggcc agaatcagct ctacaacgag | 1200 |
| ctgaacctgg aaggagaga ggagtacgac gtgctggaca agcgacgcgg acgcgacccg | 1260 |
| gagatggggg ggaaaccacg gcggaaaaac cctcaggaag gactgtacaa cgaactccag | 1320 |
| aaagacaaga tggcggaagc ctactcagaa atcgggatga agggagagcg gaggaggga | 1380 |
| aagggtcacg acgggctgta ccagggactg agcaccgcca ctaaggatac ctacgatgcc | 1440 |
| ttgcatatgc aagcactccc accccgg | 1467 |

<210> SEQ ID NO 112
<211> LENGTH: 489
<212> TYPE: PRT
<213> ORGANISM: Artificial Sequence
<220> FEATURE:
<223> OTHER INFORMATION: LTG 2088 (hScFv aCD123 CD8 TM 4-1BB CD3 zeta)

<400> SEQUENCE: 112

Met Leu Leu Leu Val Thr Ser Leu Leu Cys Glu Leu Pro His Pro
1               5                   10                  15

Ala Phe Leu Leu Ile Pro Glu Val Gln Leu Val Gln Ser Gly Gly Gly
            20                  25                  30

```
Val Val Gln Pro Gly Arg Ser Leu Arg Leu Ser Cys Ala Ala Ser Gly
         35                  40                  45

Phe Thr Phe Ser Ser Tyr Ser Met Asn Trp Val Arg Gln Ala Pro Gly
 50                  55                  60

Lys Gly Leu Glu Trp Val Ser Ser Ile Ser Ser Ser Ser Ser Tyr Ile
 65                  70                  75                  80

Tyr Tyr Ala Asp Ser Val Lys Gly Arg Phe Thr Ile Ser Arg Asp Asn
                 85                  90                  95

Ala Lys Asn Thr Leu Tyr Leu Gln Met Asn Ser Leu Arg Ala Glu Asp
                100                 105                 110

Thr Ala Val Tyr Tyr Cys Ala Arg Asp Asn Trp Gly Ser Leu Asp Tyr
                115                 120                 125

Trp Gly Gln Gly Thr Leu Val Thr Val Ser Ser Gly Gly Gly Gly Ser
         130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Gln Ala Ser Gln Asp Ile Ser Asn Tyr Leu Asn Trp Tyr Gln Gln
                180                 185                 190

Lys Pro Gly Lys Ala Pro Lys Leu Leu Ile Tyr Asp Ala Ser Asn Leu
                195                 200                 205

Glu Thr Gly Val Pro Ser Arg Phe Ser Gly Ser Gly Ser Gly Thr Asp
         210                 215                 220

Phe Thr Phe Thr Ile Ser Ser Leu Gln Pro Glu Asp Ile Ala Thr Tyr
225                 230                 235                 240

Tyr Cys Gln Gln Tyr Asp Asn Leu Pro His Met Tyr Thr Phe Gly Gln
                245                 250                 255

Gly Thr Lys Leu Glu Ile Lys Ala Ala Ala Thr Thr Thr Pro Ala Pro
         260                 265                 270

Arg Pro Pro Thr Pro Ala Pro Thr Ile Ala Ser Gln Pro Leu Ser Leu
         275                 280                 285

Arg Pro Glu Ala Cys Arg Pro Ala Ala Gly Gly Ala Val His Thr Arg
         290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Glu Asp Gly Cys Ser Cys Arg Phe Pro
                355                 360                 365

Glu Glu Glu Glu Gly Gly Cys Glu Leu Arg Val Lys Phe Ser Arg Ser
         370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
         435                 440                 445
```

```
-continued

Ser Glu Ile Gly Met Lys Gly Glu Arg Arg Gly Lys Gly His Asp
    450             455             460

Gly Leu Tyr Gln Gly Leu Ser Thr Ala Thr Lys Asp Thr Tyr Asp Ala
465             470             475             480

Leu His Met Gln Ala Leu Pro Pro Arg
                485
```